(12) United States Patent
Mörgelin et al.

(10) Patent No.: US 12,134,640 B2
(45) Date of Patent: Nov. 5, 2024

(54) POLYPEPTIDES AND MEDICAL USES THEREOF

(71) Applicant: COLZYX AB, Lund (SE)

(72) Inventors: Matthias Mörgelin, Anderslöv (SE); Suado Abdillahi, Armadale (AU)

(73) Assignee: COLZYX AB, Lund (SE)

( * ) Notice: Subject to any disclaimer, the term of this patent is extended or adjusted under 35 U.S.C. 154(b) by 0 days.

(21) Appl. No.: 18/483,108

(22) Filed: Oct. 9, 2023

(65) Prior Publication Data

US 2024/0043500 A1 Feb. 8, 2024

Related U.S. Application Data

(60) Continuation of application No. 17/474,434, filed on Sep. 14, 2021, now Pat. No. 11,814,422, which is a (Continued)

(30) Foreign Application Priority Data

Jan. 21, 2016 (GB) ...................................... 1601136

(51) Int. Cl.
| | |
|---|---|
| *C07K 14/78* | (2006.01) |
| *A01N 47/44* | (2006.01) |
| *A61L 15/32* | (2006.01) |
| *A61L 15/44* | (2006.01) |
| *A61L 17/00* | (2006.01) |
| *A61L 17/14* | (2006.01) |
| *A61L 24/00* | (2006.01) |
| *A61L 24/10* | (2006.01) |
| *A61L 27/22* | (2006.01) |
| *A61L 27/24* | (2006.01) |
| *A61L 27/34* | (2006.01) |
| *A61L 27/54* | (2006.01) |
| *A61L 27/60* | (2006.01) |
| *A61L 29/04* | (2006.01) |
| *A61L 29/08* | (2006.01) |
| *A61L 29/16* | (2006.01) |
| *A61L 31/04* | (2006.01) |
| *A61L 31/10* | (2006.01) |
| *A61L 31/16* | (2006.01) |
| *A61P 17/02* | (2006.01) |
| *A61P 31/04* | (2006.01) |

(Continued)

(52) U.S. Cl.
CPC .............. *C07K 14/78* (2013.01); *A01N 47/44* (2013.01); *A61L 15/32* (2013.01); *A61L 15/325* (2013.01); *A61L 15/44* (2013.01); *A61L 17/005* (2013.01); *A61L 17/145* (2013.01); *A61L 24/0015* (2013.01); *A61L 24/102* (2013.01); *A61L 24/108* (2013.01); *A61L 27/227* (2013.01); *A61L 27/24* (2013.01); *A61L 27/34* (2013.01); *A61L 27/54* (2013.01); *A61L 27/60* (2013.01); *A61L 29/045* (2013.01); *A61L 29/048* (2013.01); *A61L 29/085* (2013.01); *A61L 29/16* (2013.01); *A61L 31/044* (2013.01); *A61L 31/047* (2013.01); *A61L 31/10* (2013.01); *A61L 31/16* (2013.01); *A61P 17/02* (2018.01); *A61P 31/04* (2018.01); *C07K 14/4723* (2013.01); *C07K 14/755* (2013.01); *A61K 9/0014* (2013.01); *A61K 9/0019* (2013.01); *A61K 9/0053* (2013.01); *A61K 9/7023* (2013.01); *A61K 38/00* (2013.01); *A61L 2300/252* (2013.01); *A61L 2300/404* (2013.01); *A61L 2300/606* (2013.01); *A61L 2420/00* (2013.01); *A61L 2430/34* (2013.01); *C07K 2319/00* (2013.01)

(58) Field of Classification Search
CPC ................................ C07K 14/78; A61L 27/54
See application file for complete search history.

(56) References Cited

U.S. PATENT DOCUMENTS

| | | |
|---|---|---|
| 7,253,254 B1 | 8/2007 | Sebald |
| 2007/0083334 A1 | 4/2007 | Mintz et al. |
| 2014/0142025 A1 | 5/2014 | Koob |

FOREIGN PATENT DOCUMENTS

| | | |
|---|---|---|
| CN | 105924522 A | 9/2016 |
| WO | 02/086122 A3 | 10/2002 |

(Continued)

OTHER PUBLICATIONS

Bhattacharya, P.K., "Emergence of antibiotic-resistant bacterial strains, methicillin-resistant *Staphylococcus aureus*, extended spectrum beta lactamases, and multi-drug resistance is a problem similar to global warming" Rev. Soc. Bras. Med. Trop. (2014) 47(6):815-6.

(Continued)

*Primary Examiner* — Amber D Steele
(74) *Attorney, Agent, or Firm* — Robert C. Netter, Jr.; Dann, Dorfman, Herrell & Skillman

(57) ABSTRACT

The present invention provides polypeptides comprising or consisting of an amino acid sequence derived from collagen type VI or a fragment, variant, fusion or derivative thereof, or a fusion of said fragment, variant of derivative thereof, wherein the polypeptide, fragment, variant, fusion or derivative is capable of killing or attenuating the growth of microorganisms. Related aspects of the invention provide corresponding isolated nucleic acid molecules, vectors and host cells for making the same. Additionally provided are pharmaceutical compositions comprising a polypeptide of the invention, as well as methods of use of the same in the treatment and/or prevention of microbial infections and in wound care. Also provided are a method of killing microorganisms in vitro and a medical device associated with the pharmaceutical composition.

19 Claims, 30 Drawing Sheets

Figure 1A:
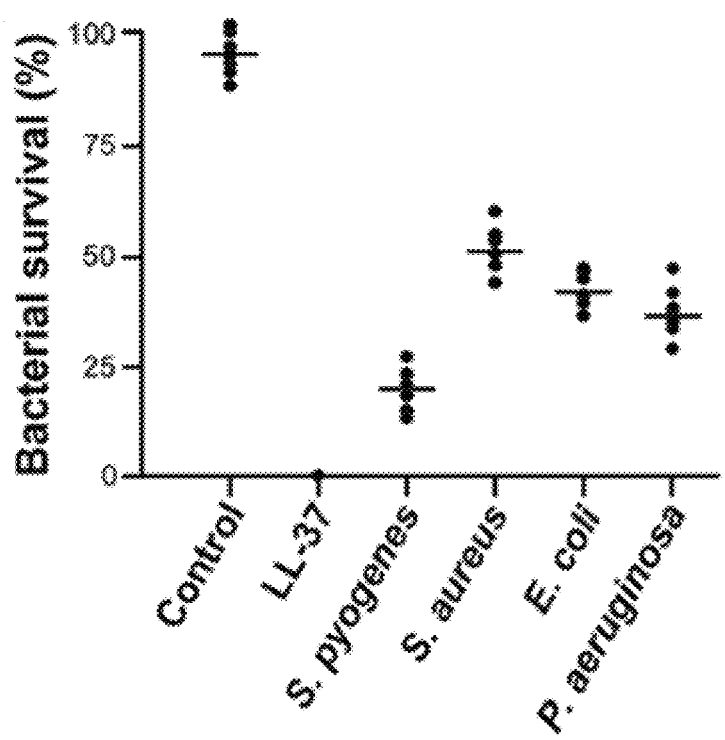

Specification includes a Sequence Listing.

Related U.S. Application Data continuation of application No. 16/839,155, filed on Apr. 3, 2020, now Pat. No. 11,136,374, which is a division of application No. 16/066,912, filed as application No. PCT/EP2017/051246 on Jan. 20, 2017, now Pat. No. 10,793,618.

(51) Int. Cl.
```
C07K 14/47      (2006.01)
C07K 14/755     (2006.01)
A61K 9/00       (2006.01)
A61K 9/70       (2006.01)
A61K 38/00      (2006.01)
```

(56) References Cited

FOREIGN PATENT DOCUMENTS

| | | |
|---|---|---|
| WO | 2007/049062 A2 | 5/2007 |
| WO | 2010/046461 A2 | 4/2010 |
| WO | 2014/140890 A2 | 9/2014 |

OTHER PUBLICATIONS

Bober, et al., "Collagen VI is a subepithelial adhesive target for human respiratory tract pathogens" J. Innate Immun. (2010) 2(2):160-6.
Boman, H.G., "Innate immunity and the normal microflora" Immunol. Rev. (2000) 173:5-16.
Bowdish, et al., "A Re-evaluation of the Role of Host Defence Peptides in Mammalian Immunity" Curr. Prot. Peptide Sci. (2005) 6:35-51.
Bradshaw, J., "Cationic antimicrobial peptides : issues for potential clinical use" BioDrugs (2003) 17(4):233-40.
Brennan, et al., "Antibacterial Activity within Degradation Products of Biological Scaffolds Composed of Extracellular Matrix" Tissue Eng. (2006) 12(10): 2949-2955.
Brogden, K.A., "Antimicrobial Peptides: Pore Formers or Metabolic Inhibitors in Bacteria?" Nat. Rev. Microb. (2005) 238-250.
Brown, et al., "Cationic host defense (antimicrobial) peptides" Curr. Opin. Immunol. (2006) 18(1):24-30.
Cescon, et al., "Collagen VI at a glance" J. Cell. Sci. (2015) 128(19):3525-31.
Chu, et al., "The structure of type VI collagen" Ann. N.Y. Acad. Sci. (1990) 580:55-63.
Chu, et al., "Sequence analysis of alpha 1(VI) and alpha 2(VI) chains of human type VI collagen reveals internal triplication of globular domains similar to the A domains of von Willebrand factor and two alpha 2(VI) chain variants that differ in the carboxy terminus" EMBO J. (1989) 8(7):1939-46.
Chu, et al., "Mosaic structure of globular domains in the human type VI collagen alpha 3 chain: similarity to von Willebrand factor, fibronectin, actin, salivary proteins and aprotinin type protease inhibitors" EMBO J. (1990) 9(2):385-93.
Chu, et al., "Amino acid sequence of the triple-helical domain of human collagen type VI" J. Biol. Chem. (1988) 263(35):18601-6.
Diamond, et al., "The Roles of Antimicrobial Peptides in Innate Host Defense" Curr. Pharm. Des. (2009) 15(21):2377-2392.
Fearon, et al., "The Instructive Role of Innate Immunity in the Acquired Immune Response" Science (1996) 272(5258):50-3.
Fjell, et al., "Designing antimicrobial peptides: form follows function" Nat. Rev. Drug Discov. (2011) 11(1):37-51.
Ganz, T., "Antimicrobial proteins and peptides in host defense" Semin. Respir. Infect. (2001) 16(1):4-10 [Abstract only].
Gara, et al., "Differential and restricted expression of novel collagen VI chains in mouse" Matrix Biol. (2011) 30(4):248-57.
Hancock, et al., "Antimicrobial and host-defense peptides as new anti-infective therapeutic strategies" Nat. Biotechnol. (2006) 24(12):1551-7.

Hawkey, P.M., "The growing burden of antimicrobial resistance" J. Antimicrob. Chemother. (2008) 62 Suppl 1:i1-9.
Hileman, et al., "Glycosaminoglycan-protein interactions: definition of consensus sites in glycosaminoglycan binding proteins" BioEssays (1998) 20:156-167.
Kasetty, et al., "The C-terminal sequence of several human serine proteases encodes host defense functions" J. Innate Immun. (2011) 3(5):471-82.
Lamanade, et al., "The C5 domain of the collagen VI alpha3(VI) chain is critical for extracellular microfibril formation and is present in the extracellular matrix of cultured cells" J. Biol. Chem. (2006) 281(24):16607-14.
Lehrer, et al., "Ultrasensitive assays for endogenous antimicrobial polypeptides" J. Immunol. Methods (1991) 137(2):167-73.
Livermore, D.M., "Has the era of untreatable infections arrived?" J. Antimicrob. Chemother. (2009) 64 Suppl 1:i29-36.
Macvane, S.H., "Antimicrobial Resistance in the Intensive Care Unit: A Focus on Gram-Negative Bacterial Infections" J. Intensive Care Med. (2017) 32(1):25-37.
Maertens, et al., "Cleavage and oligomerization of gliomedin, a transmembrane collagen required for node of ranvier formation" J. Biol. Chem. (2007) 282(14):10647-59.
Malmsten, et al., "Bacterial killing by heparin-binding peptides from PRELP and thrombospondin" Matrix Biol. (2006) 25(5):294-300.
Melo, et al., "Antimicrobial peptides: linking partition, activity and high membrane-bound concentrations" Nat. Rev. Microbiol. (2009) 7(3):245-50.
Oehmcke, et al., "Activation of the human contact system on neutrophil extracellular traps" J. Innate Immun. (2009) 1(3):225-30.
Peters, et al., "Antimicrobial peptides: primeval molecules or future drugs?" PLoS Pathog. (2010) 6(10):e1001067.
Ramachandran, et al., "Gram-positive and gram-negative bacterial toxins in sepsis: a brief review" Virulence (2014) 5(1):213-8.
Ringstad, et al., "Effect of Peptide Length on the Interaction between Consensus Peptides and DOPC/DOPA Bilayers" Langmuir (2006) 22:5042-5050.
Sarikaya, et al., "Antimicrobial activity associated with extracellular matrices" Tissue Eng. (2002) ;8(1):63-71.
Schroder, et al., "Human beta-defensin-2" Int. J. Biochem. Cell Biol. (1999) 31(6):645-51.
Senyurek, et al., "Processing of Laminin a Chains Generates Peptides Involved in Wound Healing and Host Defense" J. Innate Immun. (2014) 6:467-484.
Senyurek, et al., "Peptides derived from the human laminin alpha4 and alpha5 chains exhibit antimicrobial activity" Peptides (2010) 31(8):1468-72.
Shai, Y., "Mechanism of the binding, insertion and destabilization of phospholipid bilayer membranes by alpha-helical antimicrobial and cell non-selective membrane-lytic peptides" Biochim. Biophys. Acta. (1999) 1462(1-2):55-70.
Shai, Y., "Mode of action of membrane active antimicrobial peptides" Biopolymers (2002) 66(4):236-48.
Singh, et al., "Human pathogens utilize host extracellular matrix proteins laminin and collagen for adhesion and invasion of the host" FEMS Microbiol. Rev. (2012) 36(6):1122-80.
Specks, et al., "Structure of recombinant N-terminal globule of type VI collagen alpha 3 chain and its binding to heparin and hyaluronan" EMBO J. (1992) 11(12):4281-90.
Spissinger, et al., "Type VI collagen beaded microfibrils from bovine cornea depolymerize at acidic pH, and depolymerization and polymerization are not influenced by hyaluronan" Matrix Biol. (1995) 14(6):499-505.
Teixeira, et al., "Role of lipids in the interaction of antimicrobial peptides with membranes" Prog. Lipid Res. (2012) 51(2):149-77.
Wang et al., "Apolipoprotein A-I binds and inhibits the human antibacterial/cytotoxic peptide LL-37" J. Biol. Chem. (1998) 273(50):33115-8.
Wimley, W.C., "Describing the Mechanism of Antimicrobial Peptide Action with the Interfacial Activity Model" ACS Chem. Biol. (2010) 5(10): 905-917.
Yount, et al., "Advances in antimicrobial peptide immunobiology" Biopolymers (2006) 84(5):435-58.

(56) References Cited

OTHER PUBLICATIONS

Zasloff, M., "Antimicrobial peptides of multicellular organisms" Nature (2002) 415(6870):389-95.

Antimicrobial Peptide Database, 2003, available at http://aps.unmc.edu/AP/main.php.

Steffen, H., et al. "Naturally Processed Dermcidin-Derived Peptides Do Not Permeabilize Bacterial Membranes and Kill Microorganisms Irrespective of Their Charge" Antimicrob. Agents Chemother. (2006) 50(8):2608-2620.

Abdillahi, et al., "Collagen VI Is Upregulated in COPD and Serves Both as an Adhesive Target and a Bactericidal Barrier for Moraxella catarrhalis" J. Innate Immun. (2015) 7(5):506-17.

Abdillahi, et al., "Collagen VI encodes antimicrobial activity: novel innate host defense properties of the extracellular matrix" J. Innate Immun. (2012) 4(4):371-6.

Andersson, et al., "Antimicrobial activities of heparin-binding peptides" Eur. J. Biochem. (2004) 271(6):1219-26.

Schmidtchen, A., "The multiple faces of host defence peptides and proteins" J. Innate Immun. (2012) 4(4):325-6.

Pasupuleti, et al., "Rational design of antimicrobial C3a analogues with enhanced effects against Staphylococci using an integrated structure and function-based approach" Biochemistry (2008) 47(35):9057-70.

Neumann, et al., "Novel role of the antimicrobial peptide LL-37 in the protection of neutrophil extracellular traps against degradation by bacterial nucleases" J. Innate Immun. (2014) 6(6):860-8.

Gara, et al., "Three Novel Collagen VI Chains with High Homology to the a3 Chain" J. Biol. Chem. (2008) 283(16):10658-10670.

Myint, et al., "Cleavage of Human Corneal Type VI Collagen a3 Chain by Matrix Metalloproteinase-2" Cornea (1996) 15(5):490-496.

Lamande, et al., "The Role of the a3(VI) Chain in Collagen VI Assembly" J. Biol. Chem. (1998) 273(13):7423-7430.

Ball, et al., "The Role of the C1 and C2 A-domains in Type VI Collagen Assembly" J. Biol. Chem. (2001) 276(10):7422-7430.

Becker, et al., "A Structure of a Collagen VI VWA Domain Displays N and C Termini at Opposite Sides of the Protein" Structure (2014) 22:199-208.

Fitzgerald, et al., "The N-terminal N5 Subdomain of the a3(VI) Chain is Important for Collagen VI Microfibril Formation" J. Biol. Chem. (2001) 276(1):187-193.

Abdillahi, et al., "Collagen VI Contains Multiple Host Defense Peptides with Potent In Vivo Activity" The Journal of Immunology (2018) 201:1007-1020.

FIGURE 4

FIG. 5A

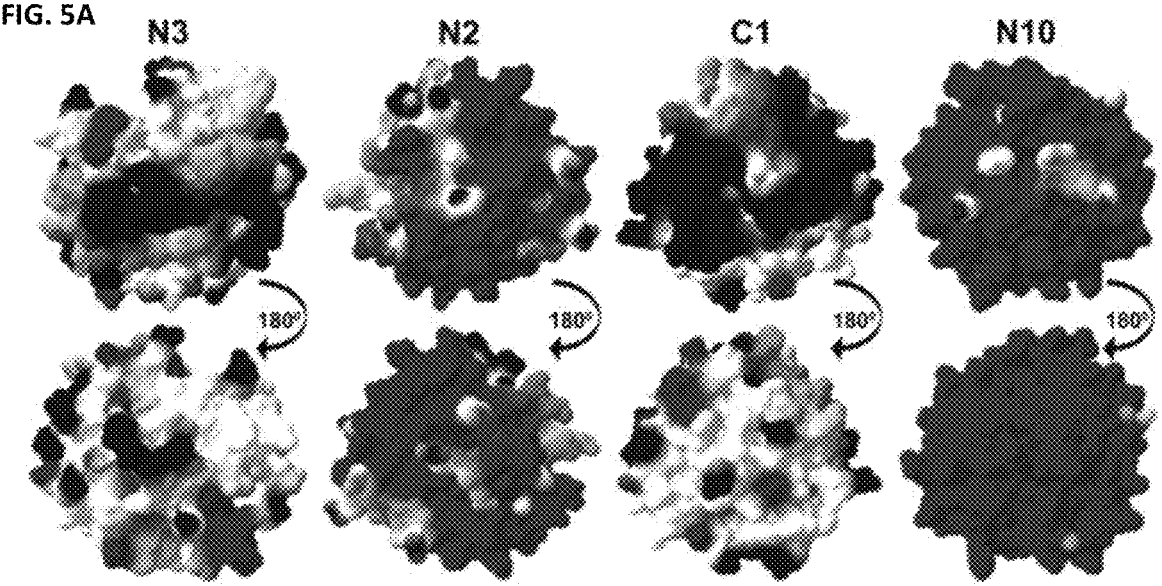

FIG. 5B

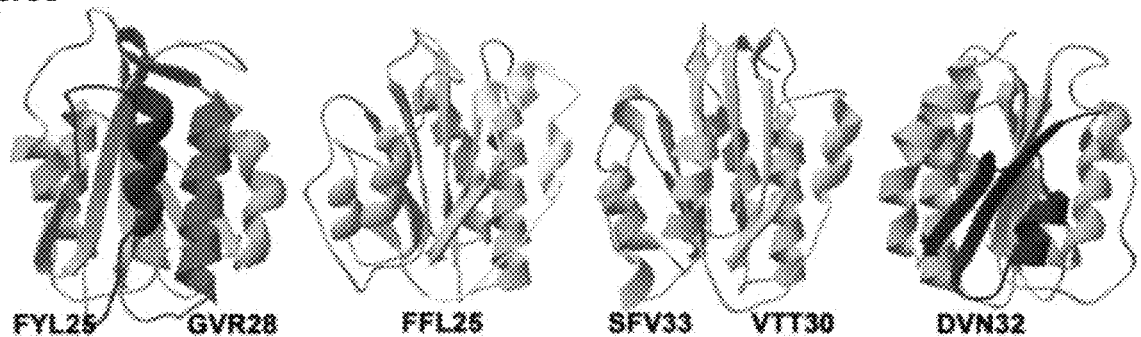

FIG. 5C

Synthetic peptides from VWA domains of collagen α3(VI) used in this study

| VWA domain | Peptide | Sequence | MW (Da) | Net charge | pI |
|---|---|---|---|---|---|
| N3 | GVR28 | GVRPDGFAHIRDFVSRIVRRLNIGPSKV | 3163 | +4 | 11.83 |
| N3 | FYL25 | FYLKTYRSQAPVLDAIRRLRLRGGS | 2937 | +5 | 11.45 |
| N2 | FFL25 | FFLKDFSTKRQIIDAINKVVYKGGR | 2944 | +4 | 10.17 |
| C1 | VTT30 | VTTEIRFADSKRKSVLLDKIKNLQVALTSK | 3403 | +4 | 10.17 |
| C1 | SFV33 | SFVARNTFKRVRNGFLMRKVAVFFSNTPTRASP | 3803 | +7 | 12.60 |
| N10 | DVN32 | DVNVFAIGVEDADEGALKEIASEPLNMHMFNL | 3490 | -6 | 3.95 |

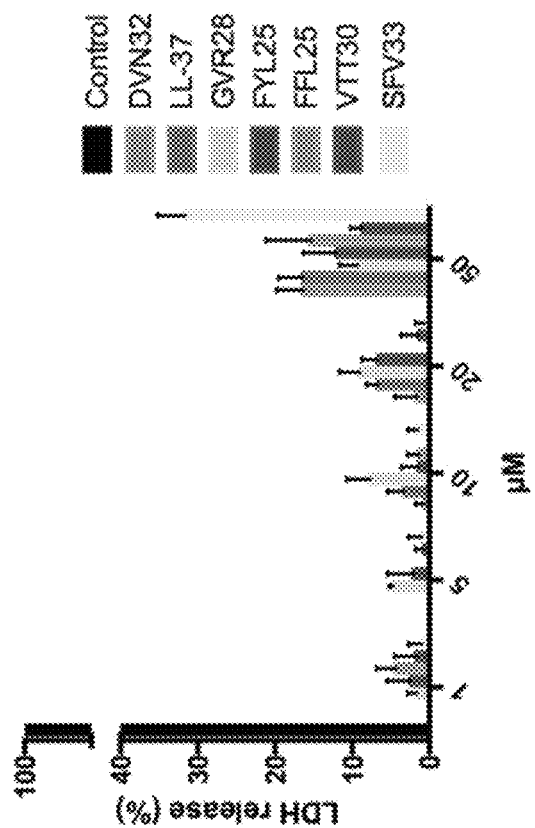
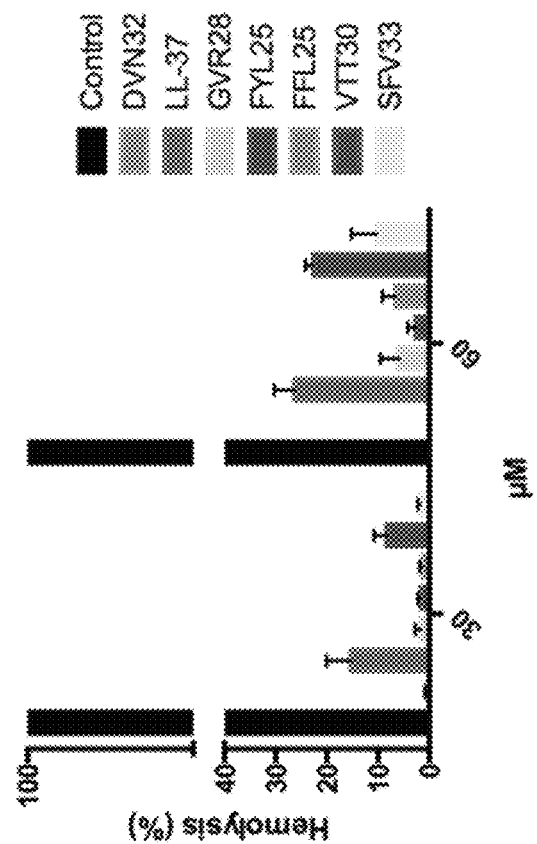
FIG. 11A
FIG. 11B

POLYPEPTIDES AND MEDICAL USES THEREOF

This application is a continuation of U.S. patent application Ser. No. 17/474,434, filed Sep. 14, 2021, which is a continuation of U.S. patent application Ser. No. 16/839,155, filed Apr. 3, 2020, now U.S. Pat. No. 11,136,374, which is a divisional of U.S. patent application Ser. No. 16/066,912, filed Jun. 28, 2018, now U.S. Pat. No. 10,793,618, which is a § 371 application of PCT/EP2017/051246, filed Jan. 20, 2017, which in turn claims priority to GB Application 1601136.3, filed Jan. 21, 2016. The entire disclosure of each of the foregoing applications is incorporated by reference herein.

Incorporated herein by reference in its entirety is the Sequence Listing being concurrently submitted via EFS-Web as a XML file named SeqList, created Oct. 6, 2023, and having a size of 60,905 bytes.

FIELD OF INVENTION

The present invention relates to novel polypeptides derived from a naturally occurring extracellular matrix component protein, collagen type VI, with antimicrobial properties. The invention also relates to the use of these polypeptides in treating microbial infections or in wound care. Also provided are kits, devices and compositions incorporating these polypeptides.

INTRODUCTION

During the last decade, the increase of resistant pathogenic bacteria to conventional antibiotics has become a major threat to global health care (1, 2). Therefore, it is of great interest to develop novel antimicrobial agents in order to fight emerging infectious diseases. Rapid host defence mechanisms are essential in order to overcome the harmful actions of pathogenic bacteria. Antimicrobial peptides (AMPs) are powerful molecules of the innate immune defence system providing a rapid and non-specific response against invading pathogens, which represent the first line of defence against invading pathogens in most multicellular organisms. AMPs exhibit broad-spectrum activity against Gram-positive bacteria, Gram-negative bacteria, fungi and viruses and parasites (3-8). Despite their diverse origins, AMPs share several physicochemical properties, which are crucial for their direct antimicrobial nature. These peptides are relatively small molecules (10-50 amino acids) and usually carry a net positive charge ranging from +2 to +9 (4, 9-10). Another recurring feature is that they often possess ≥30% hydrophobic residues, which enable them to adopt an amphipathic structure upon contact with a lipid-like environment, e.g. the bacterial membrane (4). Presently, more than two thousand AMPs have been isolated from a wide range of species including plants, insects and mammals (see Antimicrobial Peptide Database, aps.unmc.edu/AP/main.php).

It is commonly agreed that AMPs are membrane active and damage the target cell by disrupting the integrity of the membrane (11) or by causing intracellular alterations (12). However, different modes of actions have been proposed for several AMPs but the underlying molecular mechanisms remain under investigation (13-16).

Apart from their direct antimicrobial activity, some peptides (e.g. LL-37) also have immunomodulatory functions such as being chemotactic, neutralizing endotoxin (e.g. LPS), enhancing wound healing, angiogenesis and regulation of the production of pro-inflammatory cytokines (17-18). Their broad-spectrum antimicrobial activity together with a low bacterial resistance mechanism makes these AMPs attractive therapeutic agents against infections (8, 19), but there remains a need for additional antimicrobial therapies and AMPs.

Extracellular matrix (ECM) proteins such as collagens, fibronectin, laminin and vitronectin are attractive targets for pathogenic bacteria in order to adhere, invade and colonize the connective tissue of the host (20). Despite this, a mounting body of evidence shows that ECM proteins may have a protective role during early phase of infection (21-24). Collagen type VI is a ubiquitous extracellular matrix component, which is present in all connective tissues and often associated with basement membranes. Collagen type VI forms complex and extensive beaded microfibrillar network in most connective tissues. The predominant form of collagen type VI is composed of three distinct polypeptide chains, $\alpha1(VI)$, $\alpha2(VI)$ and $\alpha3(VI)$, which form triple helical monomers. Inside the cell, the monomers assemble into dimers and tetramers that are secreted into the extracellular space. There, the tetramers aggregate end-on-end to form microfibrils that become part of extended supramolecular matrix assemblies. More recently, three additional chains ($\alpha4$, $\alpha5$ and $\alpha6$) were discovered, which may substitute for the $\alpha3$-chain in some tissues (9, 10). In terms of structure, each $\alpha$-chain is characterized by a short extended triple-helical region flanked by two large N- and C-terminal globular regions, which share homology with von Willebrand Factor type A domains (VWA) (25-27). VWA is also responsible for protein-protein interaction in the ECM (25-28). The $\alpha1(VI)$ and $\alpha2(VI)$ chains of collagen type VI contain one N-terminal (N1) and two C-terminal (C1 and C2) VWA domains, whereas the $\alpha3(VI)$ is much larger and comprises some ten N-terminal (N10-N1) VWA domains and two C-terminal VWA domains. Additionally, the $\alpha3(VI)$ chain has three C-terminal domains (C3-C5) that share homology with salivary gland proteins, fibronectin type Ill repeats and the Kunitz family of serine protease inhibitors (29). With its unique setup, collagen type VI provides strength, integrity and structure to wide range of tissues. It is also involved in other important biological processes such as apoptosis, autophagy, angiogenesis, fibrosis and tissue repair (30).

It has previously been shown that peptides derived from von Willebrand Factor containing consensus heparin-binding sequences (Cardin and Weintraub motifs) (31) exhibit antimicrobial activity against Gram-positive and Gram-negative bacteria (32-33).

It has previously been demonstrated that collagen type VI binds to *Streptococcus pneumonia* and group A, C and D streptococci (35), leading to bacterial killing (36). Recently, similar adhesive and bactericidal effects of collagen type VI microfibrils against *Moraxella catarrhalis* and other Gram-negative and Gram-positive human pulmonary pathogens were also reported (37). However, no structural or mechanistic explanations for such anecdotal observations have been provided.

Thus, there remains a need for the identification of new antimicrobial agents, and especially agents capable of killing or inhibiting the growth of bacteria such as MRSA that have developed resistance against conventional antibiotics.

SUMMARY OF THE INVENTION

A first aspect of the invention provides a polypeptide comprising or consisting of an amino acid sequence derived from a collagen type VI, or a fragment, variant, fusion or derivative thereof, or a fusion of said fragment, variant of derivative thereof, wherein the polypeptide, fragment, variant, fusion or derivative is capable of killing or attenuating the growth of microorganisms.

It will be appreciated by persons skilled in the art that the collagen type VI may be from a human or non-human source. For example, the collagen type VI may be derived (directly or indirectly) from a non-human mammal, such as an ape (e.g. chimpanzee, bonobo, gorilla, gibbon and orangutan), monkey (e.g. macaque, baboon and colobus), rodent (e.g. mouse, rat) or ungulates (e.g. pig, horse and cow).

Thus, by "collagen type VI" (also "collagen VI") we include naturally occurring human collagen type VI and homologues thereof, such as bovine collagen type VI. In one preferred embodiment, the polypeptide is derived from human collagen type VI.

By an amino acid sequence "derived from" collagen type VI we include amino acid sequences found within the amino acid sequence of a naturally occurring collagen type VI protein. In particular, we include amino acid sequences that comprise at least five contiguous amino acids from the sequence of a naturally occurring collagen type VI, but exclude the full length protein. For example, in one embodiment the amino acid sequence may contain at least 5 contiguous amino acids from collagen type VI, for example at least 6, 7, 8, 9, 10, 11, 12, 13, 14, 15, 16, 17, 18, 19, 20, 21, 22, 23, 24, 25, 30, 40, or 50 contiguous amino acids from collagen type VI. Thus, the amino acid sequence derived from collagen type VI corresponds to a fragment of collagen type VI having antimicrobial activity.

By "capable of killing or attenuating the growth of microorganisms" we include polypeptides with antimicrobial activity. The antimicrobial activity may be in whole or in part, and may be dose dependent. This may be demonstrated by, for example, radial diffusion assays.

The microorganisms against which the polypeptides of the invention are efficacious may be selected from the group consisting of bacteria, mycoplasmas, yeasts, fungi and viruses.

In one embodiment, the polypeptide of the invention is capable of binding to the membrane of the microorganism. In another embodiment, the polypeptide may have affinity for negatively charged surfaces, for example a bacterial membrane. This affinity may be tested by, for example, affinity to heparin, wherein higher affinity to heparin indicates higher affinity to negatively charged surfaces.

Advantageously, the affinity or binding capability of the polypeptide is comparable to or greater than that of LL-37. Thus, in one embodiment, the polypeptide is capable of exhibiting an antimicrobial effect greater than or equal to that of LL-37 (i.e. LLGDFFRKSKEKIGKEFKRIVQRIKD-FLRNLVPRTES; SEQ ID NO: 36).

In one embodiment, the polypeptide is capable of causing structural alterations to the microorganism, including, for example, membrane perturbations, blebbing or exudation of cytoplasmic constituents.

Thus, the polypeptide may be capable of causing disruption of the membrane of the microorganisms. This can, for example, be quantified through microscopy studies, such as electron microscopy or fluorescence microscopy, studying the uptake of fluorescent molecules by the microorganisms.

In a further embodiment, the polypeptide may be capable of promoting wound closure and/or wound healing.

By "promoting wound closure" and/or "wound healing" we include aiding the healing process of the wound, for example by accelerating healing. For example, the wound care product may be capable of enhancing epithelial regeneration and/or healing of wound epithelia and/or wound stroma. In one embodiment, the wound care product may be capable of enhancing the proliferation of epithelial and/or stromal cells through a non-lytic mechanism. The wound closing capability may be quantified by, for example, cell scratch experiments.

Thus, the polypeptide may have a role in wound care by promoting wound closure/healing and/or by preventing infection of a wound.

The wounds to be treated by the polypeptides of the invention may be extracorporeal (i.e. surface wounds of the skin and underlying tissue) and/or intracorporeal (such as internal wounds due to organ transplantation or removal of tissue/parts of organs, e.g. following colon surgery).

It will be appreciated by persons skilled in the art that the polypeptides of the invention may exert an antimicrobial effect against Gram-positive and/or Gram-negative bacteria. For example, the microorganisms may be bacteria selected from the group consisting of: *Pseudomonas aeruginosa, Staphylococcus aureus, Escherichia coli,* group A *streptococcus* (e.g. *Streptococcus pyogenes*), group B *streptococcus* e.g. *Streptococcus agalactiae*), group C *streptococcus* (e.g. *Streptococcus dysgalactiae*), group D *streptococcus* (e.g. *Entero-coccus faecalis*), group F *streptococcus* (e.g. *Streptococcus anginosus*), group G *streptococcus* (e.g. *Streptococcus dysgalactiae equisimilis*), alpha-hemolytic *streptococcus* (e.g. *Streptococcus viridans, Streptococcus pneumoniae*), *Streptococcus bovis, Streptococcus mitis, Streptococcus anginosus, Streptococcus sanguinis, Streptococcus suis, Streptococcus mutans, Moraxella catarrhalis,* Non-typeable *Haemophilus influenzae* (NTHi), *Haemophilus influenzae* b (Hib), *Actinomyces naeslundii, Fusobacterium nucleatum, Prevotella intermedia, Klebsiella pneumoniae, Enterococcus cloacae, Enterococcus faecalis, Staphylococcus epidermidis,* multi-resistant *Pseudomonas aeruginosa* (MRPA), multi-resistant *Staphylococcus aureus* (MRSA), multi-resistant *Escherichia coli* (MREC), multi-resistant *Staphylococcus epidermidis* (MRSE) and multi-resistant *Klebsiella pneumoniae* (MRKP).

In one embodiment the microorganisms are bacteria which are resistant to one or more conventional antibiotic agents.

By "conventional antibiotic agent" we include known agents that are capable of killing or attenuating the growth of microorganisms, for example natural and synthetic penicillins and cephalosporins, sulphonamides, erythromycin, kanomycin, tetracycline, chloramphenicol, rifampicin and including gentamicin, ampicillin, benzypenicillin, benethamine penicillin, benzathine penicillin, phenethicillin, phenoxy-methyl penicillin, procaine penicillin, cloxacillin, flucloxacillin, methicillin sodium, amoxicillin, bacampicillin hydrochloride, ciclacillin, mezlocillin, pivampicillin, talampicillin hydrochloride, carfecillin sodium, piperacillin, ticarcillin, mecillinam, pirmecillinan, cefaclor, cefadroxil, cefotaxime, cefoxitin, cefsulodin sodium, ceftazidime, ceftizoxime, cefuroxime, cephalexin, cephalothin, cephamandole, cephazolin, cephradine, latamoxef disodium, aztreonam, chlortetracycline hydrochloride, clomocycline sodium, demeclocydine hydrochloride, doxycycline, lymecycline, minocycline, oxytetracycline, amikacin, framycetin sulphate, neomycin sulphate, netilmicin, tobramycin, colistin, sodium fusidate, polymyxin B sulphate, spectinomycin, vancomycin, calcium sulphaloxate, sulfametopyrazine, sulphadiazine, sulphadimidine, sulphaguanidine, sulphaurea, capreomycin, metronidazole, tinidazole, cinoxacin, ciprofloxacin, nitrofurantoin, hexamine, streptomycin, carbenicillin, colistimethate, polymyxin B, furazolidone, nalidixic acid, trimethoprim-sulfamethoxazole, clindamycin, lincomycin, cycloserine, isoniazid, ethambutol, ethionamide, pyrazinamide and the like; antifungal agents, for example miconazole, ketoconazole, itraconazole, fluconazole, amphotericin, flucytosine, griseofulvin, natamycin, nystatin, and the like; and anti-viral agents such as acyclovir, AZT, ddI, amantadine hydrochloride, inosine pranobex, vidarabine, and the like.

Thus, in one embodiment, the microorganism is selected from the group consisting of: multidrug-resistant *Staphylococcus aureus* (MRSA) (methicillin resistant *Staphylococcus aureus*),multidrug-resistant *Pseudomonas aeruginosa* (MRPA), multidrug-resistant *Escherichia coli* (MREC), multidrug-resistant *Staphylococcus epidermidis* (MRSE) and multidrug-resistant *Klebsiella pneumoniae* (MRKP).

Advantageously, the polypeptide according to the first aspect of the invention exhibits selective toxicity to microbial agents. By 'selective' we mean the polypeptide is preferentially toxic to one or more microorganisms (such as bacteria, mycoplasmas, yeasts, fungi and/or viruses) compared to mammalian, e.g. human, host cells. For example, the toxicity of the polypeptide to a target microorganism is at least two-fold greater than the toxicity of that polypeptide to mammalian cells, more preferably at least three-fold, at least four-fold, at least five-fold, at least six-fold, at least eight-fold, at least ten-fold, at least fifteen-fold or at least twenty fold.

Conveniently, the polypeptide is substantially non-toxic to mammalian, e.g. human, cells.

For example, the polypeptide may not exhibit cytotoxicity to erythrocytes or monocytes at concentrations at concentrations which can be used to kill microorganisms such as bacteria. In one embodiment the polypeptide does not exhibit cytotoxicity at a concentration of up to 30 μM, or alternatively at a concentration of up to 50 μM.

In this way, when the compounds are used to treat microbial infections, for example, dosing regimens can be selected such that microbial cells are destroyed with minimal damage to healthy host tissue. Thus, the polypeptide may exhibit a 'therapeutic window'.

In one embodiment, the polypeptide is capable of exerting an anti-endotoxic effect.

By "anti-endotoxic effect" we include polypeptides which counteract the effects induced by endotoxins. For example, in one embodiment the polypeptide is capable of suppressing, at least in part, LPS induction of nitrite.

In one embodiment, the polypeptide is derived from or shows amino acid sequence homology to a VWA domain, for example a globular VWA domain. Thus, the polypeptide may comprise or consist of an amino acid sequence which corresponds to at least five (for example, at least 10, 15, 20 or more) contiguous amino acids of a VWA domain, or an amino acid sequence which has at least 70% (for example at least 80%, 90% or 95%) identity with such as sequence.

In a further embodiment, the polypeptide may comprise or consist of an intact VWA domain.

By "VWA domain" we include the type A domains of von Willebrand factor, and domains showing homology to the type A domains of von Willebrand factor, as well as VWA-domain containing regions.

In one embodiment, the polypeptide is derived from the α3 chain of collagen type VI. Thus, the polypeptide may be derived from the α3N or α3C regions. For example, the polypeptide may be derived from the N2, N3 or C1 domain of the α3 chain of collagen type VI.

In an alternative embodiment, the polypeptide is derived from the α4 chain of collagen type VI.

In another alternative embodiment, the polypeptide is derived from the α5 chain of collagen type VI.

In a further alternative embodiment, the polypeptide is derived from the α6 chain of collagen type VI.

In a still further alternative embodiment, the polypeptide is derived from the α2 chain of collagen type VI, for example from the α2N region.

It will be appreciated by persons skilled in the art that the polypeptides of the invention may have cationic residues on their surface, or cationic sequence motifs therein.

Thus, in one embodiment, the polypeptide has a net positive charge. For example, the polypeptide may have a charge ranging from between +2 to +9.

In a further embodiment, the polypeptide has at least 30% hydrophobic residues.

In a still further embodiment, the polypeptide may have an amphipathic structure.

Exemplary polypeptides of the first aspect of the invention comprise or consist of the amino acid sequence of any one of SEQ ID NOs: 1 to 23 (as shown in Table 1) or a fragment, variant, fusion or derivative thereof, or a fusion of said fragment, variant or derivative thereof, which retains an antimicrobial activity of any one of SEQ ID NOs:1 to 23.

TABLE 1

Exemplary polypeptides of the invention

| Peptide | Sequence | MW | Charge |
|---------|----------|-----|--------|
| GVR28 | GVRPDGFAHIRDFVSRIVRRLNIGPSKV [SEQ ID NO: 1] | 3,163 | 4 |
| FYL25 | FYLKTYRSQAPVLDAIRRLRLRGGS [SEQ ID NO: 2] | 2,937 | 5 |
| FFL25 | FFLKDFSTKRQIIDAINKVVYKGGR [SEQ ID NO: 3] | 2,944 | 4 |
| VTT30 | VTTEIRFADSKRKSVLLDKIKNLQVALTSK [SEQ ID NO: 4] | 3,403 | 4 |
| SFV33 | SFVARNTFKRVRNGFLMRKVAVFFSNTPTRASP [SEQ ID NO: 5] | 3,803 | 7 |
| DVN32 | DVNVFAIGVEDADEGALKEIASEPLNMHMFNL [SEQ ID NO: 6] | 3,490 | -6 |
| KPE20 | KPEILNLVKRMKIKTGKALN [SEQ ID NO: 7] | 2,295 | 5 |
| GFA20 | GFAHIRDFVSRIVRRLNIGP [SEQ ID NO: 8] | 2,324 | 5 |
| QAP20 | QAPVLDAIRRLRLRGGSPLN [SEQ ID NO: 9] | 2,203 | 3 |

TABLE 1-continued

Exemplary polypeptides of the invention

| Peptide | Sequence | MW | Charge |
|---|---|---|---|
| KGF20 | KGFESKVDAILNRISQMHRV [SEQ ID NO: 10] | 2,329 | 3 |
| RKV20 | RKVAVFFSNTPTRASPQLRE [SEQ ID NO: 11] | 2,305 | 2 |
| VAA20 | VAAKPVATKMAVRPPVAVKP [SEQ ID NO: 12] | 2,031 | 3 |
| AAK20 | AAKPVATKPEVPRPQAAKPA [SEQ ID NO: 13] | 2,027 | 4 |
| TTK20 | TTKPVTTTKPVTTTTKPVTT [SEQ ID NO: 14] | 2,103 | 3 |
| AAA76 | AAAKPAPAKPVAAKPVATKMATVRPPVAVKPATAAKPVAAKPA AVRPPAAAAAKPVATKPEVPRPQAAKPAATKPA SEQ ID NO: 15] | 7,324 | 13 |
| TSS36 | TSSPTSNPVTTTKPVTTTKPVTTTTKPVTTTTKPVT [SEQ ID NO: 16] | 3,703 | 4 |
| YDR20 | YDRLIKESRRQKTRVFAVVI [SEQ ID NO: 17] | 2 473 | 4 |
| EQN20 | EQNFHKARRFVEQVARRLTL [SEQ ID NO: 18] | 2 499 | 3 |
| VVH20 | VVHAINAIVRSPRGGARRHA [SEQ ID NO: 19] | 2 137 | 4 |
| LRL20 | LRLKPYGALVDKVKSFTKRF [SEQ ID NO: 20] | 2 367 | 5 |
| FTK20 | FTKRFIDNLRDYYRCDRNL [SEQ ID NO: 21] | 2 665 | 3 |
| RDA20 | RDALKSSVDAVKYFGKGTYT [SEQ ID NO: 22] | 2 206 | 2 |
| TKR20 | TKRFAKRLAERFLTAGRTDP [SEQ ID NO: 23] | 2 335 | 4 |

For example, the polypeptide of the invention may comprise or consist of an amino acid sequence selected from the group consisting of SEQ ID NOs& 1 to 5:

"GVR28":
[SEQ ID NO: 1]
GVRPDGFAHIRDFVSRIVRRLNIGPSKV

"FYL25":
[SEQ ID NO: 2]
FYLKTYRSQAPVLDAIRRLRLRGGS

"FFL25":
[SEQ ID NO: 3]
FFLKDFSTKRQIIDAINKVVYKGGR

"VTT30":
[SEQ ID NO: 4]
VTTEIRFADSKRKSVLLDKIKNLQVALTSK

"SFV33":
[SEQ ID NO: 5]
SFVARNTFKRVRNGFLMRKVAVFFSNTPTRASP or a fragment, variant, fusion or derivative thereof, or a fusion of said fragment, variant or derivative thereof, which retains an antimicrobial activity of any one of SEQ ID NOs:1 to 5.

It will be appreciated by persons skilled in the art that the term 'amino acid', as used herein, includes the standard twenty genetically-encoded amino acids and their corresponding stereoisomers in the 'D' form (as compared to the natural 'L' form), omega-amino acids other naturally-occurring amino acids, unconventional amino acids (e.g., α,α-disubstituted amino acids, N-alkyl amino acids, etc.) and chemically derivatised amino acids (see below).

When an amino acid is being specifically enumerated, such as 'alanine' or 'Ala' or 'A', the term refers to both L-alanine and D-alanine unless explicitly stated otherwise. Other unconventional amino acids may also be suitable components for polypeptides of the present invention, as long as the desired functional property is retained by the polypeptide. For the peptides shown, each encoded amino acid residue, where appropriate, is represented by a single letter designation, corresponding to the trivial name of the conventional amino acid.

In one embodiment, the polypeptides of the invention comprise or consist of L-amino acids.

Where the polypeptide comprises an amino acid sequence according to a reference sequence (for example, SEQ ID NOs: 1 to 23), it may comprise additional amino acids at its N- and/or C-terminus beyond those of the reference sequence, for example, the polypeptide may comprise additional amino acids at its N-terminus. Likewise, where the polypeptide comprises a fragment, variant or derivative of an amino acid sequence according to a reference sequence, it may comprise additional amino acids at its N- and/or C-terminus.

In one embodiment, the polypeptide comprises or consists of a fragment of the amino acid sequence according to a reference sequence (for example, a fragment of any one of SEQ ID NOs: 1 to 23). Thus, the polypeptide may comprise or consist of at least 5 contiguous amino acid of the reference sequence, for example at least 6, 7, 8, 9, 10, 11, 12, 13, 14, 15, 16, 17, 18, 19, 20, 21, 22, 23, 24, 25, 26 or 27 contiguous amino acids, e.g. of any one of SEQ ID NOs: 1 to 23.

It will be further appreciated by persons skilled in the art that the polypeptide of the invention may comprise or consist of a variant of the amino acid sequence according to a reference sequence (for example, a variant of any one of SEQ ID NOs: 1 to 23, or fragment of said variant. Such a variant may be non-naturally occurring.

By "variants" of the polypeptide we include insertions, deletions and substitutions, either conservative or non-conservative. For example, conservative substitution refers to the substitution of an amino acid within the same general class (e.g. an acidic amino acid, a basic amino acid, a non-polar amino acid, a polar amino acid or an aromatic amino acid) by another amino acid within the same class. Thus, the meaning of a conservative amino acid substitution and non-conservative amino acid substitution is well known in the art. In particular, we include variants of the polypeptide which exhibit an antimicrobial activity.

In one embodiment, the variant has an amino acid sequence which has at least 50% identity with the amino acid sequence according to a reference sequence (for example, SEQ ID NOs: 1 to 23) or a fragment thereof, for example at least 55%, 60%, 65%, 70%, 75%, 80%, 85%, 90%, 95%, 96%, 97%, 98% or at least 99% identity.

The percent sequence identity between two polypeptides may be determined using suitable computer programs, for example the GAP program of the University of Wisconsin Genetic Computing Group and it will be appreciated that percent identity is calculated in relation to polypeptides whose sequences have been aligned optimally.

The alignment may alternatively be carried out using the Clustal W program (as described in Thompson et al., 1994, *Nuc. Acid Res.* 22:4673-4680, which is incorporated herein by reference).

The parameters used may be as follows:
Fast pairwise alignment parameters: K-tuple(word) size; 1, window size; 5, gap penalty; 3, number of top diagonals; 5. Scoring method: x percent.
Multiple alignment parameters: gap open penalty; 10, gap extension penalty; 0.05.
Scoring matrix: BLOSUM.

Alternatively, the BESTFIT program may be used to determine local sequence alignments.

For example, in one embodiment, amino acids from the above reference sequences may be mutated in order to reduce proteolytic degradation of the polypeptide, for example by I,F to W modifications (see Strömstedt et al, *Antimicrobial Agents Chemother* 2009, 53, 593, which is incorporated herein by reference).

Variants may be made using the methods of protein engineering and site-directed mutagenesis well known in the art using the recombinant polynucleotides (see example, see *Molecular Cloning: a Laboratory Manual*, 3rd edition, Sambrook & Russell, 2000, Cold Spring Harbor Laboratory Press, which is incorporated herein by reference).

In a further embodiment, the polypeptide comprises or consists of an amino acid which is a species homologue of any one of the above amino acid sequences (e.g. SEQ ID NOS: 1 to 23). By "species homologue" we include that the polypeptide corresponds to the same amino acid sequence within an equivalent protein from a non-human species, i.e. which polypeptide exhibits the maximum sequence identity with of any one of SEQ ID NOS: 1 to 23 (for example, as measured by a GAP or BLAST sequence comparison). Typically, the species homologue polypeptide will be the same length as the human reference sequence (i.e. SEQ ID NOS: 1 to 23).

In a still further embodiment, the polypeptide comprises or consists of a fusion protein.

By "fusion" of a polypeptide we include an amino acid sequence corresponding to a reference sequence (for example, any one of SEQ ID NOs: 1 to 23, or a fragment or variant thereof) fused to any other polypeptide. For example, the said polypeptide may be fused to a polypeptide such as glutathione-S-transferase (GST) or protein A in order to facilitate purification of said polypeptide. Examples of such fusions are well known to those skilled in the art. Similarly, the said polypeptide may be fused to an oligo-histidine tag such as His6 or to an epitope recognised by an antibody such as the well-known Myc tag epitope. In addition, fusions comprising a hydrophobic oligopeptide end-tag may be used. Fusions to any variant or derivative of said polypeptide are also included in the scope of the invention. It will be appreciated that fusions (or variants or derivatives thereof) which retain desirable properties, such as an antimicrobial activity, are preferred.

The fusion may comprise a further portion which confers a desirable feature on the said polypeptide of the invention; for example, the portion may be useful in detecting or isolating the polypeptide, or promoting cellular uptake of the polypeptide. The portion may be, for example, a biotin moiety, a streptavidin moiety, a radioactive moiety, a fluorescent moiety, for example a small fluorophore or a green fluorescent protein (GFP) fluorophore, as well known to those skilled in the art. The moiety may be an immunogenic tag, for example a Myc tag, as known to those skilled in the art or may be a lipophilic molecule or polypeptide domain that is capable of promoting cellular uptake of the polypeptide, as known to those skilled in the art.

It will be appreciated by persons skilled in the art that the polypeptide of the invention may comprise one or more amino acids that are modified or derivatised, for example by PEGylation, amidation, esterification, acylation, acetylation and/or alkylation.

As appreciated in the art, pegylated proteins may exhibit a decreased renal clearance and proteolysis, reduced toxicity, reduced immunogenicity and an increased solubility [Veronese, F. M. and J. M. Harris, Adv Drug Deliv Rev, 2002. 54(4): p. 453-6., Chapman, A. P., Adv Drug Deliv Rev, 2002. 54(4): p. 531-45] (incorporated herein by reference). Pegylation has been employed for several protein-based drugs including the first pegylated molecules asparaginase and adenosine deaminase [Veronese, F. M. and J. M. Harris, Adv Drug Deliv Rev, 2002. 54(4): p. 453-6., Veronese, F. M. and G. Pasut, Drug Discov Today, 2005. 10(21): p. 1451-8] (incorporated herein by reference).

In order to obtain a successfully pegylated protein, with a maximally increased half-life and retained biological activity, several parameters that may affect the outcome are of importance and should be taken into consideration. The PEG molecules may differ, and PEG variants that have been used for pegylation of proteins include PEG and monomethoxy-PEG. In addition, they can be either linear or branched [Wang, Y. S., et al., Adv Drug Deliv Rev, 2002. 54(4): p. 547-70] (incorporated herein by reference). The size of the PEG molecules used may vary and PEG moieties ranging in size between 1 and 40 kDa have been linked to proteins [Wang, Y. S., et al., Adv Drug Deliv Rev, 2002. 54(4): p. 547-70., Sato, H., Adv Drug Deliv Rev, 2002. 54(4): p. 487-504, Bowen, S., et al., Exp Hematol, 1999. 27(3): p. 425-32, Chapman, A. P., et al., Nat Biotechnol, 1999. 17(8): p. 780-3] (incorporated herein by reference). In addition, the number of PEG moieties attached to the protein may vary, and examples of between one and six PEG units being attached to proteins have been reported [Wang, Y. S., et al., Adv Drug Deliv Rev, 2002. 54(4): p. 547-70., Bowen, S., et al., Exp Hematol, 1999. 27(3): p. 425-32] (incorporated herein by reference). Furthermore, the presence or absence of a linker between PEG as well as various reactive groups for conjugation have been utilised. Thus, PEG may be linked to N-terminal amino groups, or to amino acid residues with reactive amino or hydroxyl groups (Lys, His, Ser, Thr and Tyr) directly or by using γ-amino butyric acid as a linker. In addition, PEG may be coupled to carboxyl (Asp, Glu, C-terminal) or sulfhydryl (Cys) groups. Finally, Gln residues may be specifically pegylated using the enzyme transglutaminase and alkylamine derivatives of PEG has been described [Sato, H., Adv Drug Deliv Rev, 2002. 54(4): p. 487-504] (incorporated herein by reference).

It has been shown that increasing the extent of pegylation results in an increased in vivo half-life. However, it will be appreciated by persons skilled in the art that the pegylation process will need to be optimised for a particular protein on an individual basis.

PEG may be coupled at naturally occurring disulphide bonds as described in WO 2005/007197, which is incorporated herein by reference. Disulfide bonds can be stabilised through the addition of a chemical bridge which does not compromise the tertiary structure of the protein. This allows the conjugating thiol selectivity of the two sulphurs comprising a disulfide bond to be utilised to create a bridge for the site-specific attachment of PEG. Thereby, the need to engineer residues into a peptide for attachment of to target molecules is circumvented.

A variety of alternative block copolymers may also be covalently conjugated as described in WO 2003/059973, which is incorporated herein by reference. Therapeutic polymeric conjugates can exhibit improved thermal properties, crystallisation, adhesion, swelling, coating, pH dependent conformation and biodistribution. Furthermore, they can achieve prolonged circulation, release of the bioactive in the proteolytic and acidic environment of the secondary lysosome after cellular uptake of the conjugate by pinocytosis and more favourable physicochemical properties due to the characteristics of large molecules (e.g. increased drug solubility in biological fluids). Block copolymers, comprising hydrophilic and hydrophobic blocks, form polymeric micelles in solution. Upon micelle disassociation, the individual block copolymer molecules are safely excreted.

Chemical derivatives of one or more amino acids may also be achieved by reaction with a functional side group. Such derivatised molecules include, for example, those molecules in which free amino groups have been derivatised to form amine hydrochlorides, p-toluene sulphonyl groups, carboxybenzoxy groups, t-butyloxycarbonyl groups, chloroacetyl groups or formyl groups. Free carboxyl groups may be derivatised to form salts, methyl and ethyl esters or other types of esters and hydrazides. Free hydroxyl groups may be derivatised to form O-acyl or O-alkyl derivatives. Also included as chemical derivatives are those peptides which contain naturally occurring amino acid derivatives of the twenty standard amino acids. For example: 4-hydroxyproline may be substituted for proline; 5-hydroxylysine may be substituted for lysine; 3-methylhistidine may be substituted for histidine; homoserine may be substituted for serine and ornithine for lysine. Derivatives also include peptides containing one or more additions or deletions as long as the requisite activity is maintained. Other included modifications are amidation, amino terminal acylation (e.g. acetylation or thioglycolic acid amidation), terminal carboxylamidation (e.g. with ammonia or methylamine), and the like terminal modifications.

It will be further appreciated by persons skilled in the art that peptidomimetic compounds may also be useful. Thus, by "polypeptide" we include peptidomimetic compounds which have an antimicrobial activity. The term "peptidomimetic" refers to a compound that mimics the conformation and desirable features of a particular peptide as a therapeutic agent.

For example, the polypeptides of the invention include not only molecules in which amino acid residues are joined by peptide (—CO—NH—) linkages but also molecules in which the peptide bond is reversed. Such retro-inverso peptidomimetics may be made using methods known in the art, for example such as those described in Meziere et al. (1997) J. Immunol. 159, 3230-3237, which is incorporated herein by reference. This approach involves making pseudopeptides containing changes involving the backbone, and not the orientation of side chains. Retro-inverse peptides, which contain NH—CO bonds instead of CO—NH peptide bonds, are much more resistant to proteolysis. Alternatively, the polypeptide of the invention may be a peptidomimetic compound wherein one or more of the amino acid residues are linked by a -y(CH$_2$NH)— bond in place of the conventional amide linkage.

In a further alternative, the peptide bond may be dispensed with altogether provided that an appropriate linker moiety which retains the spacing between the carbon atoms of the amino acid residues is used; it may be advantageous for the linker moiety to have substantially the same charge distribution and substantially the same planarity as a peptide bond.

It will be appreciated that the polypeptide may conveniently be blocked at its N- or C-terminal region so as to help reduce susceptibility to exoproteolytic digestion.

A variety of uncoded or modified amino acids such as D-amino acids and N-methyl amino acids have also been used to modify mammalian peptides. In addition, a presumed bioactive conformation may be stabilised by a covalent modification, such as cyclisation or by incorporation of lactam or other types of bridges, for example see Veber et al., 1978, Proc. Natl. Acad. Sci. USA 75:2636 and Thursell et al., 1983, Biochem. Biophys. Res. Comm. 111:166, which are incorporated herein by reference.

A common theme among many of the synthetic strategies has been the introduction of some cyclic moiety into a peptide-based framework. The cyclic moiety restricts the conformational space of the peptide structure and this frequently results in an increased specificity of the peptide for a particular biological receptor. An added advantage of this strategy is that the introduction of a cyclic moiety into a peptide may also result in the peptide having a diminished sensitivity to cellular peptidases.

Thus, exemplary polypeptides of the invention comprise terminal cysteine amino acids. Such a polypeptide may exist in a heterodetic cyclic form by disulphide bond formation of the mercaptide groups in the terminal cysteine amino acids or in a homodetic form by amide peptide bond formation between the terminal amino acids. As indicated above, cyclising small peptides through disulphide or amide bonds between the N- and C-terminal region cysteines may circumvent problems of specificity and half-life sometime observed with linear peptides, by decreasing proteolysis and also increasing the rigidity of the structure, which may yield higher specificity compounds. Polypeptides cyclised by disulphide bonds have free amino and carboxy-termini which still may be susceptible to proteolytic degradation, while peptides cyclised by formation of an amide bond between the N-terminal amine and C-terminal carboxyl and hence no longer contain free amino or carboxy termini. Thus, the peptides of the present invention can be linked either by a C—N linkage or a disulphide linkage.

The present invention is not limited in any way by the method of cyclisation of peptides, but encompasses peptides whose cyclic structure may be achieved by any suitable method of synthesis. Thus, heterodetic linkages may include, but are not limited to formation via disulphide, alkylene or sulphide bridges. Methods of synthesis of cyclic homodetic peptides and cyclic heterodetic peptides, including disulphide, sulphide and alkylene bridges, are disclosed in U.S. Pat. No. 5,643,872, which is incorporated herein by reference. Other examples of cyclisation methods include cyclization through click chemistry, epoxides, aldehyde-amine reactions, as well as and the methods disclosed in U.S. Pat. No. 6,008,058, which is incorporated herein by reference.

A further approach to the synthesis of cyclic stabilised peptidomimetic compounds is ring-closing metathesis (RCM). This method involves steps of synthesising a peptide precursor and contacting it with an RCM catalyst to yield a conformationally restricted peptide. Suitable peptide precursors may contain two or more unsaturated C—C bonds. The method may be carried out using solid-phase-peptide-synthesis techniques. In this embodiment, the precursor, which is anchored to a solid support, is contacted with a RCM catalyst and the product is then cleaved from the solid support to yield a conformationally restricted peptide.

Another approach, disclosed by D. H. Rich in *Protease Inhibitors*, Barrett and Selveson, eds., Elsevier (1986), which is incorporated herein by reference, has been to design peptide mimics through the application of the transition state analogue concept in enzyme inhibitor design. For example, it is known that the secondary alcohol of staline mimics the tetrahedral transition state of the scissile amide bond of the pepsin substrate.

In summary, terminal modifications are useful, as is well known, to reduce susceptibility by proteinase digestion and therefore to prolong the half-life of the peptides in solutions, particularly in biological fluids where proteases may be present. Polypeptide cyclisation is also a useful modification because of the stable structures formed by cyclisation and in view of the biological activities observed for cyclic peptides.

Thus, in one embodiment the polypeptide of the first aspect of the invention is linear. However, in an alternative embodiment, the polypeptide is cyclic.

It will be appreciated by persons skilled in the art that the polypeptides of the invention may be of various lengths. Typically, however, the polypeptide is between 10 and 200 amino acids in length, for example between 10 and 150, 15 and 100, 15 and 50, 20 and 40 or 25 and 35 amino acids in length. For example, the polypeptide may be at least 20 amino acids in length.

In one embodiment, the polypeptide is or comprises a recombinant polypeptide. Suitable methods for the production of such recombinant polypeptides are well known in the art, such as expression in prokaryotic or eukaryotic hosts cells (for example, see Sambrook & Russell, 2000, *Molecular Cloning, A Laboratory Manual*, Third Edition, Cold Spring Harbor, New York, the relevant disclosures in which document are hereby incorporated by reference).

Polypeptides of the invention can also be produced using a commercially available in vitro translation system, such as rabbit reticulocyte lysate or wheatgerm lysate (available from Promega). Preferably, the translation system is rabbit reticulocyte lysate. Conveniently, the translation system may be coupled to a transcription system, such as the TNT transcription-translation system (Promega). This system has the advantage of producing suitable mRNA transcript from an encoding DNA polynucleotide in the same reaction as the translation.

It will be appreciated by persons skilled in the art that polypeptides of the invention may alternatively be synthesised artificially, for example using well known liquid-phase or solid phase synthesis techniques (such as t-Boc or Fmoc solid-phase peptide synthesis). For example, the polypeptides may be synthesized as described in Solid-Phase Peptide Synthesis (1997) Fields, Abelson & Simon (Eds), Academic Press (ISBN: 0-12-182190-0), which is incorporated herein by reference.

Thus, the following related aspects are included within the scope of the present invention.

A second aspect of the invention provides a nucleic acid molecule which encodes a polypeptide according to the first aspect of the invention. In one embodiment the nucleic acid molecule may be isolated.

A third aspect of the invention provides a vector (such as an expression vector) comprising a nucleic acid molecule according to the second aspect of the invention. In one embodiment the vector may be suitable for replication in eukaryotic cells, for example in mammalian cells.

A fourth aspect of the invention provides a host cell comprising a nucleic acid molecule according to the second aspect of the invention or a vector according to the third aspect of the invention. In one embodiment the host cell is recombinant. In one embodiment the host cell is a eukaryotic cell, for example a mammalian cell.

In addition to the transformed host cells themselves, the present invention also contemplates a culture of those cells, preferably a monoclonal (clonally homogeneous) culture, or a culture derived from a monoclonal culture, in a nutrient medium.

A fifth aspect of the invention provides a method of making a polypeptide according to first aspect of the invention comprising culturing a population of host cells according to fourth aspect of the invention under conditions in which said polypeptide is expressed, and isolating the polypeptide therefrom. Methods of cultivating host cells and isolating recombinant proteins are well known in the art.

A sixth aspect of the invention provides a method of making a polypeptide according to the first aspect of the invention comprising liquid-phase or solid-phase synthesis of the polypeptide.

It will be appreciated by persons skilled in the art that the polypeptides of the invention may be formulated for use in clinical and/or veterinary medicine.

Thus, a seventh aspect of the invention provides a pharmaceutical composition comprising a polypeptide according to the first aspect of the invention together with a pharmaceutically acceptable excipient, diluent, carrier, buffer or adjuvant.

As used herein, 'pharmaceutical composition' means a therapeutically effective formulation for use in the treatment or prevention of disorders and conditions associated with microorganisms and microbial infections.

Additional compounds may also be included in the pharmaceutical compositions, such as other peptides, low molecular weight immunomodulating agents, receptor agonists and antagonists, and antimicrobial agents. Other examples include chelating agents such as EDTA, citrate, EGTA or glutathione.

The pharmaceutical compositions may be prepared in a manner known in the art that is sufficiently storage stable and suitable for administration to humans and animals. The pharmaceutical compositions may be lyophilised, e.g.

through freeze drying, spray drying, spray cooling, or through use of particle formation from supercritical particle formation.

By "pharmaceutically acceptable" we mean a non-toxic material that does not decrease the effectiveness of the biological activity of the active ingredients, i.e. the antimicrobial polypeptide(s). Such pharmaceutically acceptable buffers, carriers or excipients are well-known in the art (see Remington's Pharmaceutical Sciences, 18th edition, A. R Gennaro, Ed., Mack Publishing Company (1990) and handbook of Pharmaceutical Excipients, 3rd edition, A. Kibbe, Ed., Pharmaceutical Press (2000), which are incorporated herein by reference).

The term "buffer" is intended to mean an aqueous solution containing an acid-base mixture with the purpose of stabilising pH. Examples of buffers are Trizma, Bicine, Tricine, MOPS, MOPSO, MOBS, Tris, Hepes, HEPBS, MES, phosphate, carbonate, acetate, citrate, glycolate, lactate, borate, ACES, ADA, tartrate, AMP, AMPD, AMPSO, BES, CABS, cacodylate, CHES, DIPSO, EPPS, ethanolamine, glycine, HEPPSO, imidazole, imidazolelactic acid, PIPES, SSC, SSPE, POPSO, TAPS, TABS, TAPSO and TES.

The term "diluent" is intended to mean an aqueous or non-aqueous solution with the purpose of diluting the peptide in the pharmaceutical preparation. The diluent may be one or more of saline, water, polyethylene glycol, propylene glycol, ethanol or oils (such as safflower oil, corn oil, peanut oil, cottonseed oil or sesame oil).

The term "adjuvant" is intended to mean any compound added to the formulation to increase the biological effect of the peptide. The adjuvant may be one or more of colloidal silver, or zinc, copper or silver salts with different anions, for example, but not limited to fluoride, chloride, bromide, iodide, tiocyanate, sulfite, hydroxide, phosphate, carbonate, lactate, glycolate, citrate, borate, tartrate, and acetates of different acyl composition. The adjuvant may also be cationic polymers such as PHMB, cationic cellulose ethers, cationic cellulose esters, deacetylated hyaluronic acid, chitosan, cationic dendrimers, cationic synthetic polymers such as poly(vinyl imidazole), and cationic polypeptides such as polyhistidine, polylysine, polyarginine, and peptides containing these amino acids.

The excipient may be one or more of carbohydrates, polymers, lipids and minerals. Examples of carbohydrates include lactose, sucrose, mannitol, and cyclodextrines, which are added to the composition, e.g., for facilitating lyophilisation. Examples of polymers are starch, cellulose ethers, cellulose, carboxymethylcellulose, hydroxypropylmethyl cellulose, hydroxyethyl cellulose, ethylhydroxyethyl cellulose, ethyl cellulose, methyl cellulose, propyl cellulose, alginates, carageenans, hyaluronic acid and derivatives thereof, polyacrylic acid, polysulphonate, polyethylenglycol/polyethylene oxide, polyethyleneoxide/polypropylene oxide copolymers, polyvinylalcohol/polyvinylacetate of different degree of hydrolysis, poly(lactic acid), poly(glycholic acid) or copolymers thereof with various composition, and polyvinylpyrrolidone, all of different molecular weight, which are added to the composition, e.g. for viscosity control, for achieving bioadhesion, or for protecting the active ingredient (applies to A-C as well) from chemical and proteolytic degradation. Examples of lipids are fatty acids, phospholipids, mono-, di-, and triglycerides, ceramides, sphingolipids and glycolipids, all of different acyl chain length and saturation, egg lecithin, soy lecithin, hydrogenated egg and soy lecithin, which are added to the composition for reasons similar to those for polymers. Examples of minerals are talc, magnesium oxide, zinc oxide and titanium oxide, which are added to the composition to obtain benefits such as reduction of liquid accumulation or advantageous pigment properties.

The pharmaceutical composition may also contain one or more mono- or di-saccharides such as xylitol, sorbitol, mannitol, lactitiol, isomalt, maltitol or xylosides, and/or monoacylglycerols, such as monolaurin. The characteristics of the carrier are dependent on the route of administration. One route of administration is topical administration. For example, for topical administrations, a preferred carrier is an emulsified cream comprising the active peptide, but other common carriers such as certain petrolatum/mineral-based and vegetable-based ointments can be used, as well as polymer gels, liquid crystalline phases and microemulsions.

It will be appreciated that the pharmaceutical compositions may comprise one or more polypeptides of the invention, for example one, two, three or four different peptides. By using a combination of different peptides the antimicrobial effect may be increased.

As discussed above, the polypeptide may be provided as a salt, for example an acid adduct with inorganic acids, such as hydrochloric acid, sulfuric acid, nitric acid, hydrobromic acid, phosphoric acid, perchloric acid, thiocyanic acid, boric acid etc. or with organic acid such as formic acid, acetic acid, haloacetic acid, propionic acid, glycolic acid, citric acid, tartaric acid, succinic acid, gluconic acid, lactic acid, malonic acid, fumaric acid, anthranilic acid, benzoic acid, cinnamic acid, p-toluenesulfonic acid, naphthalenesulfonic acid, sulfanilic acid etc. Inorganic salts such as monovalent sodium, potassium or divalent zinc, magnesium, copper calcium, all with a corresponding anion, may be added to improve the biological activity of the antimicrobial composition.

The pharmaceutical compositions of the invention may also be in the form of a liposome, in which the polypeptide is combined, in addition to other pharmaceutically acceptable carriers, with amphipathic agents such as lipids, which exist in aggregated forms as micelles, insoluble monolayers and liquid crystals. Suitable lipids for liposomal formulation include, without limitation, monoglycerides, diglycerides, sulfatides, lysolecithin, phospholipids, saponin, bile acids, and the like. Suitable lipids also include the lipids above modified by poly(ethylene glycol) in the polar headgroup for prolonging bloodstream circulation time. Preparation of such liposomal formulations is can be found in for example U.S. Pat. No. 4,235,871, which is incorporated herein by reference.

The pharmaceutical compositions of the invention may also be in the form of biodegradable microspheres. Aliphatic polyesters, such as poly(lactic acid) (PLA), poly(glycolic acid) (PGA), copolymers of PLA and PGA (PLGA) or poly(caprolactone) (PCL), and polyanhydrides have been widely used as biodegradable polymers in the production of microshperes. Preparations of such microspheres can be found in U.S. Pat. No. 5,851,451 and in EP 213 303, which are incorporated herein by reference.

The pharmaceutical compositions of the invention may also be formulated with micellar systems formed by surfactants and block copolymers, preferably those containing poly(ethylene oxide) moieties for prolonging bloodstream circulation time.

The pharmaceutical compositions of the invention may also be in the form of polymer gels, where polymers such as starch, cellulose ethers, cellulose, carboxymethylcellulose, hydroxypropylmethyl cellulose, hydroxyethyl cellulose, ethylhydroxyethyl cellulose, ethyl cellulose, methyl cellulose, propyl cellulose, alginates, chitosan, carageenans, hyaluronic acid and derivatives thereof, polyacrylic acid, polyvinyl imidazole, polysulphonate, polyethylenglycol/polyethylene oxide, polyethylene-oxide/polypropylene oxide copolymers, polyvinylalcohol/polyvinylacetate of different degree of hydrolysis, and polyvinylpyrrolidone are used for thickening of the solution containing the peptide. The polymers may also comprise gelatin or collagen.

Alternatively, the polypeptides of the invention may be dissolved in saline, water, polyethylene glycol, propylene glycol, ethanol or oils (such as safflower oil, corn oil, peanut oil, cottonseed oil or sesame oil), tragacanth gum, and/or various buffers.

The pharmaceutical composition may also include ions and a defined pH for potentiation of action of anti-microbial polypeptides.

The above compositions of the invention may be subjected to conventional pharmaceutical operations such as sterilisation and/or may contain conventional adjuvants such as preservatives, stabilisers, wetting agents, emulsifiers, buffers, fillers, etc., e.g., as disclosed elsewhere herein.

It will be appreciated by persons skilled in the art that the pharmaceutical compositions of the invention may be administered locally or systemically. Routes of administration include topical (e.g. ophthalmic), ocular, nasal, pulmonary, buccal, parenteral (intravenous, subcutaneous, and intramuscular), oral, vaginal and rectal. Also administration from implants is possible. Suitable preparation forms are, for example granules, powders, tablets, coated tablets, (micro)capsules, suppositories, syrups, emulsions, microemulsions, defined as optically isotropic thermodynamically stable systems consisting of water, oil and surfactant, liquid crystalline phases, defined as systems characterised by long-range order but short-range disorder (examples include lamellar, hexagonal and cubic phases, either water- or oil continuous), or their dispersed counterparts, gels, ointments, dispersions, suspensions, creams, aerosols, droplets or injectable solution in ampoule form and also preparations with protracted release of active compounds, in whose preparation excipients, diluents, adjuvants or carriers are customarily used as described above. The pharmaceutical composition may also be provided in bandages, plasters or in sutures or the like.

In a particular embodiment, the pharmaceutical composition is suitable for oral administration, parenteral administration or topical administration. For example, the pharmaceutical composition may be suitable for topical administration (e.g. ophthalmic administration, in the form of a spray, lotion, paste or drops etc.).

The pharmaceutical compositions will be administered to a patient in a pharmaceutically effective dose. By "pharmaceutically effective dose" is meant a dose that is sufficient to produce the desired effects in relation to the condition for which it is administered. The exact dose is dependent on the, activity of the compound, manner of administration, nature and severity of the disorder, age and body weight of the patient different doses may be needed. The administration of the dose can be carried out both by single administration in the form of an individual dose unit or else several smaller dose units and also by multiple administrations of subdivided doses at specific intervals.

The pharmaceutical compositions of the invention may be administered alone or in combination with other therapeutic agents, such as additional antibiotic, anti-inflammatory, immunosuppressive, vasoactive and/or antiseptic agents (such as anti-bacterial agents, anti-fungicides, anti-viral agents, and anti-parasitic agents). Examples of suitable additional antibiotic agents include penicillins, cephalosporins, carbacephems, cephamycins, carbapenems, monobactams, aminoglycosides, glycopeptides, quinolones, tetracyclines, macrolides, and fluoroquinolones. Antiseptic agents include iodine, silver, copper, clorhexidine, polyhexanide and other biguanides, chitosan, acetic acid, and hydrogen peroxide. Likewise, the pharmaceutical compositions may also contain anti-inflammatory drugs, such as steroids and macrolactam derivatives.

Such additional therapeutic agents may be incorporated as part of the same pharmaceutical composition or may be administered separately.

It will be appreciated by persons skilled in the art that the polypeptides of the invention, or pharmaceutical compositions thereof, may be applied to medical devices and other products the implantation into or application of which to the human or animal body is associated with the risk of infection by a microbial agent.

Thus, an eighth aspect of the invention provides a medical device, implant, wound care product, or material for use in the same, which is coated, impregnated, admixed or otherwise associated with a pharmaceutical composition according to the seventh aspect of the invention or a polypeptide according to the first aspect of the invention.

Such a medical device, implant, wound care product, or material for use in the same may come into contact with the human body or component thereof (e.g. blood).

In one embodiment, the medical device, implant, wound care product, or material for use in the same is for use in by-pass surgery, extracorporeal circulation, wound care and/or dialysis.

The composition may be coated, painted, sprayed or otherwise applied to or admixed with a suture, prosthesis, implant, wound dressing, catheter, lens, skin graft, skin substitute, fibrin glue or bandage, etc. In so doing, the composition may impart improved antimicrobial or wound healing properties to the device or material.

By "implant", we include:
(a) A catheter (for example, for intravascular or urinary tract use).
(b) A stent (for example, a coronary stent).
(c) A shunt (for example, a cerebrospinal shunt).
(d) An intubating or tracheotomy tube.
(e) An ophthalmic device (for example, contact lenses, scleral buckles and intraocular lenses).
(f) A joint prosthesis (i.e. arthroplasty and implantation of other orthopaedic devices).
(g) An artificial heart valve.
(h) A breast implant.
(i) An implantable drug delivery device (for example, active pumps and passive solid implants).

In one embodiment, the device or material is coated with the pharmaceutical composition of the invention (or the polypeptide component thereof). By 'coated' we mean that the pharmaceutical composition is applied to the surface of the device or material. Thus, the device or material may be painted or sprayed with a solution comprising a pharmaceutical composition of the invention (or polypeptide thereof). Alternatively, the device or material may be dipped in a reservoir of a solution comprising a polypeptide of the invention.

In an alternative embodiment, the device or material is impregnated with a pharmaceutical composition of the invention (or polypeptide thereof). By 'impregnated' we mean that the pharmaceutical composition is incorporated or otherwise mixed with the device or material such that it is distributed throughout.

For example, the device or material may be incubated overnight at 4° C. in a solution comprising a polypeptide of the invention. Alternatively, a pharmaceutical composition of the invention (or polypeptide thereof) may be immobilised on the device or material surface by evaporation or by incubation at room temperature.

In a further alternative embodiment, a polypeptide of the invention is covalently linked to the device or material, e.g. at the external surface of the device or material. Thus, a covalent bond is formed between an appropriate functional group on the polypeptide and a functional group on the device or material. For example, methods for covalent bonding of polypeptides to polymer supports include covalent linking via a diazonium intermediate, by formation of peptide links, by alkylation of phenolic, amine and sulphydryl groups on the binding protein, by using a poly functional intermediate e.g. glutardialdehyde, and other miscellaneous methods e.g. using silylated glass or quartz where the reaction of di- and trialkoxysilanes permits derivatisation of the glass surface with many different functional groups. For details, see Enzyme immobilisation by Griffin, M., Hammonds, E. J. and Leach, C. K. (1993) In *Technological Applications of Biocatalysts* (BIOTOL SERIES), pp. 75-118, Butterworth-Heinemann, incorporated herein by reference. See also the review article entitled 'Biomaterials in Tissue Engineering' by Hubbell, J. A. (1995) *Science* 13:565-576, which is incorporated herein by reference.

In one embodiment, the medical device, implant, wound care product, or material comprises or consists of a polymer. Suitable polymers may be selected from the group consisting of polyesters (e.g. polylactic acid, polyglycolic acid or poly lactic acid-glycolic acid copolymers of various composition), polyorthoesters, polyacetals, polyureas, polycarbonates, polyurethanes, polyamides) and polysaccharide materials (e.g. cross-linked alginates, hyaluronic acid, carageenans, gelatines, starch, cellulose derivatives).

Alternatively, or in addition, the medical device, implant, wound care product, or material may comprise or consists of metals (e.g. titanium, stainless steel, gold, titanium), metal oxides (silicon oxide, titanium oxide) and/or ceramics (apatite, hydroxyapatite).

Such materials may be in the form of macroscopic solids/monoliths, as chemically or physicochemically cross-linked gels, as porous materials, or as particles.

Medical devices, implants, wound care products, and materials of the invention may be made using methods well known in the art.

It will be appreciated that the medical devices, implants, wound care products, and materials of the invention may be used for any of the medical uses disclosed herein.

A ninth aspect of the invention provides a kit comprising a pharmaceutical composition according to the seventh aspect of the invention or a medical device, implant, wound care product, or material for use in the same, according to the eighth aspect of the invention.

A tenth aspect of the invention provides a polypeptide according to the first aspect of the invention, or a nucleic acid molecule according to the second aspect of the invention, or a pharmaceutical composition according to the seventh aspect of the invention for use in medicine.

An eleventh aspect of the invention provides a polypeptide according to the first aspect of the invention, or a nucleic acid molecule according to the second aspect of the invention, or a pharmaceutical composition according to the seventh aspect of the invention are for use in the curative and/or prophylactic treatment of microbial infections.

The term 'prophylactic' is used to encompass the use of a polypeptide or formulation described herein which either prevents or reduces the likelihood of a condition or disease state in a patient or subject.

By "microbial infections" we include infections caused by microorganisms as described above.

For example, in one embodiment the microbial infection to be treated is a bacterial infection.

The microbial infection to be treated may be an acute or a systemic infection.

In one embodiment, the microbial infection is resistant to one or more conventional antibiotic agents (as discussed above).

In one embodiment, the microbial infection to be treated is caused by a microorganism selected from the group consisting of: *Pseudomonas aeruginosa, Staphylococcus aureus, Escherichia coli* and *Streptococcus pyogenes*.

In a further embodiment, the microbial infection is caused by a microorganism selected from the group consisting of: multidrug-resistant *Staphylococcus aureus* (MRSA) (methicillin-resistant *Staphylococcus aureus*) and multidrug-resistant *Pseudomonas aeruginosa* (MRPA).

It will be appreciated by persons skilled in the art that the polypeptides and formulations of the invention may be co-administered in combination with one or more known or conventional agents for the treatment of the particular disease or condition. By 'co-administer' it is meant that the present polypeptides are administered to a patient such that the polypeptides as well as the co-administered compound may be found in the patient's body (e.g. in the bloodstream) at the same time, regardless of when the compounds are actually administered, including simultaneously.

Therefore, in one embodiment the polypeptide, nucleic acid molecule, or pharmaceutical composition is for use in combination with one or more additional antimicrobial agents, such as the conventional antibiotics described above. Alternatively, or in addition, the additional antimicrobial agents may be an antimicrobial polypeptide or protein, such as LL-37 and collagen type VI protein, or for example selected from group consisting of defensins, gramicidin S, magainin, cecropin, histatin, hyphancin, cinnamycin, burforin 1, parasin 1 and protamines, and fragments, variants and fusion thereof which retain, at least in part, the antimicrobial activity of the parent protein.

A twelfth aspect of the invention provides a polypeptide according to the first aspect of the invention or a nucleic acid molecule according to the second aspect of the invention or a pharmaceutical composition according to the seventh aspect of the invention for use in wound care.

By "wound care" we include the treatment of wounds, promoting wound closure, preventing and/or treating wound infection and/or ulcers, wherein the wound may be extracorporeal or intracorporeal. Use in wound care therefore includes polypeptides which are able to aid (for example, accelerate) the wound healing process and/or to prevent infection of the wound. For example, the polypeptides of the invention may be used in a wound care product, such as a cream, gel, ointment, dressing or plaster, which is capable of enhancing epithelial regeneration and/or healing of wound epithelia and/or wound stroma. In one embodiment, the polypeptide is capable of enhancing the proliferation of epithelial and/or stromal cells through a non-lytic mechanism.

It will be appreciated that the polypeptides having wound healing properties may have a primary or ancillary role in the function of the wound care products of the invention.

In one embodiment of the twelfth aspect of the invention, the polypeptide, nucleic acid molecule or pharmaceutical composition is administered in combination with an additional antimicrobial agent, as described above.

A thirteenth aspect of the invention provides use of a peptide or fragment according to the first aspect of the invention, or a nucleic acid molecule to the second aspect of the invention, or a pharmaceutical composition according to the seventh aspect of the invention in the manufacture of a medicament for the treatment of microbial infections, as described above.

A fourteenth aspect of the invention provides use of a peptide or fragment according to the first aspect of the invention, or a nucleic acid molecule to the second aspect of the invention, or a pharmaceutical composition according to the seventh aspect of the invention in the manufacture of a medicament for the treatment of wounds, as described above.

A fifteenth aspect of the invention provides a method of treating an individual with a microbial infection, the method comprising the step of administering to an individual in need thereof an effective amount of a peptide or fragment according to the first aspect of the invention, or a nucleic acid molecule according to the second aspect of the invention, or a pharmaceutical composition according to the seventh aspect of the invention.

A sixteenth aspect of the invention provides a method of treating a wound in an individual, the method comprising the step of administering to an individual in need thereof an effective amount of a polypeptide or fragment according to the first aspect of the invention, or a nucleic acid molecule according to the second aspect of the invention, or a pharmaceutical composition according to the seventh aspect of the invention.

The term 'effective amount' is used herein to describe concentrations or amounts of polypeptides or pharmaceutical compositions according to the present invention which may be used to produce a favourable change in a disease or condition treated, whether that change is a remission, a favourable physiological result, a reversal or attenuation of a disease state or condition treated, the prevention or the reduction in the likelihood of a condition or disease state occurring, depending upon the disease or condition treated. Where polypeptides or pharmaceutical compositions of the invention are used in combination, each of the polypeptides or pharmaceutical compositions may be used in an effective amount, wherein an effective amount may include a synergistic amount.

It will be appreciated by persons skilled in the art that the polypeptides and pharmaceutical formulations of the present invention have utility in both the medical and veterinary fields. Thus, the methods of the invention may be used in the treatment of both human and non-human animals (such as horses, dogs and cats). Preferably, however, the patient is human.

For veterinary use, a compound of the invention is administered as a suitably acceptable formulation in accordance with normal veterinary practice and the veterinary surgeon will determine the dosing regimen and route of administration which will be most appropriate for a particular animal.

A seventeenth aspect of the invention provides a method for killing microorganisms in vitro comprising contacting the microorganisms with a polypeptide according to the first aspect of the invention or a pharmaceutical composition according to the seventh aspect of the invention. For example, the pharmaceutical composition or polypeptide may also be used in the form of a sterilising solution or wash to prevent the growth of microorganisms on a surface or substrate, such as in a clinical environment (e.g. surgical theatre) or a domestic environment (e.g. a kitchen work surface, washing clothes such as bed linen).

In one embodiment the antimicrobial compound may be in solution at a concentration of 1 to 100 µg/ml.

In one embodiment the solution further comprises a surface-active agent or surfactant. Suitable surfactants include anionic surfactants (e.g. an aliphatic sulphonate), amphoteric and/or zwitterionic surfactants (e.g. derivatives of aliphatic quaternary ammonium, phosphonium and sulfonium compounds) and nonionic surfactants (e.g. aliphatic alcohols, acids, amides or alkyl phenols with alkylene oxides)

Conveniently, the surface-active agent is present at a concentration of 0.5 to 5 weight percent.

The sterilising solutions are particularly suited for use in hospital environments. For example, the sterilising solutions may be used to sterilise surgical instruments and surgical theatre surfaces, as well as the hands and gloves of theatre personnel. In addition, the sterilising solutions may be used during surgery, for example to sterilise exposed bones. In all cases, the solution is applied to the surface to be sterilised.

The pharmaceutical composition or polypeptide may also be used to disinfect blood and blood products and in the diagnosis of bacterial contamination or infection.

In both in vitro and in vivo uses, the pharmaceutical composition or polypeptide is preferably exposed to the target microorganisms (or surface/area to be treated) for at least five minutes. For example, the exposure time may be at least 10 minutes, 20 minutes, 30 minutes, 40 minutes, 50 minutes, 1 hour, 2 hours, 3, hours, 5 hours, 12 hours and 24 hours.

The listing or discussion of an apparently prior-published document in this specification should not necessarily be taken as an acknowledgement that the document is part of the state of the art or is common general knowledge.

Preferred, non-limiting examples which embody certain aspects of the invention will now be described, with reference to the following figures:

FIGS. 1A-1D. Antibacterial effect of collagen type VI against different strains of Gram-positive and Gram-negative bacteria. (FIG. 1A) S. pyogenes, S. aureus, E. coli or P. aeruginosa ($2\times10^6$ cfu/ml) were incubated with collagen type VI (2 µM) for 2 h at 37° C. with 5% $CO_2$. Bacteria incubated with Tris-HCl/glucose; pH 7.4 buffer or with LL-37 served as negative or positive controls, respectively. (FIG. 1B) For visualization of antimicrobial activities, bacteria ($2\times10^9$ cfu/ml) were treated with collagen type VI (2 µM) for 2 h at 37° C. and subsequently subjected to scanning electron microscopy. Extensive membrane damage, blebbing and ejection of cytoplasmic components were observed in the presence of collagen type VI (right panel) compared to untreated bacteria (left panel). The scale bar represents 2 µm (S. pyogenes, S. aureus) and 1 µm (P. aeruginosa, E. coli), respectively. (FIG. 1C) Kinetics studies of bacterial membrane disruption induced by collagen type VI. S. pyogenes and P. aeruginosa (green pseudocolor) were treated with collagen type VI (2 µM) for 0, 30, 60 and 120 min at 37° C. and visualized with scanning electron microscopy. Arrowheads show membrane blebbing. Cytoplasmic exudates are indicated in purple pseudocolor. Scale bar=1 µm. (FIG. 1D) For fluorescence microscopy analysis, bacteria were treated with collagen type VI as described above and permeabilization was assessed by using the impermeant probe FITC (lower panels). Same positions were visualized with light microscopy (upper panels). 3 µM of LL-37 were used as a positive control for membrane damage and bacteria only with buffer was used as negative control. Green color indicates bacterial lysis. Images were taken at 1000× magnification.

FIGS. 2A-2D. (FIG. 2A) Schematic diagram of collagen type VI domain structures. Collagen type VI consists of three α-chains, namely α1(VI), α2(VI) and α3(VI). The N- and C-terminal globular domains of collagen type VI are numbered as described previously (51). The brackets indicate the region where the recombinant fragments were expressed. (FIG. 2B) Heparin-binding activity of recombinant globular domains of collagen type VI was determined by slot blot using biotinylated heparin. Recombinantly expressed fragments of α1(VI), α2(VI) or α3(VI) chain (10 µg) showed binding to heparin. LL-37 (5 µg) was used as a positive control (right panel). Unlabeled heparin (6 mg/ml) inhibited the binding of biotinylated heparin to the recombinant fragments and LL-37 (left panel). (FIG. 2C) Binding of recombinant fragments to S. pyogenes was visualized by negative staining and transmission electron microscopy using colloidal gold labeling. Recombinant fragments at final concentration of 2 µM displayed binding to bacterial membrane (upper panel). Upon pre-incubation with unlabeled heparin recombinant fragments did not bind to bacterial membrane (lower panel). The scale bar represents 100 nm. (FIG. 2D) The amounts of recombinant fragments bound to the bacterial surface in the absence (−) or presence (+) of heparin were calculated as gold label per µm² bacterial surface.

Figure 3A:
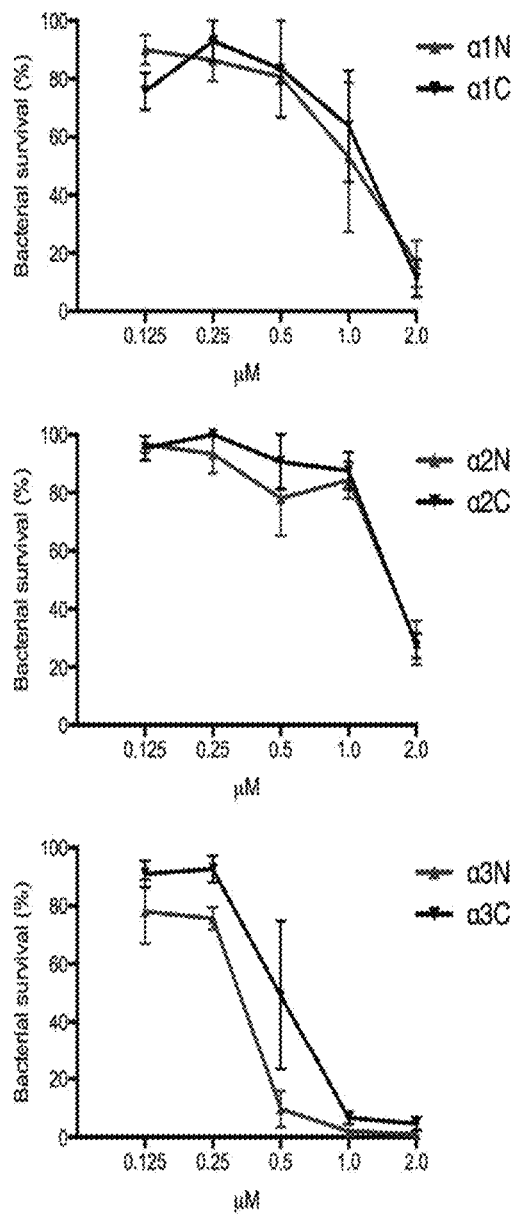
Figure 3B:
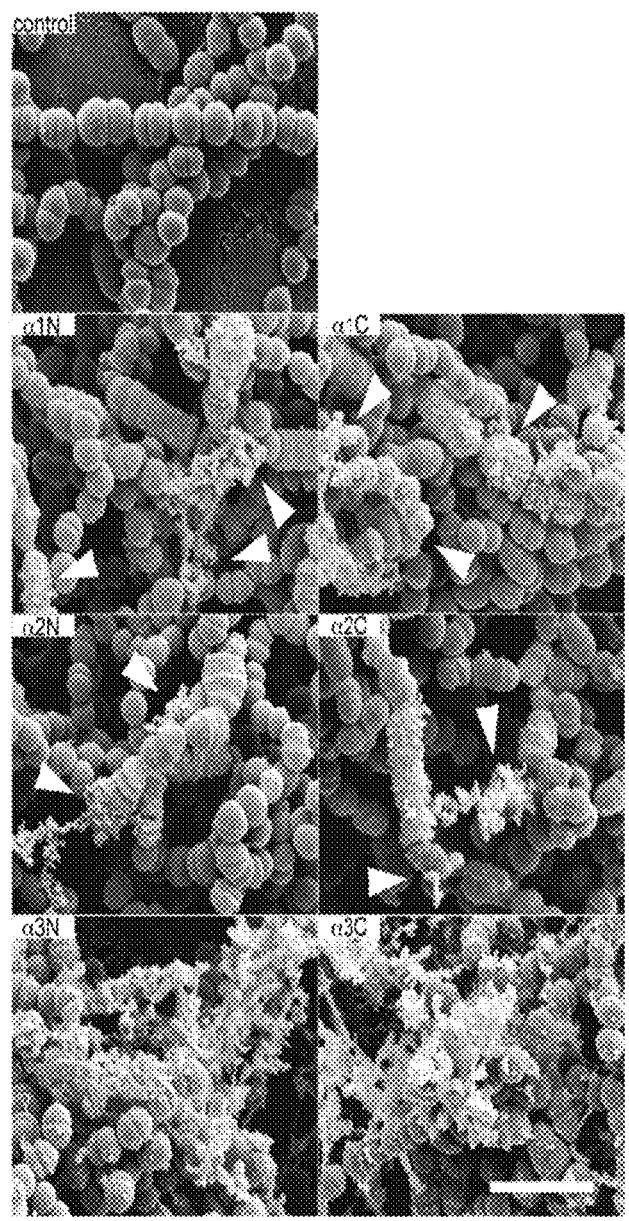

FIGS. 3A-3B. Dose-dependent killing of S. pyogenes by recombinant globular domains of collagen type VI. (FIG. 3A) Bacteria (2×10⁶ cfu/ml) were incubated with recombinant fragments at the concentrations indicated for 2 h at 37° C. with 5% $CO_2$. (FIG. 3B) Recombinant globular domains of collagen type VI induce membrane disruption. Bacteria (2×10⁹ cfu/ml) were treated with recombinant fragments and permeabilization was visualized by using scanning electron microscopy. Extensive membrane disruption and leakage of intracellular contents are observed in the presence of these proteins and are indicated with arrowheads. The data shown are representative of at least three independent experiments and mean values are presented. The scale bar represents 5 µm.

Figure 4:
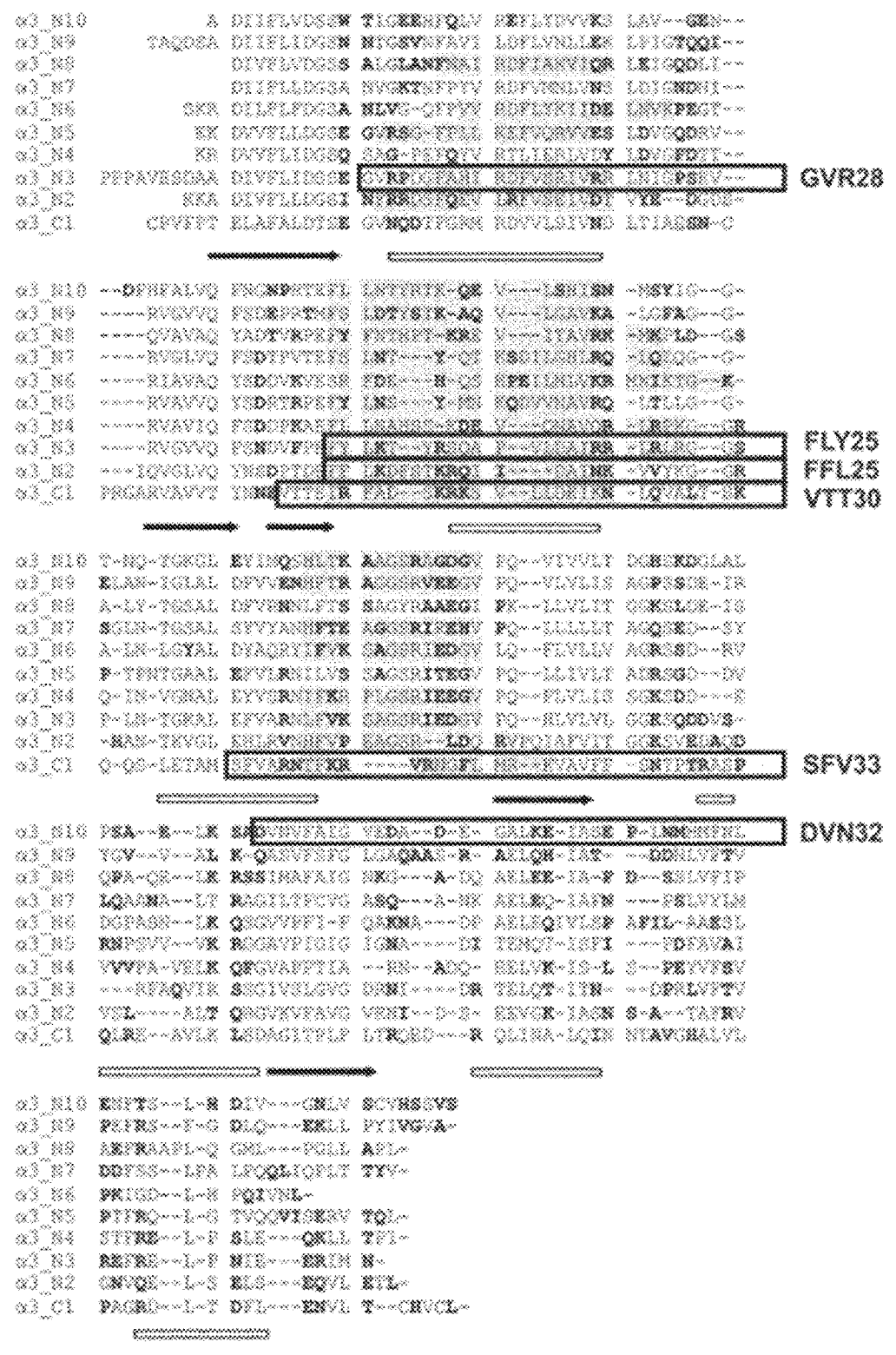

FIG. 4. Structural alignment of VWA domains in human collagen type VI α3-chain generated by structural superimposition of the VWA domain models. Underneath the sequence, α-helices and β-strands are indicated with rectangular boxes and black arrows, respectively. The exposed amino acids are denoted in bold letters and cationic stretches are highlighted in grey. The rectangular boxes in the sequence indicate the location of the cationic peptides as well as the control peptide (DVN32). Sequence identifiers: α3_N10 [SEQ ID NO:37], α3_N9 [SEQ ID NO:38], α3_N8 [SEQ ID NO:39], α3_N7 [SEQ ID NO:40], α3_N6 [SEQ ID NO:41], α3_N5 [SEQ ID NO:42], α3_N4 [SEQ ID NO:43], α3_N3 [SEQ ID NO:44], α3_N2 [SEQ ID NO:45], α3_C1 [SEQ ID NO:46], FIGS. 5A-5C. (FIG. 5A) Surface representation of VWA domains of α3(VI) chain show the electrostatic properties (black=positive charge; grey=negative charge). (FIG. 5B) The ribbon diagrams show the location of the cationic peptides and the negative control peptide (DVN32). (FIG. 5C) The biophysical properties of the peptides (GVR28 [SEQ ID NO: 1], FYL25 [SEQ ID NO: 2], FFL25 [SEQ ID NO: 3], VTT30 [SEQ ID NO: 4], SFV33 [SEQ ID NO: 5] and DVN32 [SEQ ID NO: 6]). [a]Peptides are identified by their first three $NH_2$-terminal residues using the single-letter code, followed by the total number of residues constituting the peptide. [b]Sequences of peptides are given in single-letter code. [c]pI: theoretical isoelectric point calculated by using the Protparam tool available at us.expasy.org/tools/protparam.html.

Figure 6A:
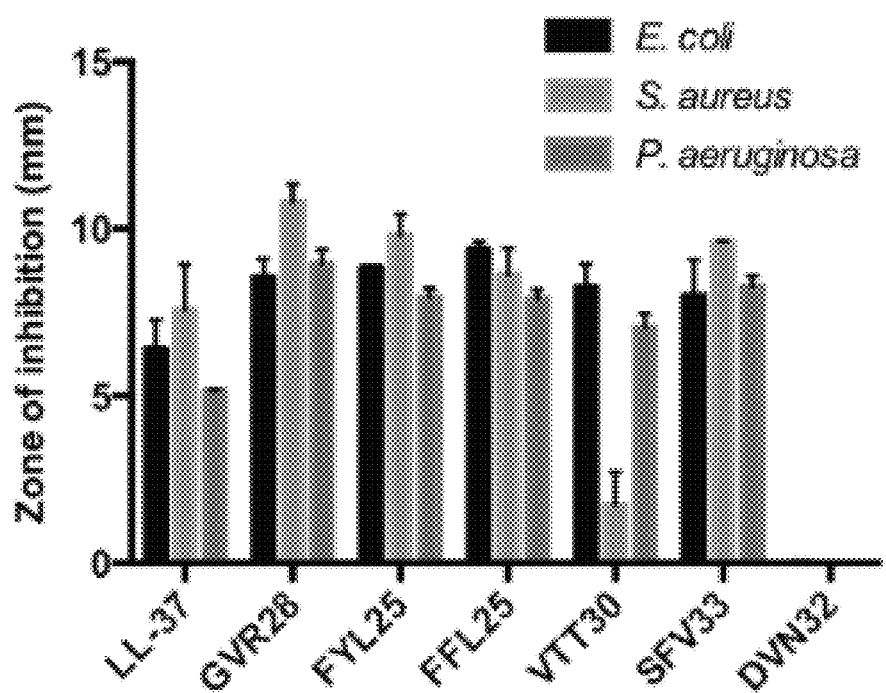
Figure 6B:
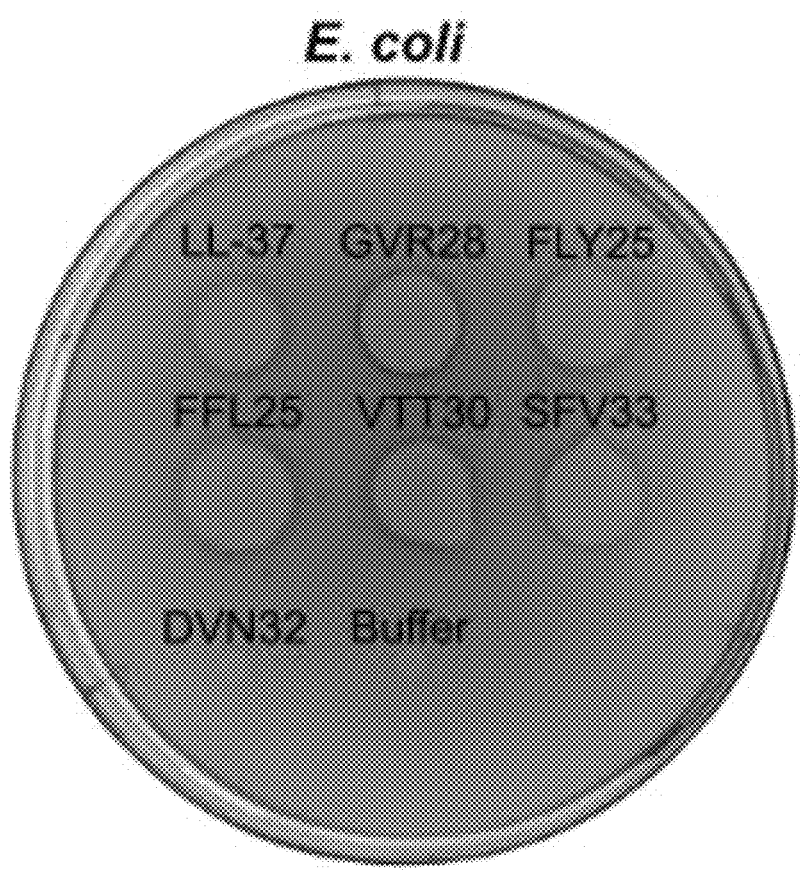
Figure 6C:
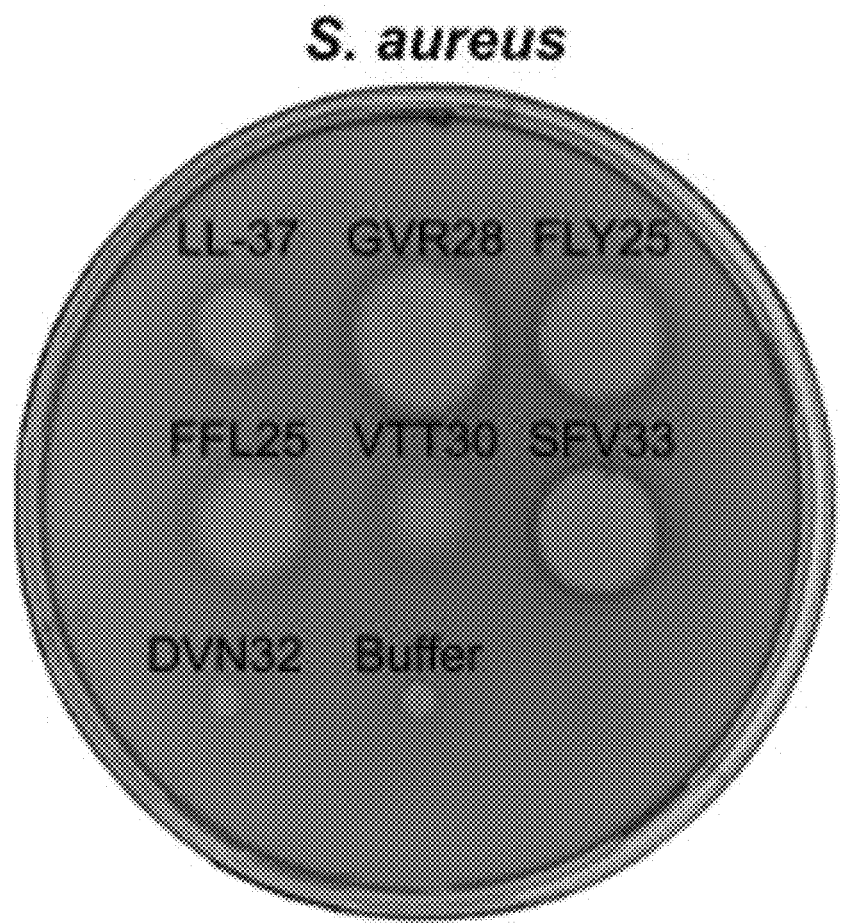

FIGS. 6A-6C. Antibacterial activity of peptides derived from α3(VI) chain. (FIG. 6A) For determination of antibacterial activities, the indicated bacterial isolates (4×10⁶ cfu) were inoculated in agarose gel and loaded with peptides (at 100 µM). LL-37 and Tris-HCl; pH 7.4 buffer were used as a positive and negative control, respectively. The clearance zones correspond to the inhibitory effect of each peptide after incubation at 37° C. for 18-24 h. A representative view of a RDA gel is shown for E. coli (FIG. 6B) and S. aureus (FIG. 6C) with indicated peptides.

Figure 7A:
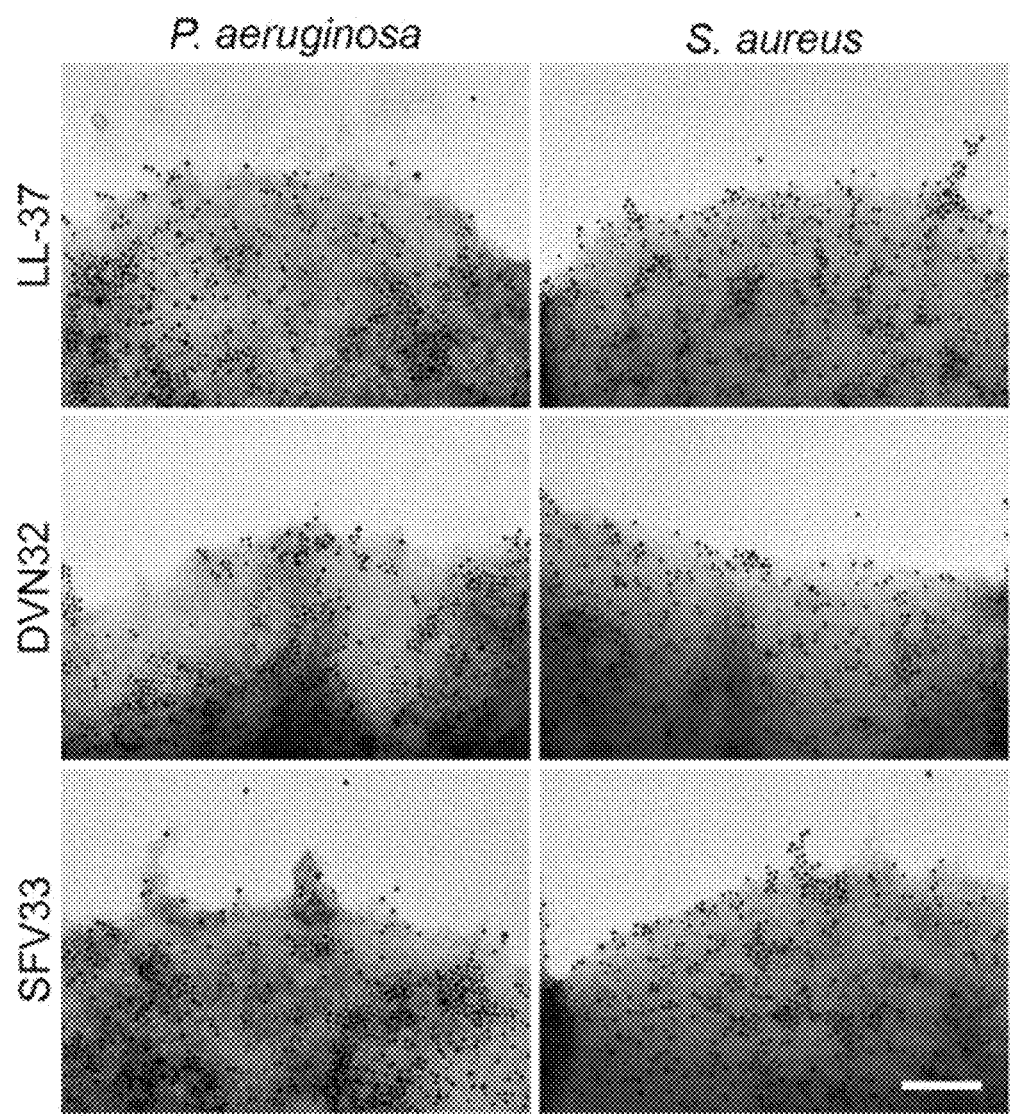
Figure 7B:
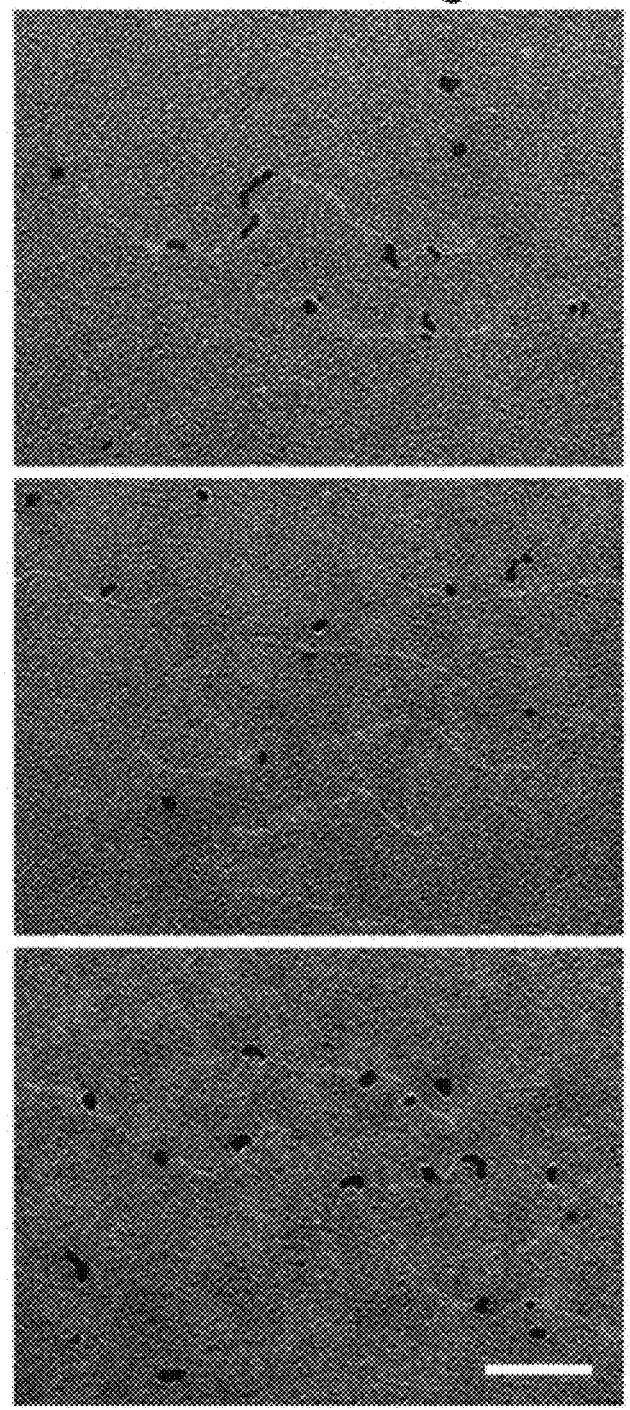
Figure 7C:
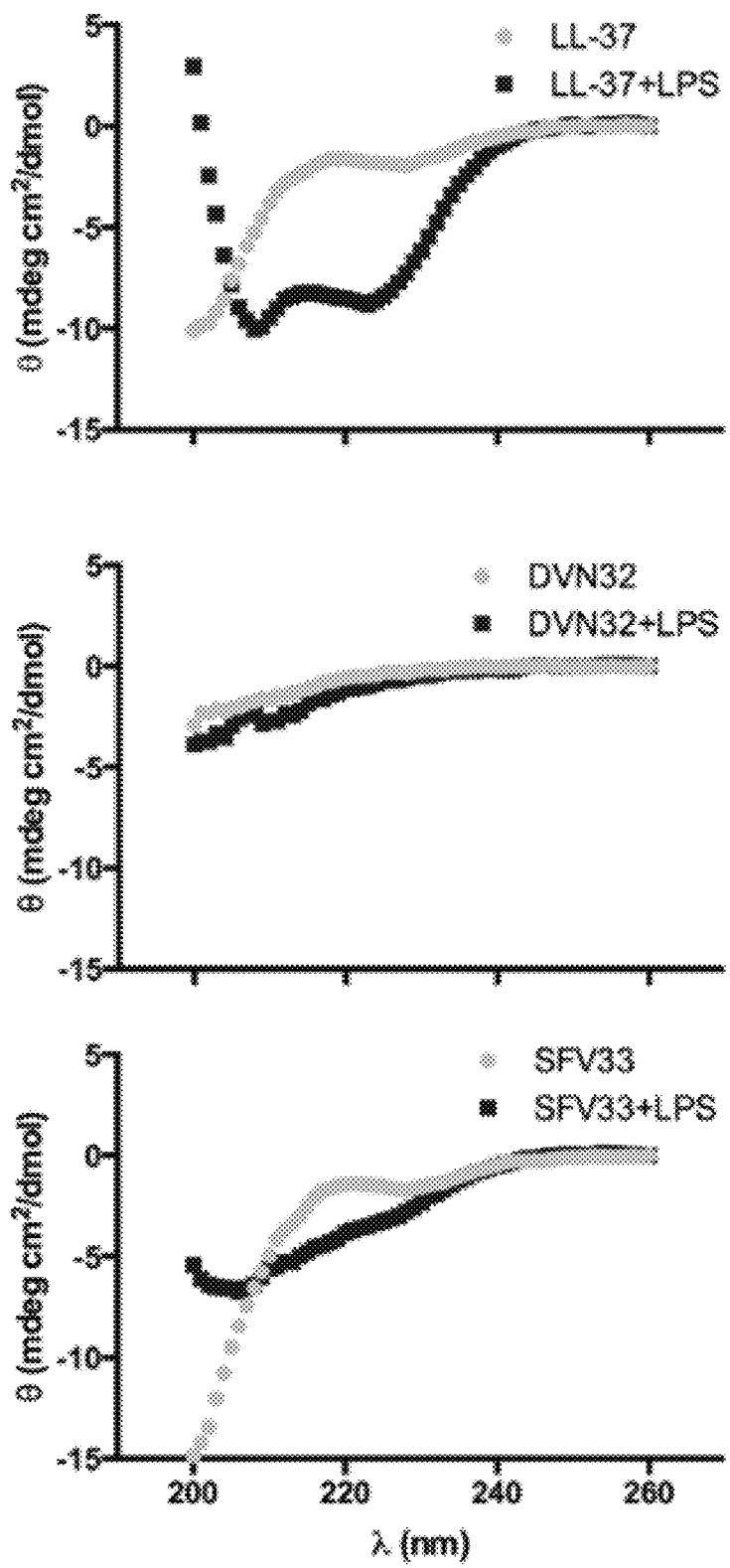
Figure 8A:
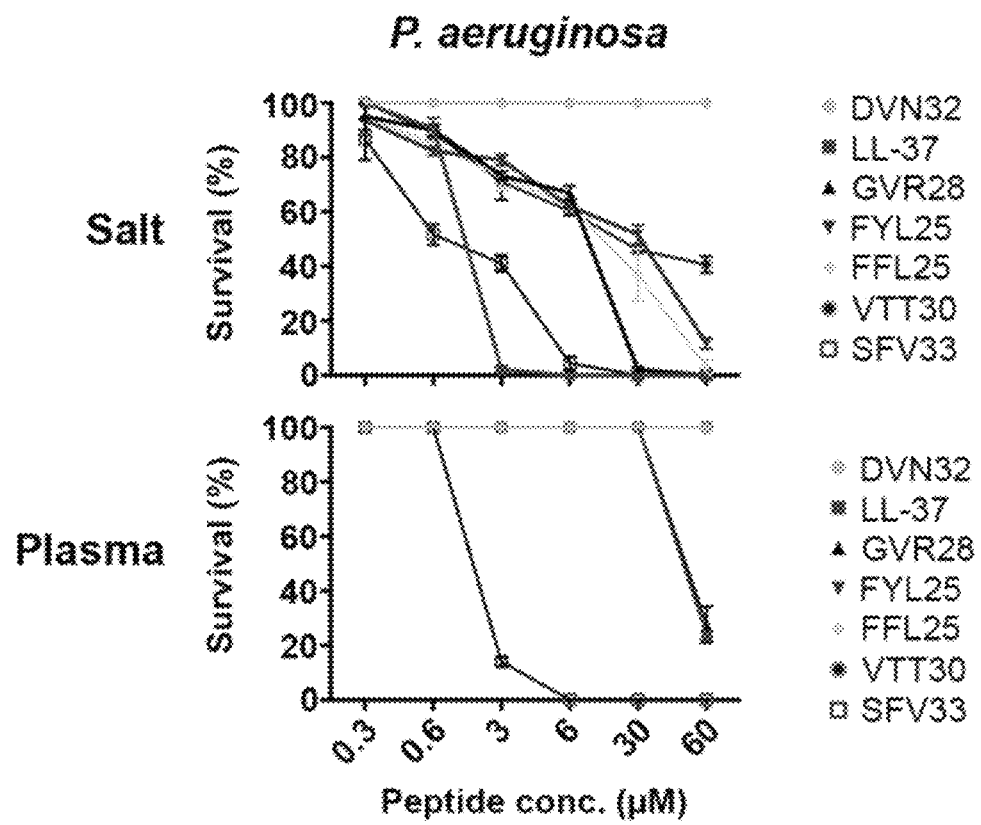
Figure 8B:
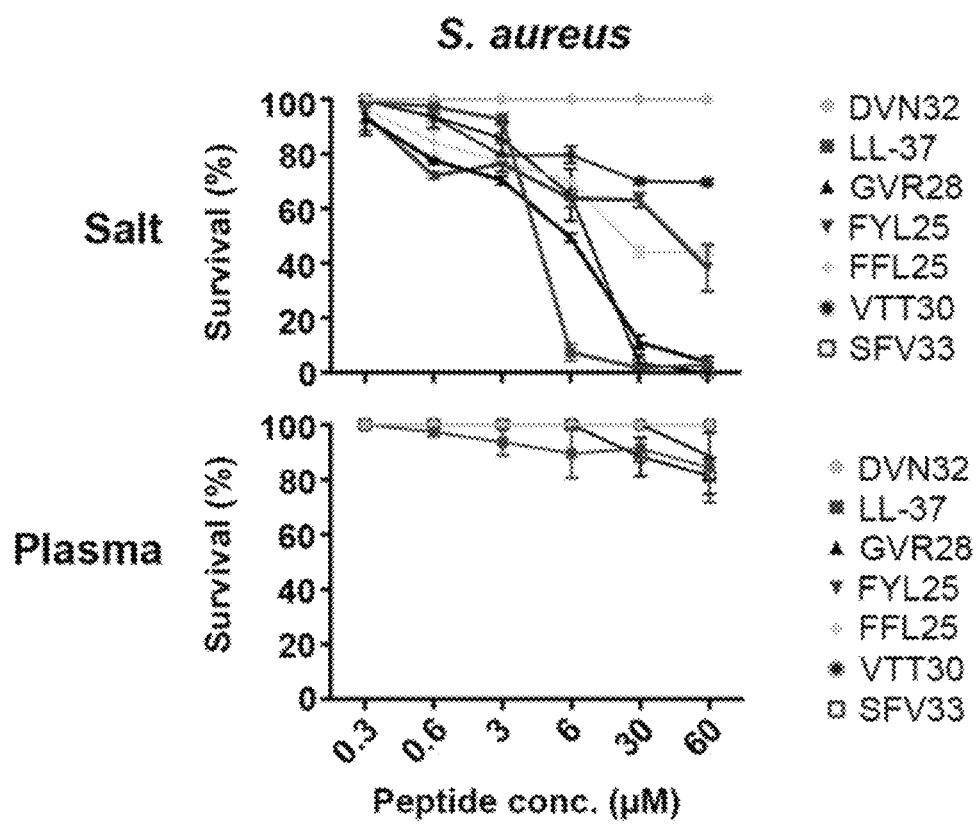
Figure 8C:
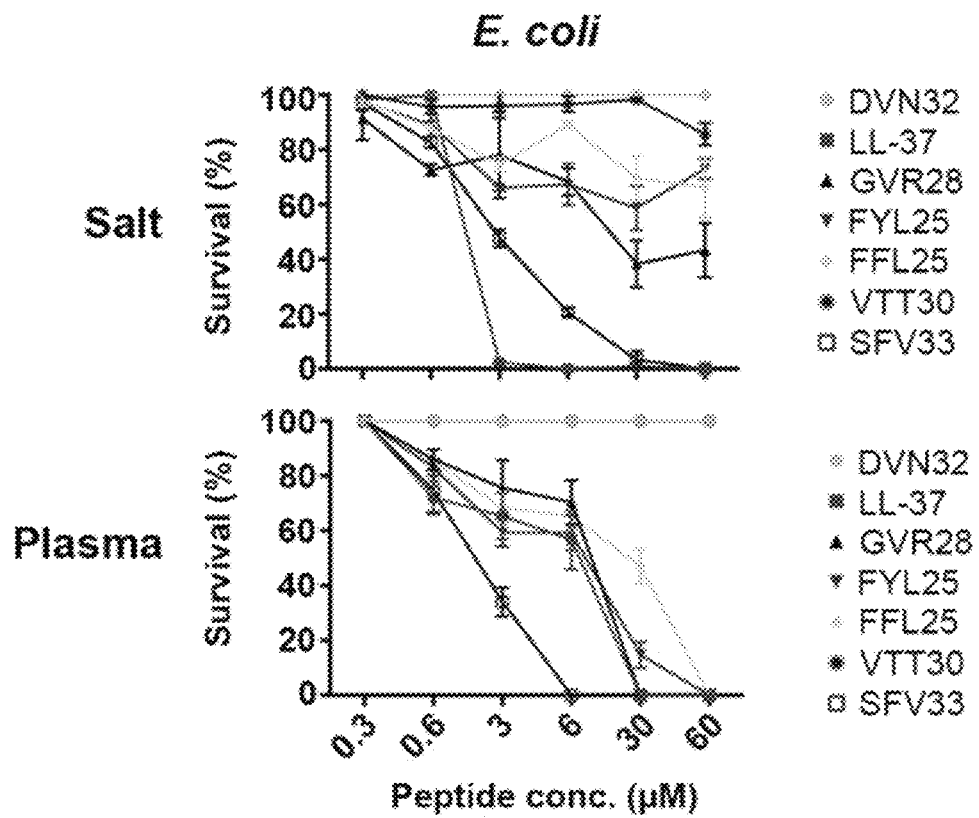
Figure 8D:
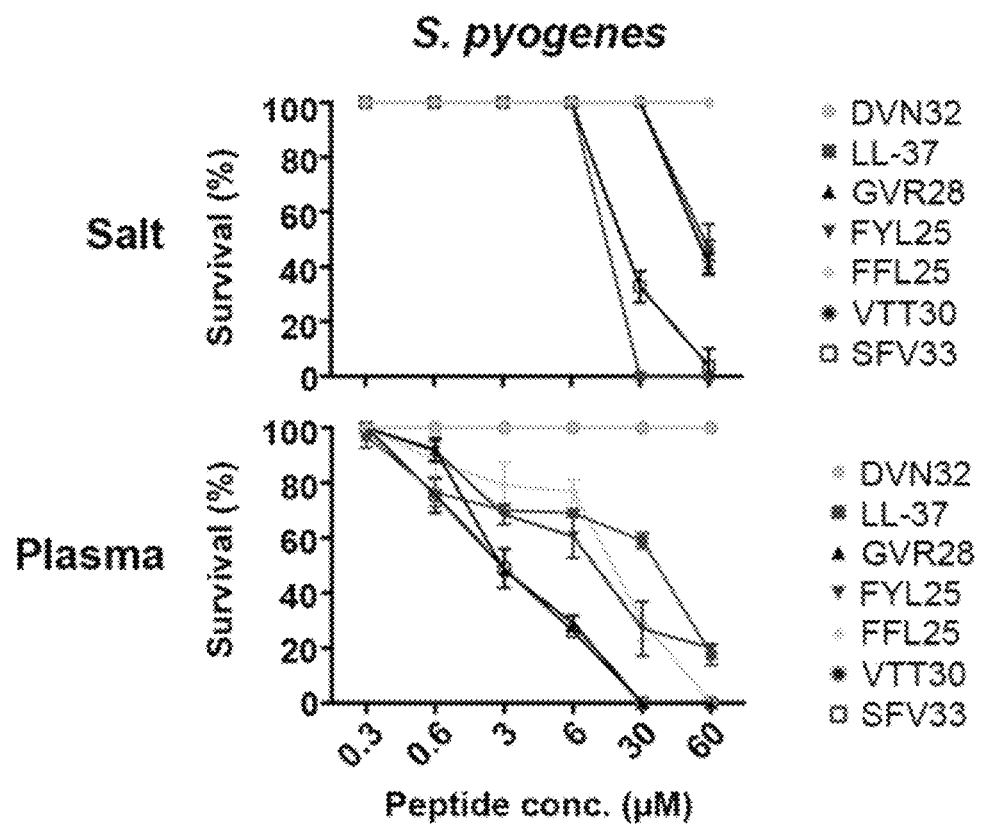

FIGS. 7A-7C. Collagen type VI-derived peptides bind to bacterial surfaces. (FIG. 7A) Binding of collagen type VI-derived peptides to P. aeruginosa, S. aureus or LPS was visualized by negative staining and transmission electron microscopy using colloidal gold labeling. P. aeruginosa or S. aureus (2×10⁹ cfu/ml) were incubated with LL-37, DVN32 or SFV33 conjugated with 10 nm colloidal gold (see Table 2) for 2 h at 37° C. with 5% CO2. Scale bar=100 nm. Peptides are shown as black dots (FIG. 7B) For LPS binding, LL-37, DVN32, and SFV33 conjugated with 10 nm colloidal gold were incubated with LPS (10 µg/ml) for 1 h at 37° C. with 5% $CO_2$. Scale bar=50 nm. Peptides are shown as black dots. (FIG. 7C) CD spectra of LL-37, DVN32 and SFV33 in the presence or absence of LPS (0.2 mg/ml). The peptide concentration was 30 µM.

FIGS. 8A-8D. Antibacterial activities of collagen type VI-derived peptides in the presence of salt and plasma. In viable count assays, antibacterial activity were seen for collagen type VI-derived peptides against P. aeruginosa (FIG. 8A), S. aureus (FIG. 8B), E. coli (FIG. 8C) and S. pyogenes (FIG. 8D), 2×10⁷ cfu/ml bacteria were incubated with collagen type VI-derived peptides (0.3, 0.6, 3, 6, 30 and 60 µM) in the presence of salt buffer (10 mM Tris-HCl, 150 mM NaCl and 5 mM glucose; pH 7.4) with or without 20% human plasma for 2 h at 37° C. with 5% $CO_2$. Bacteria incubated with only salt buffer with or without 20% human plasma served as a negative control. Samples with LL-37 served as positive controls. The data shown are representative of at least three independent experiments and mean values are presented.

Figure 9A:
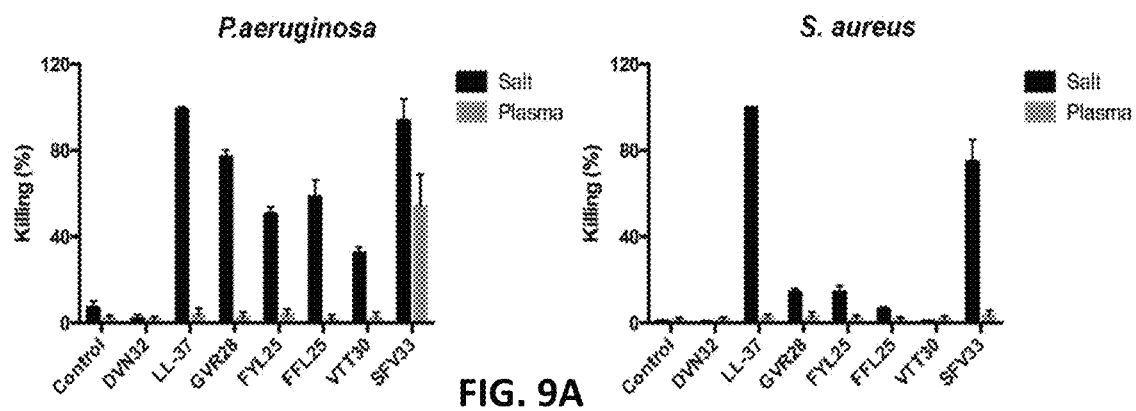
Figure 9B:
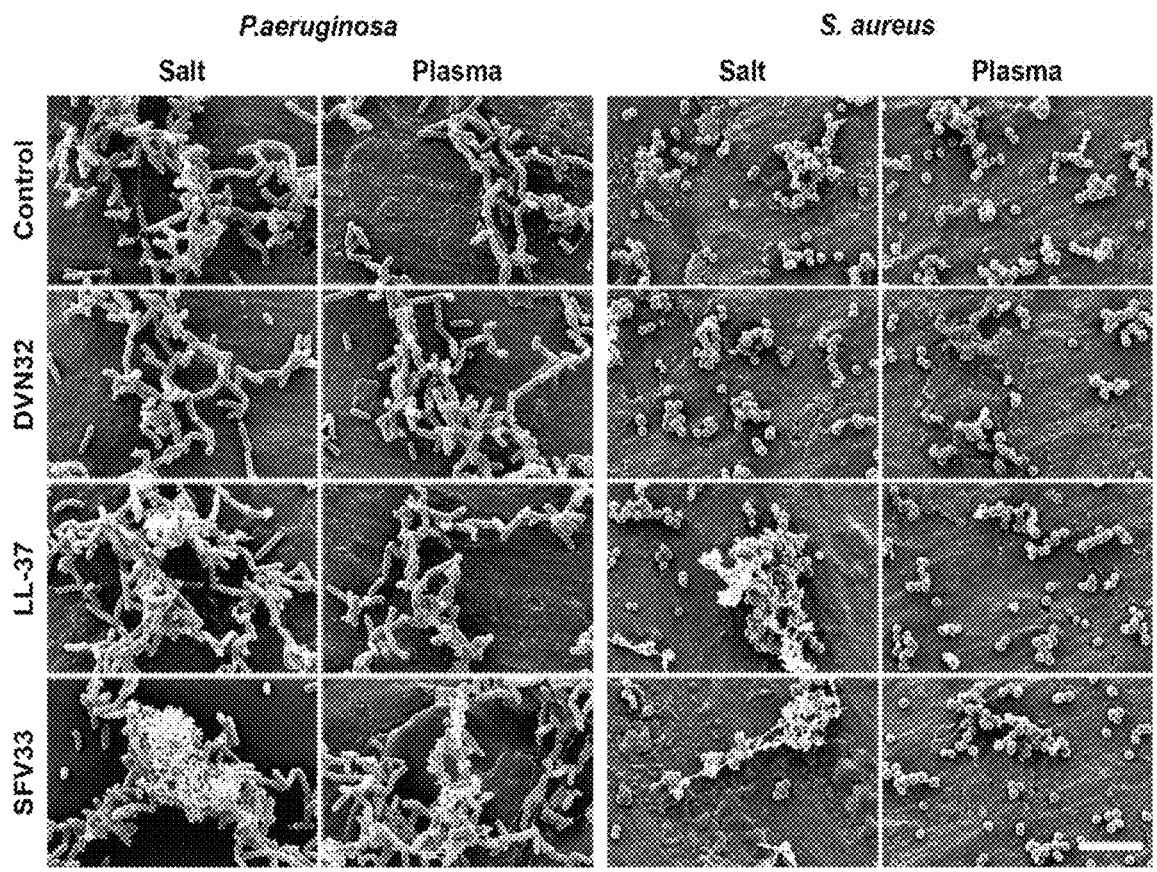

FIGS. 9A-9B. Permeabilization of the cytoplasmic membrane by collagen type VI-derived peptides. (FIG. 9A) P. aeruginosa or S. aureus (2×10⁷ cfu/ml) were subjected to collagen type VI-derived peptides in salt buffer (10 mM Tris-HCl, 150 mM NaCl and 5 mM glucose; pH 7.4) in the presence or absence of 20% human plasma. Propidium iodide (PI) dye was added to the samples and incubated for 30 min on ice in darkness. The mixture was subjected to FACS analysis using a flow cytometry. Identical buffers without peptides were used as controls. As a positive control, bacteria treated with 70% ethanol were used. Each experiment was done in triplicate, and the values represent means±standard deviations. (FIG. 9B) For visualization of antimicrobial activities, bacteria (2×10⁹ cfu/ml) were treated with LL-37, DVN32 and SFV33 (30 µM) in the presence of salt buffer with or without 20% plasma for 2 h at 37° C. and subsequently subjected to scanning electron microscopy. Extensive membrane damage, blebbing and ejection of cytoplasmic components were observed for LL-37 in salt and SFV33 in salt and plasma conditions. Bacteria treated with salt buffer, plasma or DVN32 showed no effects. The scale bar represents 5 µm.

Figures 10A, 10B:
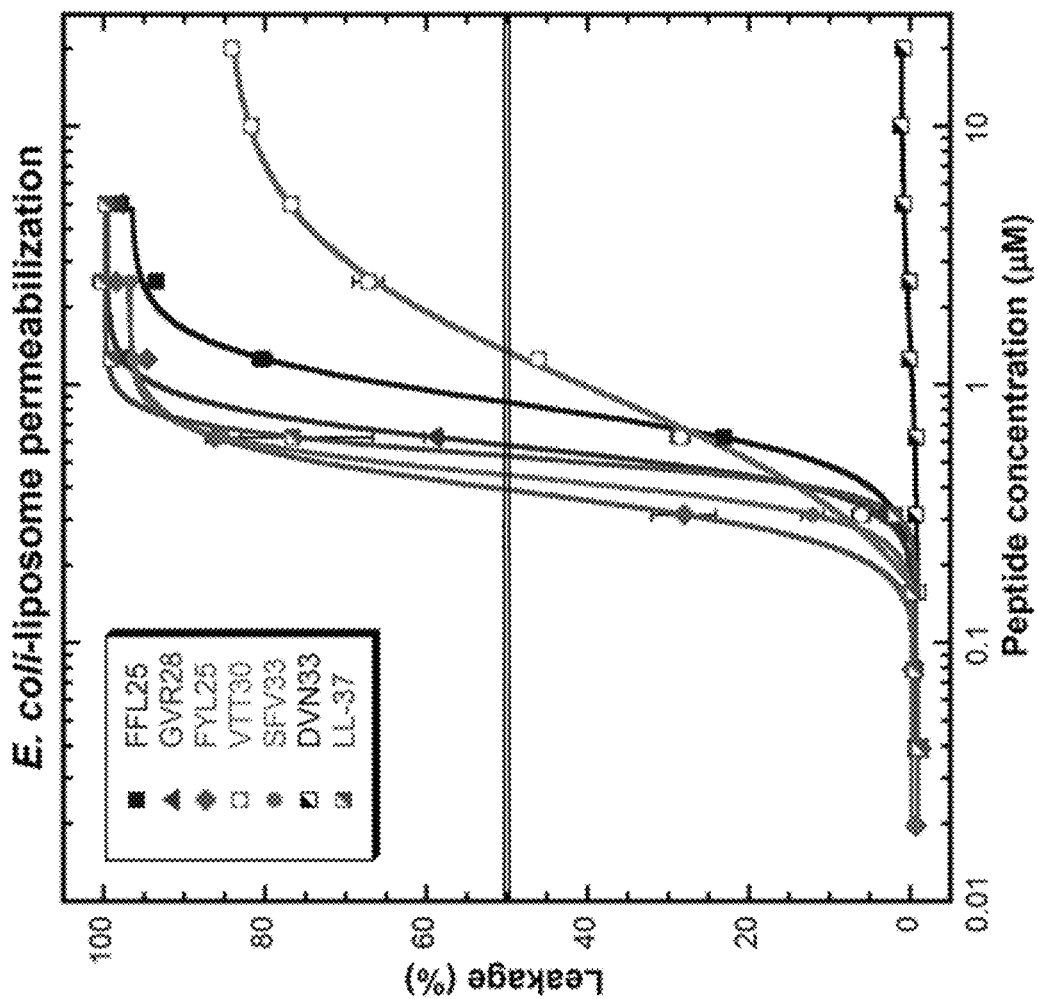

FIGS. 10A-10B. Membrane leakage levels as a function of peptide concentration. (FIG. 10A) The levels of carboxyfluorescein efflux after 45 min of incubation for liposomes composed of E. coli polar lipid extract. Each marker represents the mean leakage at 37° C. in 10 mM Tris buffer (pH 7.4) with standard deviation from triplicate experiments done at individual peptide concentrations, i.e. no cumulative additions. The curve fitting is done by sigmoidal dose-response curve fitting and the $EC_{50}$ level is highlighted with a double line. As a positive control LL-37 was used. (FIG. 10B) $EC_{50}$ values (μM) were calculated for collagen type VI-derived peptides and LL-37.

FIGS. 11A-11B. Cytotoxicity assay of collagen type VI-derived peptides. (FIG. 11A) The hemolytic activity of collagen type VI-derived peptides and LL-37 was monitored by incubating 30 or 60 μM of the peptides with human blood followed by measuring the absorbance at 540 nm. Results are expressed as % of Triton X-100 induced-hemolysis. (FIG. 11B) Serial dilutions of collagen-VI peptides and LL-37 were added to THP1 cells and cell permeabilization was measured by determining the release of LDH. All experiments were performed in triplicates.

Figure 12:
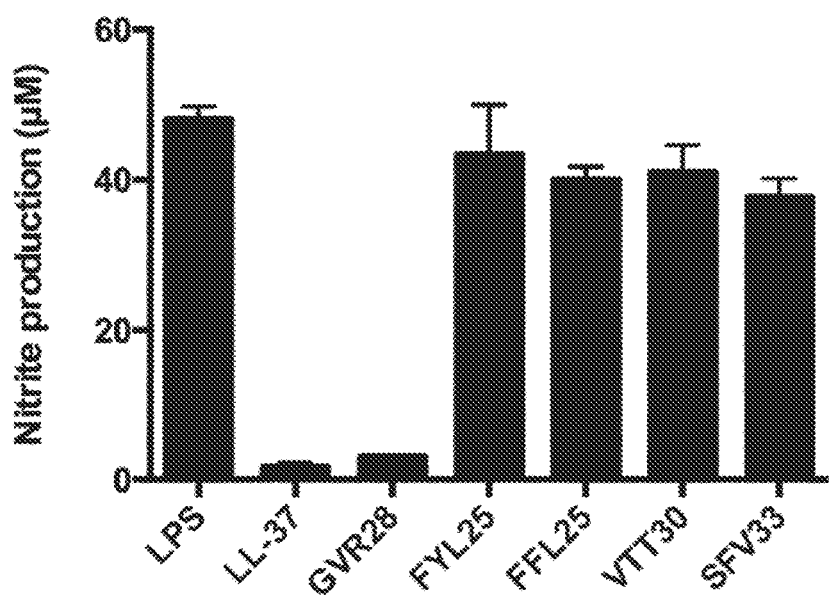

FIG. 12. Anti-endotoxin activity of the peptides. Collagen type VI-derived peptides or LL-37 were pre-treated with LPS (10 ng/ml) for 20 min at RT. The mixture was subsequently added to RAW 264.7 macrophage cells and incubated for 24 h at 37° C. Nitrite levels in the supernatant was determined using Griess reagent. Data are expressed as percentage of nitrite accumulation in cells activated with LPS (100%) and show means±SEM of three independent experiments performed in triplicates.

Figure 13:
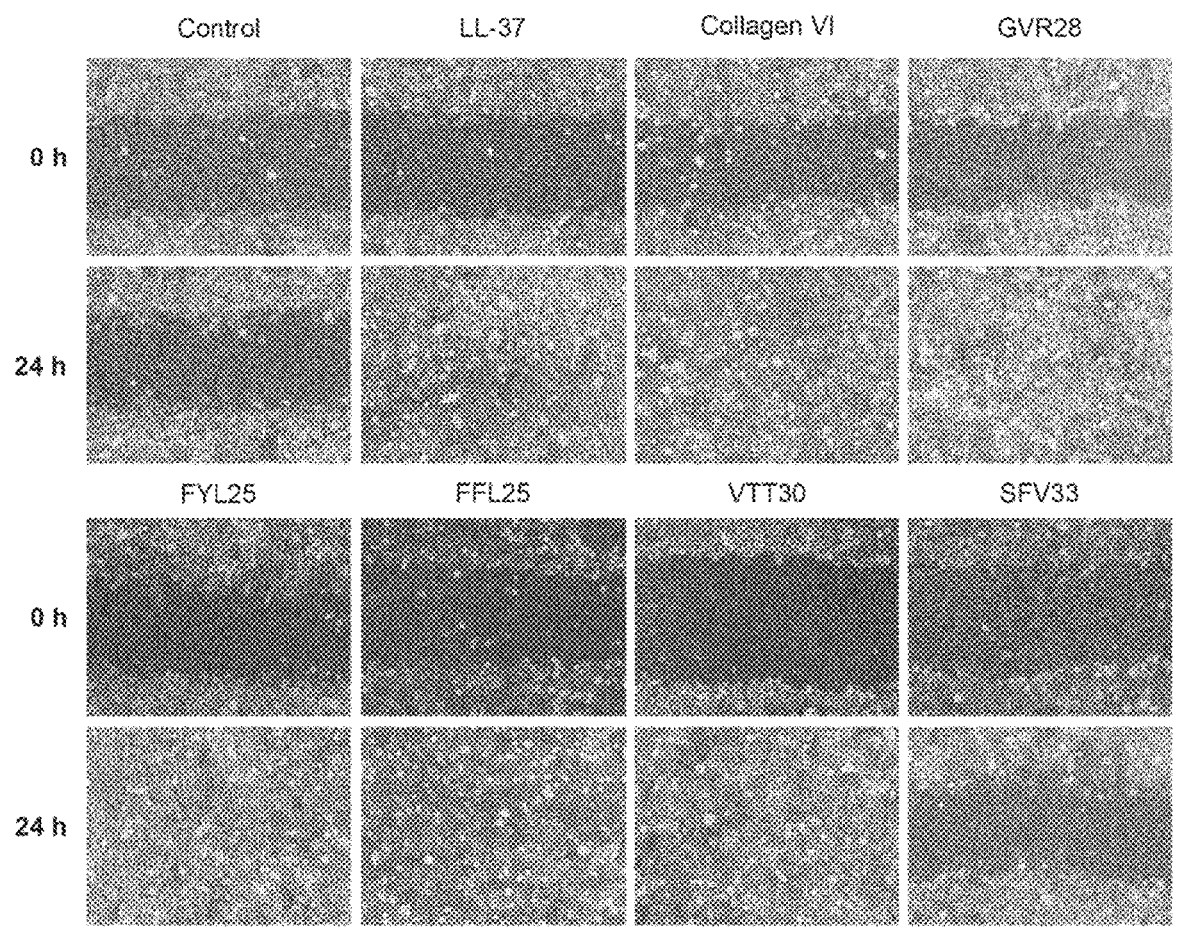

FIG. 13. Collagen type VI-derived peptides promote wound healing. HaCaT cells were cultured in 24-well plate and grown to confluency. Cells were serum starved for 24 h followed by manual scratch with a sterile pipette tip to introduce wound and was washed twice to remove detached cells. Cells were treated with collagen type VI (10 μg/ml), collagen type VI-derived peptides (10 μg/ml) or LL-37 (10 μg/ml) for up to 24 h at 37° C. and 5% $CO_2$ in the absence of serum. Cells were photographed at the time of wound 0 h and examined for cell migration 24 h from peptide addition. The control consisted of cells treated with medium without supplement. Images were taken at 100× magnification. The data shown are representative of at least three independent experiments.

Figure 14A:
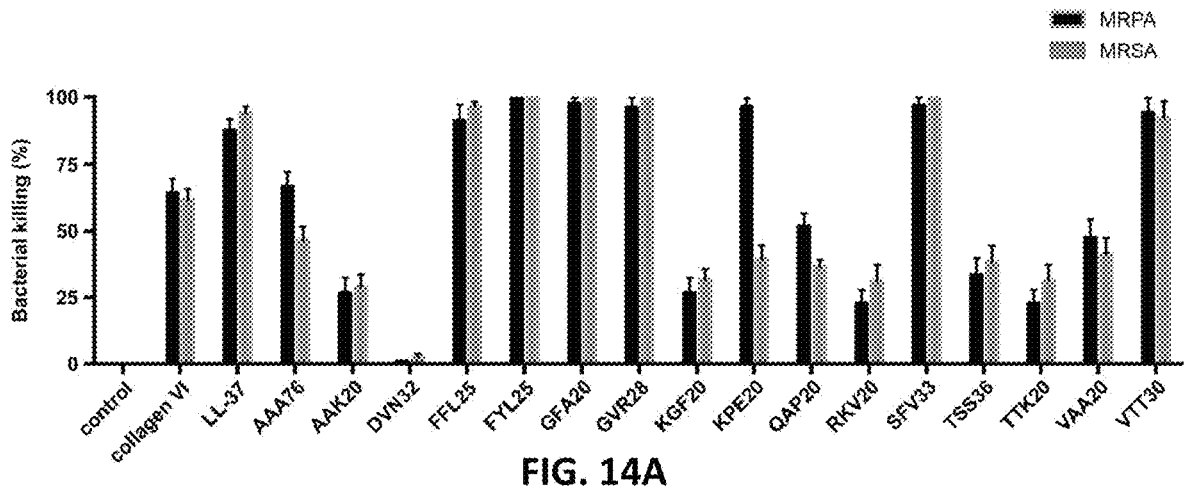
Figure 14B:
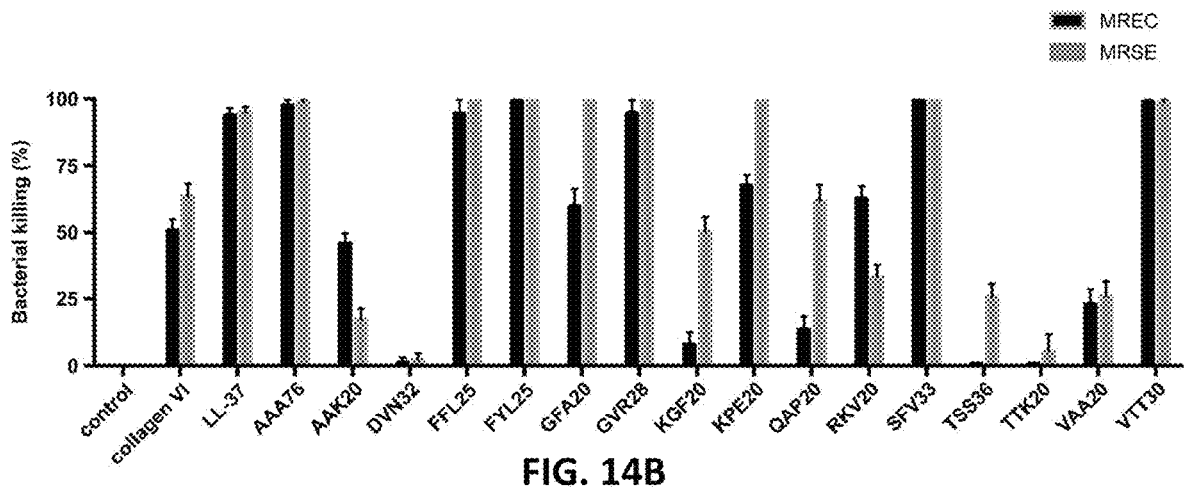
Figure 14C:
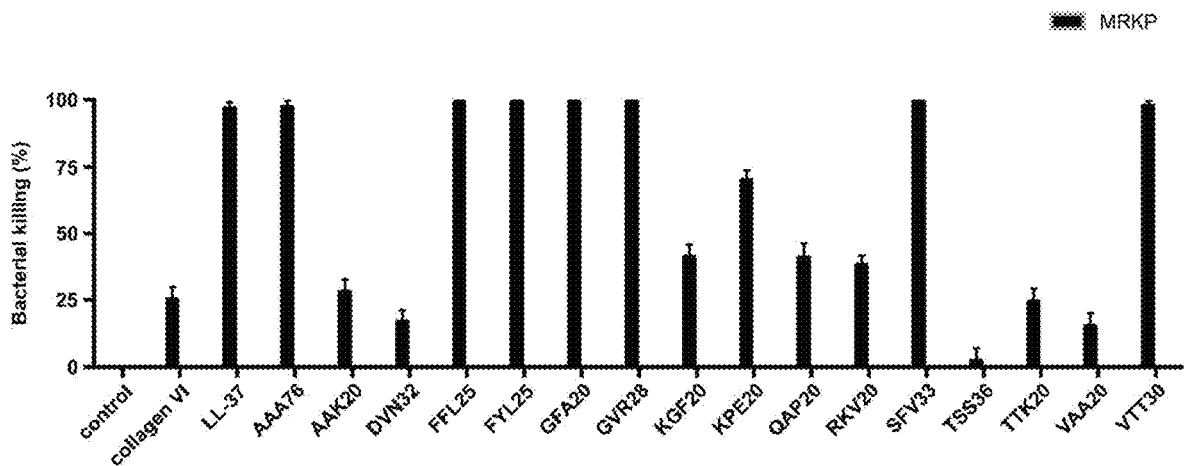

FIGS. 14A-14C. Antibacterial activities of collagen type VI-derived peptides against multidrug-resistant microorganisms. In viable count assays, antibacterial activity was found for collagen type VI-derived peptides against multidrug-resistant Pseudomonas aeruginosa (MRPA) and multidrug-resistant Staphylococcus aureus (MRSA) (FIG. 14A), as well as for collagen type VI-derived peptides against multidrug-resistant Escherichia coli (MREC) and multidrug-resistant Staphylococcus epidermidis (MRSE) (FIG. 14B), and for collagen type VI-derived peptides against multidrug-resistant Klebsiella pneumoniae (MRKP) (FIG. 14C). $2\times10^7$ cfu/ml bacteria were incubated with collagen type VI-derived peptides (30 μM) in the presence of salt buffer (10 mM Tris-HCl, 150 mM NaCl and 5 mM glucose; pH 7.4). Bacteria incubated with only salt buffer served as a control. Samples with LL-37 served as positive controls. The data shown are representative of at least three independent experiments and mean values are presented.

Figure 15:
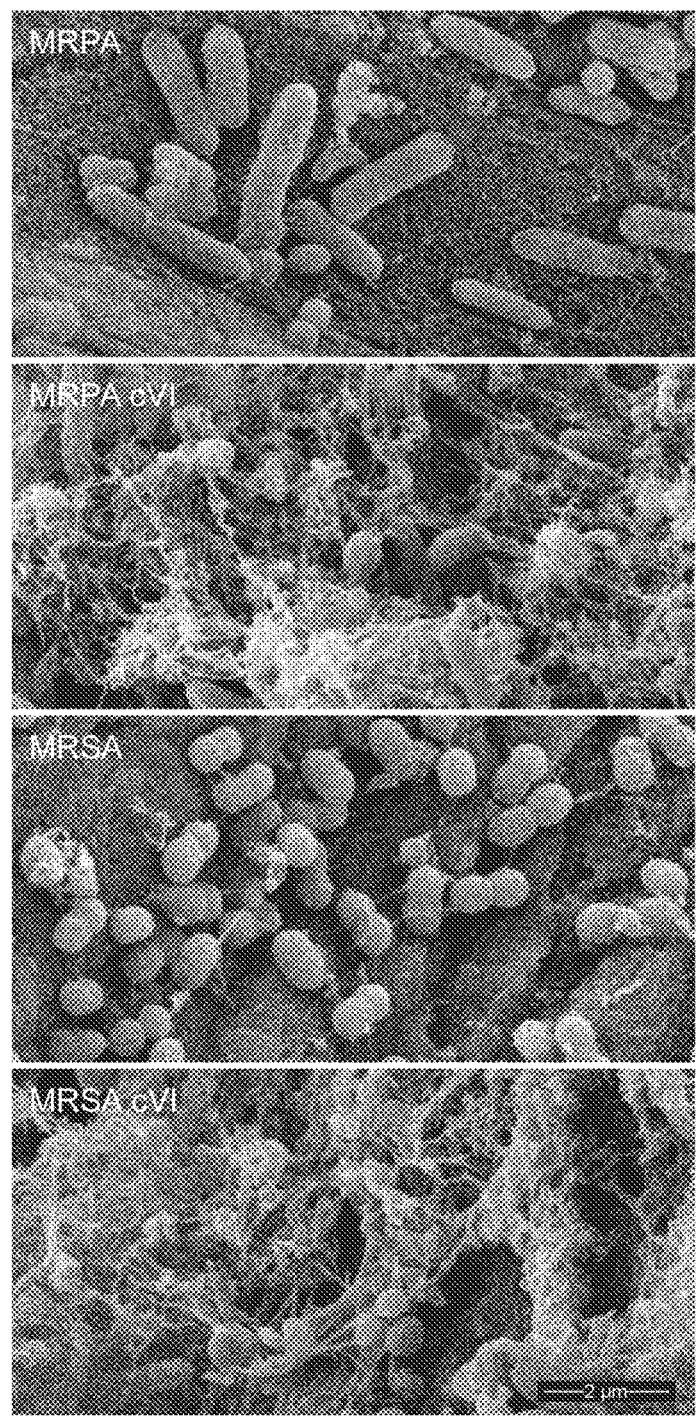

FIG. 15. Killing of multidrug-resistant Pseudomonas aeruginosa (MRPA) and multidrug-resistant Staphylococcus aureus (MRSA) by collagen type VI. Bacteria ($2\times10^6$ cfu/ml) were incubated with 1 μM collagen VI in salt buffer (10 mM Tris-HCl, 150 mM NaCl and 5 mM glucose; pH 7.4) for 2 h at 37° C. with 5% $CO_2$. Bacteria treated with collagen VI (MRPA cVI, MRSA cVI) show extensive membrane rupture and exudation of cytoplasmic content as visualized by scanning electron microscopy. Similarly, extensive membrane permeabilization were observed in the presence of collagen VI-derived peptides (not shown). In contrast, untreated bacteria (MRPA, MRSA) display an undistorted architecture. The scale bar represents 2 μm.

Figure 16:
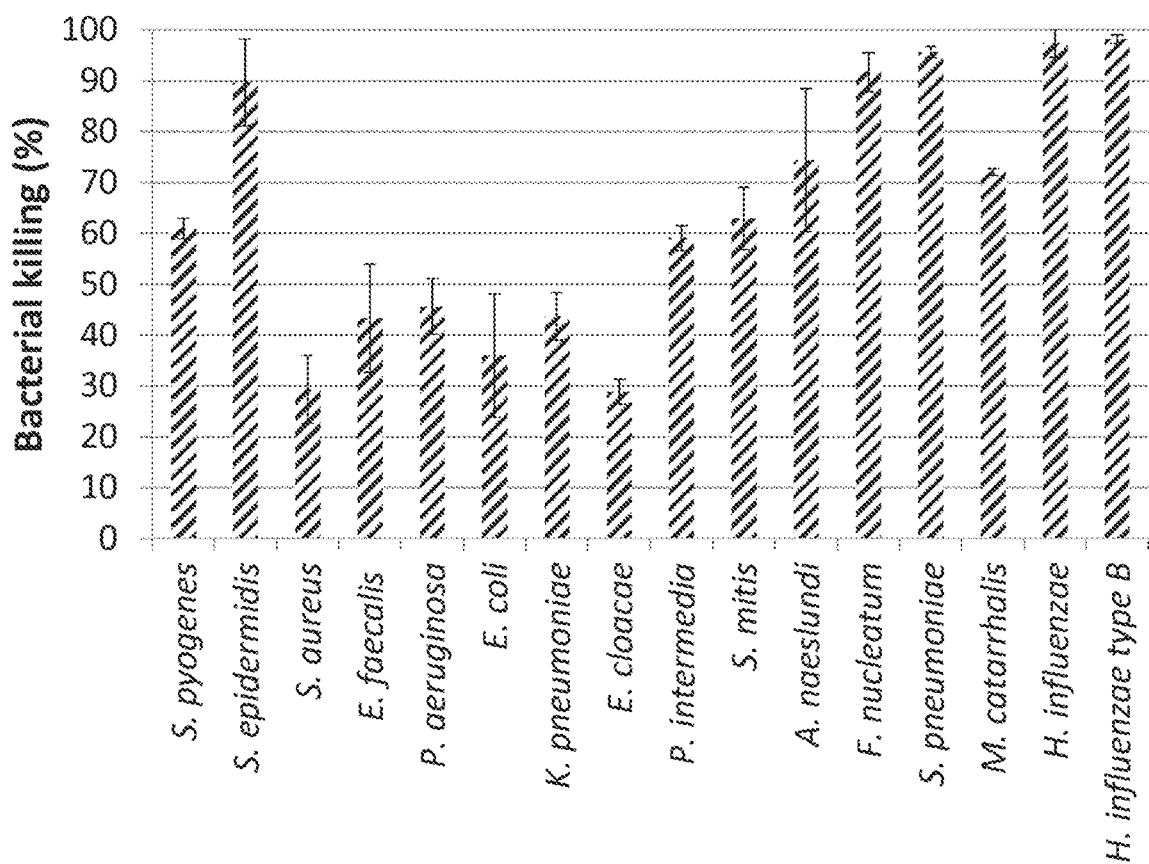

FIG. 16. Broad-spectrum antibacterial activities of collagen type VI against various Gram-negative and Gram-positive microorganisms. In viable count assays, $2\times10^7$ cfu/ml bacteria were incubated with collagen type VI (1 μM) in the presence of salt buffer (10 mM Tris-HCl, 150 mM NaCl and 5 mM glucose; pH 7.4). The data shown are representative of at least three independent experiments and mean values are presented.

Figure 17:
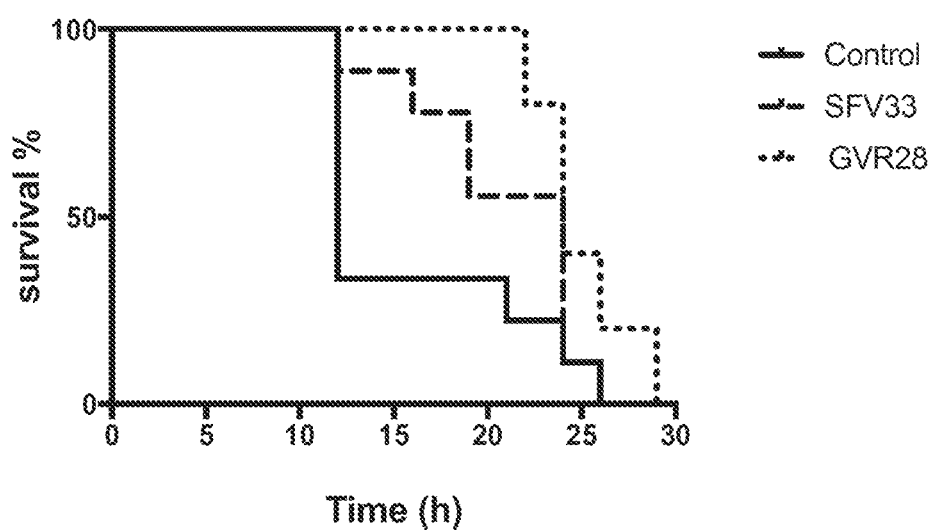

FIG. 17. Collagen VI-derived peptides improve survival in an invasive P. aeruginosa infection model. Mice were injected intraperitoneally with $2\times10^8$ cfu/ml P. aeruginosa bacteria and treated with 100 μL SFV33, GVR28 or 100 μL PBS (n=6/group).

EXAMPLES

Example A

Introduction

The purpose of this study was to investigate if the globular domains of collagen type VI have a role in host defence during infection, and if peptides derived from these domains have similar properties.

Materials and Methods

Bacterial Strains and Culture Conditions

Streptococcus pyogenes strain AP1 (40/58) of serotype M1 was from the World Health Organization Collaborating Centre for Reference and Research on Streptococci, Prague, Czech Republic. Staphylococcus aureus strain 111 and Escherichia coli strain 1351 were collected at the Department of Clinical Microbiology, Lund University Hospital, Sweden. The Pseudomonas aeruginosa strain used in this study was PAO1 (ATCC, Teddington Oly, UK), originally isolated from a wound. All bacteria were routinely grown in Todd-Hewitt broth (THB[2], Difco, Detroit, DI, USA) and incubated at 37° C. in a humid atmosphere with 5% $CO_2$.

Recombinant Expression and Purification of N- and C-Terminal VWA Domains of Collagen Type VI α-Chains Collagen type VI microfibrils were extracted from bovine cornea by collagenase digestion as described by Abdillahi et al. (36). The cDNA constructs coding for the non-collagenous domains of collagen type VI were generated by RT-PCR on total RNA from mouse brain and cloned with 5'-terminal NheI or XhoI and 3'-terminal BamHI or XhoI restriction sites using the following primers, see Table 2 (38).

TABLE 2

Primers and restriction enzymes used for RT-PCR analysis of globular regions of collagen type VI.

| Primer | Sequence | Restriction Enzyme | SEQ ID NO: |
|---|---|---|---|
| α1N(fw) | 5'-AGAGCTAGCATGCCCTGTGGATCTATTC-3' | NheI | 24 |
| α1N(rev) | 5'-GCACTCGAGAATCATGTCCACAATGGTGT-3' | XhoI | 25 |
| α1C(fw) | 5'-GCAGCTAGCTGCACATGTGGACCCATTGA-3' | NheI | 26 |
| α1C(rev) | 5'-AACCTCGAGGCCCAGTGCCACCTTCCT-3' | XhoI | 27 |
| α2N(fw) | 5'-AGAGCTAGCAAGGCCGACTGCCCAGTC-3' | NheI | 28 |
| α2N(rev) | 5'-GCACTCGAGGACCTTGATGATGCGGTT-3' | XhoI | 29 |
| α2C(fw) | 5'-GAAGCTAGCTGTGAGAAGCGCTGTGGT-3' | NheI | 30 |
| α2C(rev) | 5'-GCAGGATCCACAGATCCAGCGGATG-3' | BamHI | 31 |
| α3N(fw) | 5'-TATCTCGAGCTGATGGATCTGCTGTGAGGTTA-3' | XhoI | 32 |
| α3N(rev) | 5'-AGGAACCAGGGATCCCAGGGGCCTGTCATACATGAAGCC-3' | BamHI | 33 |
| α3C(fw) | 5'-AAAGCTAGCCTGGAGTGCCCTGTATTCCCAAC-3' | NheI | 34 |
| α3C(rev) | 5'-TTTGGATCCTCAAACTGTTAACTCAGGACTAC-3' | BamHI | 35 |

Each of the amplified PCR products were inserted into a modified pCEP-Pu vector containing an N-terminal BM-40 signal peptide and a C-terminal tandem strepII-tag downstream of the restriction sites (39). HEK293-EBNA cells (Invitrogen, Carlsbad, CA) were transfected with the recombinant plasmids using FuGENE 6 reagent (Roche, Mannheim, Germany) according to the manufacturer's protocol. The cells were selected with puromycin (1 µg/ml) (Sigma-Aldrich, St. Louis, MO) and the recombinant proteins were purified directly from Dulbecco's modified eagle's medium (Invitrogen) supplemented with fetal calf serum (Biochrom GmbH, Berlin, Germany). After filtration and centrifugation (1 h, 10,000×g), the cell culture supernatants were applied to a Streptactin column (1.5 ml, IBA GmbH, Göttingen, Germany) and eluted with 2.5 mM desthiobiotin (Sigma-Aldrich), 10 mM Tris-HCl, pH 8.0.

Viable count assay Bacteria were grown to mid-logarithmic phase ($OD_{620}$≈ 0.4) in THB-medium at 37° C. with 5% $CO_2$. The bacterial solution was subsequently washed and adjusted to 2×10$^9$ cfu/ml in 10 mM Tris, pH 7.4, containing 5 mM glucose. S. pyogenes, S. aureus, E. coli or P. aeruginosa were then incubated with 2 µM of purified collagen type VI at 37° C. for 2 h. In some experiments S. pyogenes was incubated with recombinant collagen type VI fragments at various concentrations (0.125, 0.25, 0.5, 1.0 and 2.0 µM) for 2 h at 37° C. Bacteria incubated with Tris-HCl pH 7.4 buffer or 3 µM LL-37 (Innovagen, Lund, Sweden) were used as negative and positive controls respectively. To quantify the bactericidal activity, serial dilutions of the incubation mixtures were plated on blood agar plates, followed by incubation at 37° C. overnight, and the number of colony forming units (cfu) were determined. Hundred percent survival was defined as total survival of bacteria in the same buffer and under the same condition in the absence of collagen type VI or recombinant proteins.

Scanning Electron Microscopy

S. pyogenes, S. aureus, E. coli or P. aeruginosa (2×10$^9$ cfu/ml) were incubated with purified collagen type VI at a concentration of 2 µM for 0, 30, 60 and 120 min at 37° C. with 5% $CO_2$. In some experiments S. pyogenes was incubated with 2 µM of recombinant collagen type VI fragments for 2 h at 37° C. 3 µM of LL-37 was used as a positive control and bacteria in Tris-HCl, pH 7.4 was used as negative control. Samples were fixed with 2.5% glutaraldehyde in 0.1 M sodium cacodylate, pH 7.4 (cacodylate buffer), washed with cacodylate buffer and dehydrated with an ascending ethanol series as previously described (40). The specimens were then subjected to critical-point drying with carbon dioxide and absolute ethanol was used as an intermediate solvent. The tissue samples were mounted on aluminium holders, sputtered with 20 nm palladium/gold, and examined in a Philips/FEI XL 30 FEG scanning electron microscope operated at 5 kV accelerating voltage.

Fluorescence Microscopy

Bacteria were grown to mid-logarithmic phase in THB-medium, washed and resuspended in 10 mM Tris-HCl containing 5 mM glucose to obtain a suspension of 2×10$^7$ cfu/ml. 100 pl of the bacterial suspension was incubated with 2 µM of purified collagen type VI or 3 µM LL-37 at 37° C. for 30 min, followed by addition of 200 pl of FITC (6 µg/ml, Sigma-Aldrich) and incubated for 30 min at 37° C. Bacteria were washed and immobilized onto poly-L-lysine (Sigma-Aldrich) coated glass slides by incubating for 45 min at 37° C. The slides were washed with Tris-HCl/glucose and were fixes with 4% paraformaldehyde (PFA) by incubating at 4° C. for 15 min followed by 45 min incubation at RT. The glass slides were subsequently mounted on coverslips using Prolong Gold antifade reagent mounting medium (Invitrogen). The bacteria were visualized in a Nikon Eclipse E80i fluorescence microscope equipped with a Nikon DS-Fi 1 camera, a Plan Apochromat (100× objective) and a high numerical aperture oil condenser.

Heparin-Binding Assay

LL-37 (5 µg) or recombinant fragments from collagen type VI (10 µg) were applied to nitrocellulose membranes (Hybond-C; GE Healthcare, Uppsala, Sweden). Membranes were blocked with 2% BSA in PBS (w/v) for 2 h at RT, followed by washing steps with PBST (PBS with Tween-20) and incubated with 60 µg of heparin-biotin (Sigma-Aldrich) overnight at 4° C. In some experiments, unlabeled heparin (6 mg/ml) was added for competition of binding. After washing, the membranes were incubated with HRP streptavidin (Sigma-Aldrich) for 30 min at RT, washed and the bands were visualized by the Supersignal West Pico Chemi-luminescent substrate developing system (Thermo Fischer Scientific, Roskilde, Denmark).

Transmission Electron Microscopy

The binding of recombinant collagen type VI fragments to the bacterial surface was visualized by negative staining and transmission electron microscopy as described previously (35). Briefly, bacteria were incubated with recombinant collagen type VI fragments in presence or absence of heparin (10 µg/ml) for 1 h at 37° C. For visualization in the electron microscope the different recombinant fragments were conjugated with 5 nm colloidal gold (41). Specimens were examined in an Philips/FEICM 100 TWIN transmission electron microscope operated at 60 kV accelerating voltage. Images were recorded with a side-mounted Olympus Veleta camera and the ITEM acquisitions software.

Sequence and Structural Analysis

The amino acid sequence of human collagen type VI α-chains can be accessed through UniProtKB database; α1(VI) (UniProt #P12109), α2(VI) (UniProt #P12110) and α3(VI) (UniProt #P12111). Swiss PDB viewer DeepView version 4.1 was used for sequence alignment and to analyze three-dimensional structures. Only a crystal structure of mouse α3N5 was available with PDB code 4IGI (42). No crystal structures were available for human VWA domains of collagen type VI and predicted models from ModBase (modbase.compbio.ucsf.edu) were therefore used to generate the figures. There were no predicted models for N1 and C2 domains of α3(VI).

Peptide Synthesis

```
GVR28
                                       [SEQ ID NO: 1]
(GVRPDGFAHIRDFVSRIVRRLNIGPSKV),

FYL25
                                       [SEQ ID NO: 2]
(FYLKTYRSQAPVLDAIRRLRLRGGS),

FFL25
                                       [SEQ ID NO: 3]
(FFLKDFSTKRQIIDAINKVVYKGGR),

VTT30
                                       [SEQ ID NO: 4]
(VTTEIRFADSKRKSVLLDKIKNLQVALTSK),

SFV33
                                       [SEQ ID NO: 5]
(SFVARNTFKRVRNGFLMRKVAVFFSNTPTRASP),
and DVN32
                                       [SEQ ID NO: 6]
(DVNVFAIGVEDADEGALKEIASEPLNMHMFNL)
``` were synthesized by Biopeptides (San Diego, CA). The purity (>95%) and molecular mass of these peptides was confirmed by MALDI-TOF MS analysis. All peptides used were water-soluble except DVN32, which was dissolved in <0.01% DMSO.

Radial Diffusion Assay

Radial diffusion assay (RDA)[2] was performed essentially as described earlier (43, which is incorporated herein by reference) with some minor modifications. Bacteria were grown to mid-logarithmic phase ($OD_{620} \approx 0.4$) in 10 ml of full-strength (3% w/v) trypticase soy broth (TSB)[2] (Becton Dickinson, Franklin Lakes, NJ). Bacteria were then washed once with 10 mM Tris-HCl (containing 5 mM glucose; pH 7.4). Subsequently, $4 \times 10^6$ cfu/ml of bacteria were added to 5 ml of the underlay agarose gel, consisting of 0.03% (w/v) TSB, 1% (w/v) low electro endosmosis-type agarose and 0.02% (v/v) Tween 20 (both from Sigma-Aldrich). The underlay was poured into a φ90 mm Petri dish. After agarose solidification, φ4 mm wells were punched out, and 6 pl of 10 mM Tris-HCl buffer alone or containing peptide (100 µM) were added to each well. Plates were incubated at 37° C. for 3 h to allow diffusion of the peptides. The underlay gel was then covered with 5 ml of the overlay (6% TSB and 1% low electro endosmosis-type agarose in distilled $H_2O$). Antimicrobial activity was seen as a clearing zone around each well after incubating 18-24 h at 37° C.

Statistical Analysis

Student's t test was performed to determine statistical significance. Values were expressed as means±standard errors and significance was determined as a P value of <0.05.

Results and Conclusions

Figure 1B:
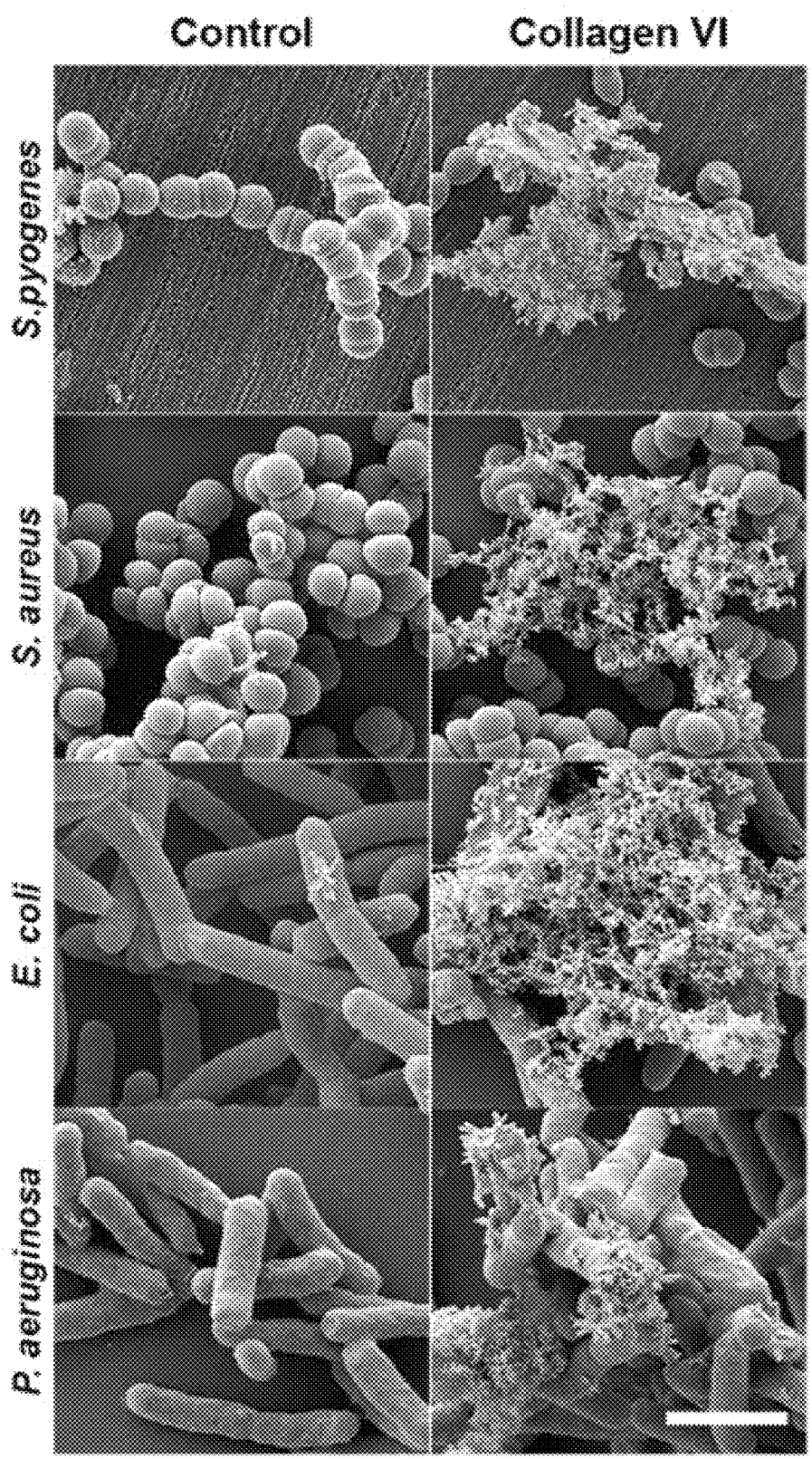
Figure 1C:
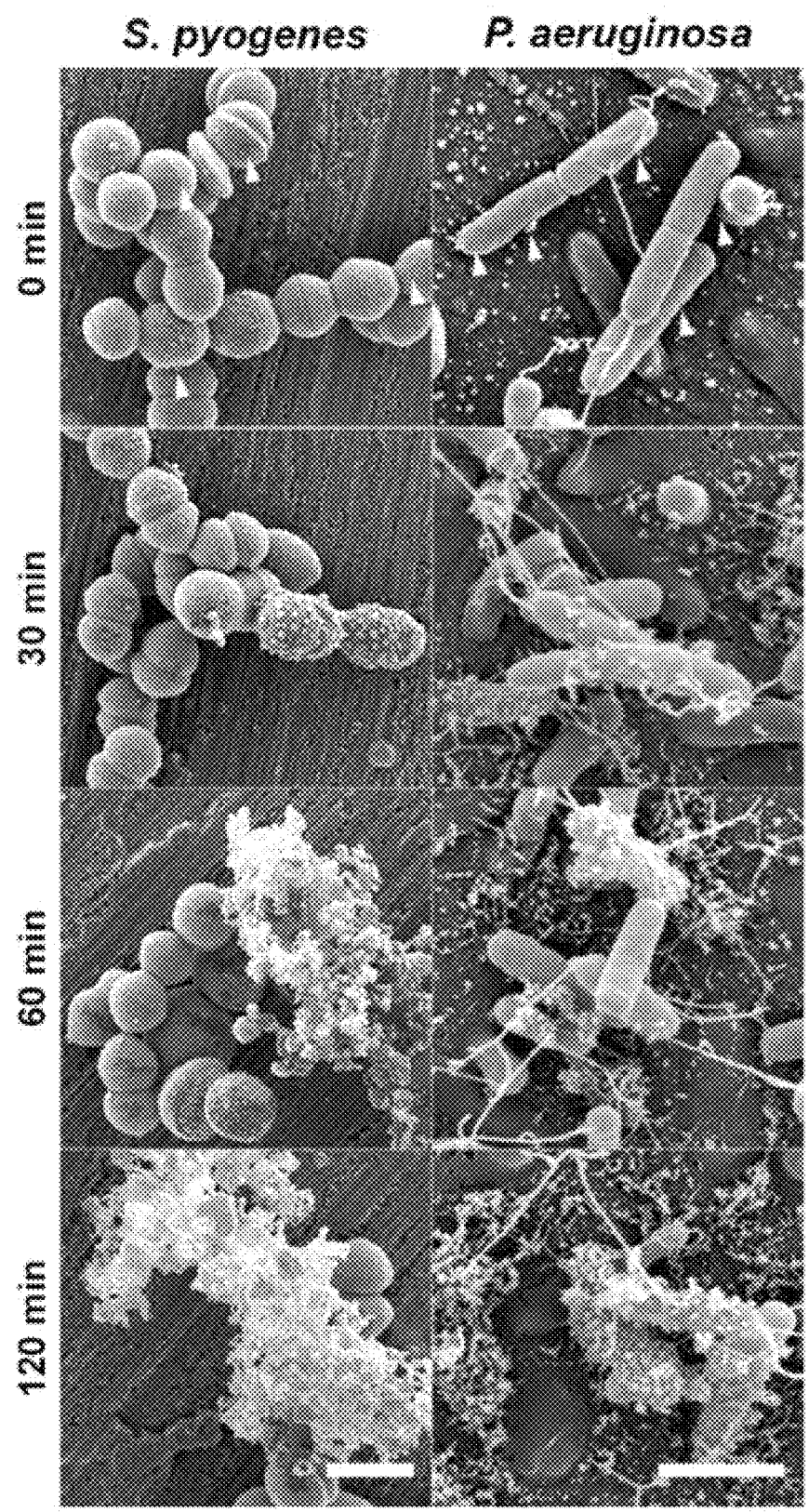
Figure 1D:
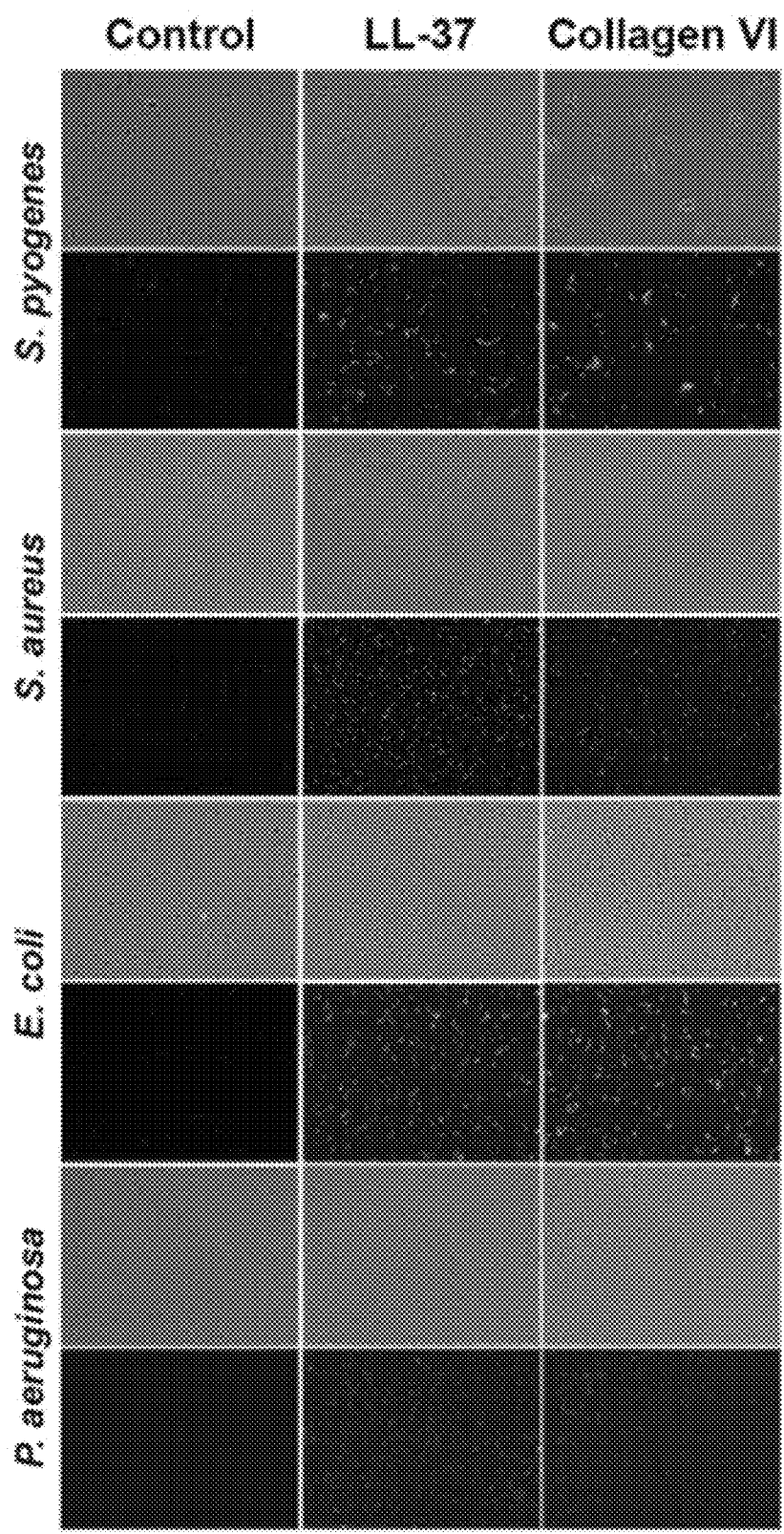

Collagen Type VI Kills Gram-Positive and Gram-Negative Human Pathogens by Membrane Permeabilization An integrated approach was established to combine microbiological and biochemical assays with high resolution scanning electron microscopy in order to investigate the antimicrobial properties of collagen type VI. Viable count assays were performed by incubating the Gram-positive bacteria S. pyogenes and S. aureus as well as the Gram-negative bacteria E. coli and P. aeruginosa with purified collagen type VI for 2 h at 37° C. The results showed that collagen type VI indeed displayed antibacterial activity against S. aureus, E. coli and P. aeruginosa in a similar way as observed for S. pyogenes, the chosen model organism (FIG. 1A). The human benchmark antimicrobial peptide LL-37 was used as a positive control and showed almost 100% killing of all the bacteria strains. To examine whether collagen type VI disrupts the bacterial membrane, high resolution scanning electron microscopy was used to visualize bacterial architecture during killing in a more three-dimensional way. Bacteria were either incubated with buffer alone or with collagen type VI (FIG. 1B). The results showed extensive disruption of the bacterial membrane structure and extravasations of cytoplasmic components in the presence of collagen type VI indicating damage to the bacterial membranes (FIG. 1B, right panel, FIG. 1C). These findings were similar to those seen after treatment with LL-37 (data not shown). In contrast, in the control samples, bacterial cell wall architecture remained unaffected (FIG. 1B, left panel). These observations were further substantiated by the use of the impermeant dye FITC. Fluorescence microscopy analysis showed that the uptake of FITC was only visible in samples treated with collagen type VI or LL-37 (FIG. 1D), thus demonstrating permeabilization of the bacterial membrane. Similar observations were made for a variety of other Gram-positive and Gram-negative human pathogens (FIG. 16). Taken together, these data demonstrate that collagen type VI exhibits a broad-spectrum antimicrobial activity against Gram-positive and Gram-negative bacteria.

Figure 2A:
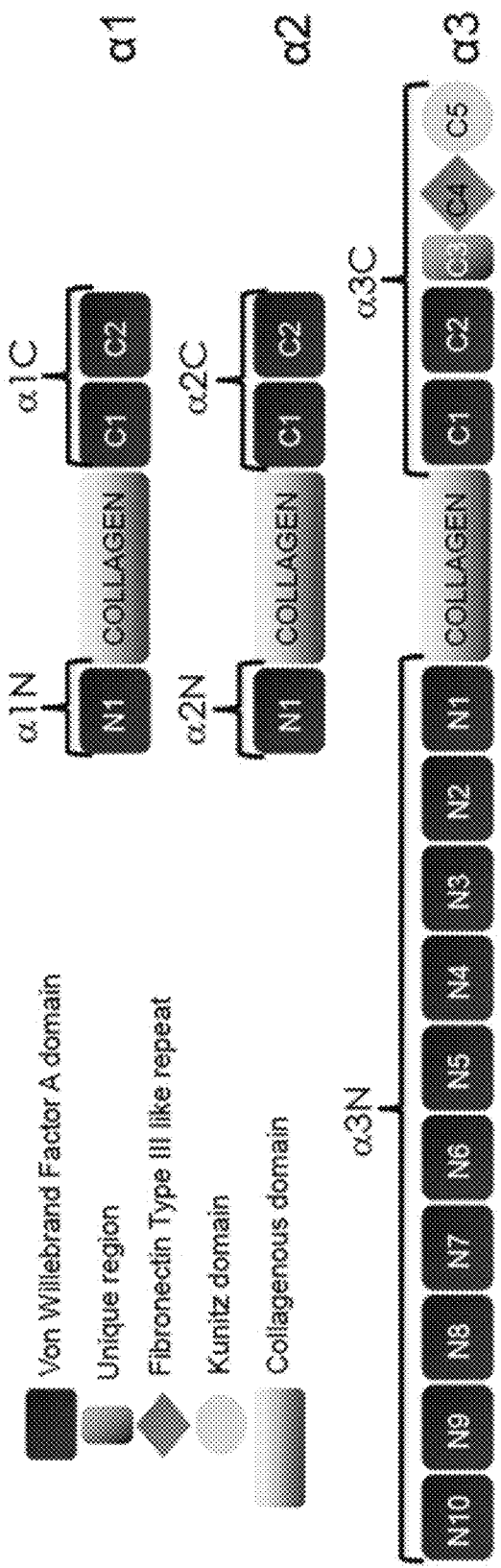
Figure 2B:
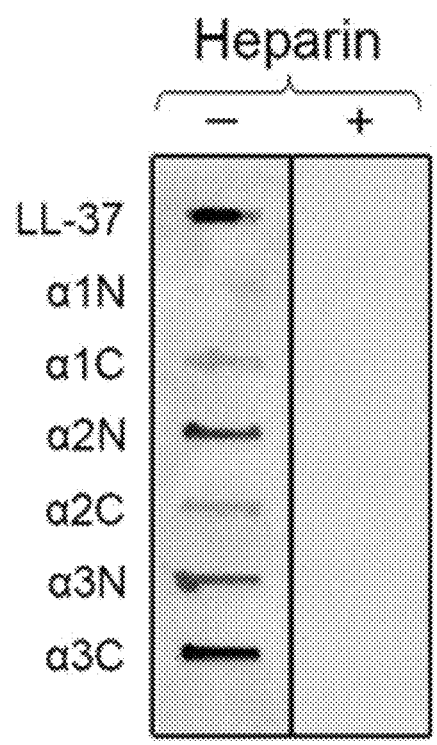
Figure 2C:
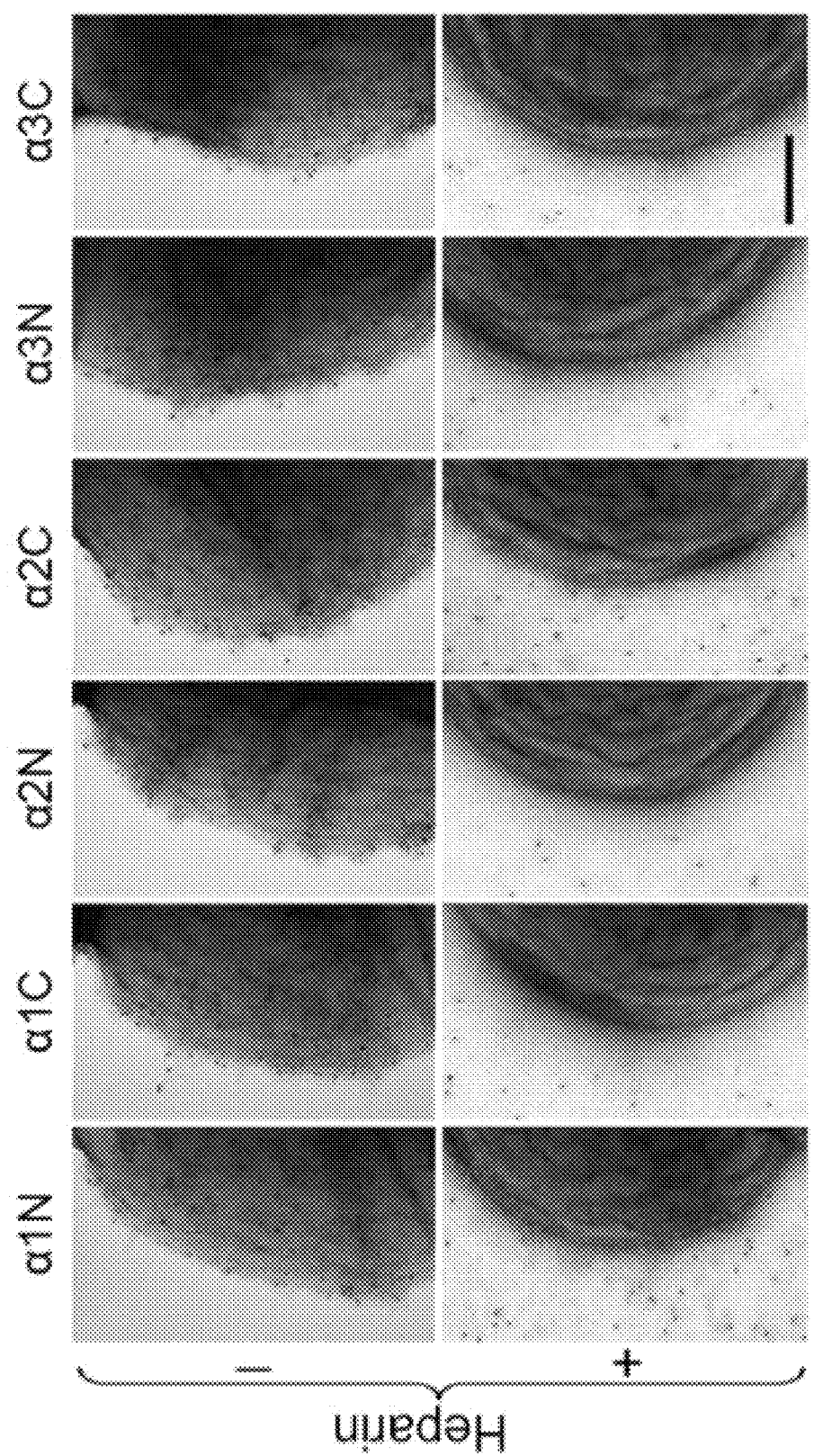
Figure 2D:
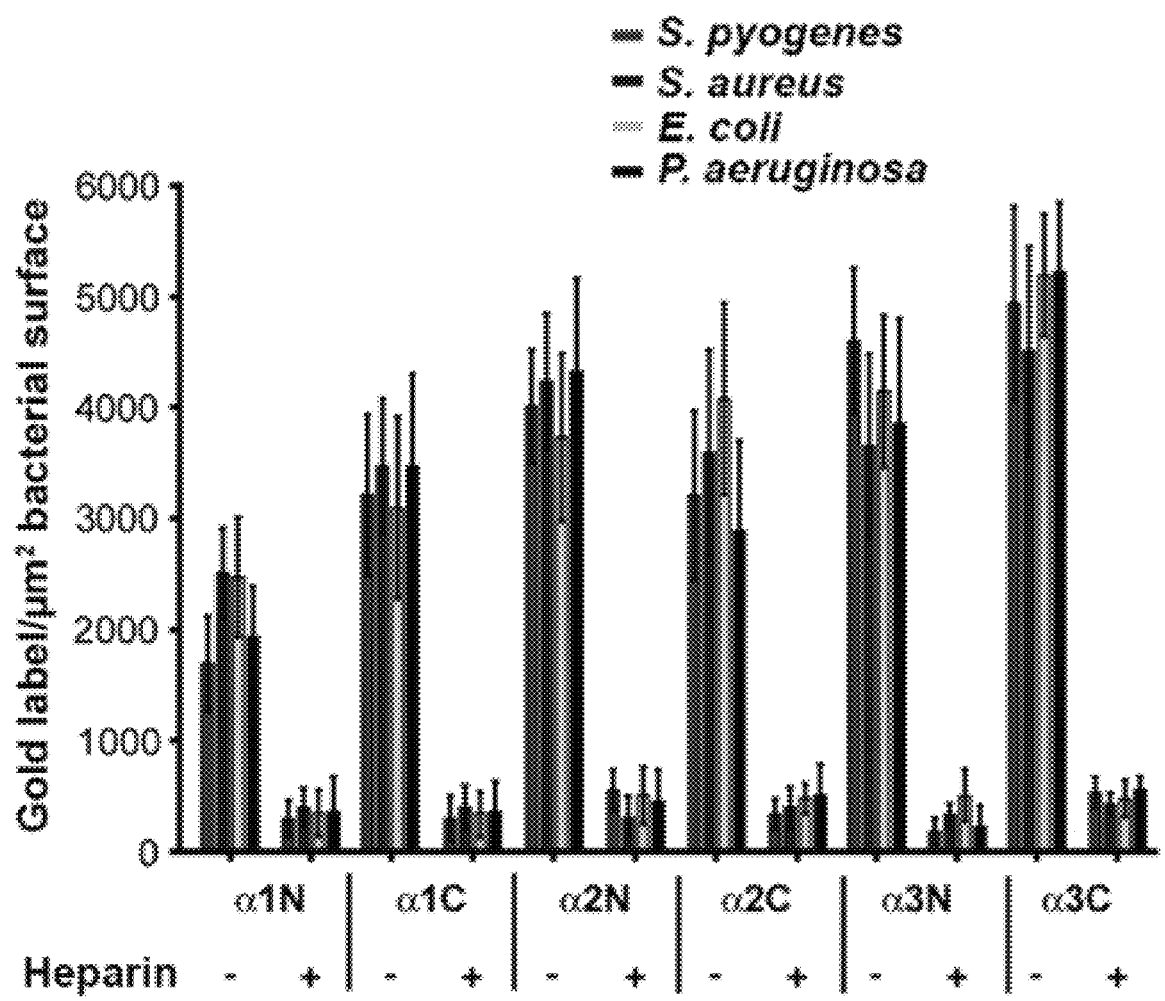

The Recombinant VWA Domain-Containing Globular Regions of Collagen Type VI Bind to the Bacterial Surface in a Heparin-Dependent Manner The affinity for negatively charged surfaces on bacterial membranes is a prerequisite for any given antimicrobial molecule for induction of bacterial killing, regardless of their mode of action. Thus, most antibacterial peptides and proteins are characterized by their affinity for heparin (32, 44). To determine whether collagen type VI exhibited similar properties biotin-labeled heparin was tested in a slot blot assay for binding to immobilized recombinant fragments of collagen type VI (as denoted in FIG. 2A). Heparin bound to the different N- and C-terminal regions with varying intensity (FIG. 2B, left panel). Interestingly, the affinity of heparin to α3C was comparable to LL-37, the positive control. The binding to all fragments was blocked by non-labeled heparin (FIG. 2B, right panel). For visualization of these interactions, collagen type VI fragments were directly conjugated to colloidal gold and incubated with S. pyogenes bacteria. Negative staining and transmission electron microscopy revealed that all fragments bound to the bacterial surfaces in the absence of heparin (FIG. 2C, upper panel). No binding was observed in the presence of heparin, and instead gold conjugates were distributed randomly in the background (FIG. 2C, lowerpanel). Similar results were obtained for S. aureus, E. coli and P. aeruginosa in the absence or presence of heparin (FIG. 2D). This was also the case for the full-length protein (data not shown).

The Recombinant VWA Domain-Containing Globular Regions of the Three Collagen Type VI α-Chains Induce Bacterial Killing by Membrane Disruption In order to correlate the antibacterial activity of collagen type VI to individual N- and C-terminal globular regions, the bactericidal effect of the recombinant proteins on streptococci was investigated. Bacteria from the S. pyogenes strain AP1 were incubated with increasing concentrations of protein and analysed by viable count assays. The bacteria showed dose-dependent killing in the presence of the different fragments (FIG. 3A). Interestingly, N- and C-terminal regions from the α3(VI) were more potent than the respective domains from the α1(VI) and α2(VI). To analyse these findings at the ultrastructural level, specimens of bacteria incubated with VWA domains were examined by high resolution scanning electron microscopy. As depicted in FIG. 3B, bacteria indeed showed significant structural alterations such as membrane perturbations, blebbing and exudation of cytoplasmic constituents. Notably, streptococci treated with α3N and α3C displayed significantly more membrane disruption. In contrast, control bacteria treated under similar conditions with only buffer were not affected (FIG. 3B, top). These results implicate that the individual VWA domain-containing globular regions of collagen type VI exhibit a mode of bacterial killing, which is similar to the holoprotein.

The VWA Domains of the Collagen Type VI α3-Chain Contain Amphipathic Amino Acid Motifs with Putative Antibacterial Activity Cationic, hydrophobic and amphipathic properties are essential to the very core of antimicrobial peptide activity as the combination of these properties govern the extent to which bacterial killing is induced (9, 45). Therefore, in silico sequence analysis of the VWA domains of the α3(VI) chain was performed to identify such amino acid motifs with putative antimicrobial activity. The α3(VI) was chosen because it turned out to be most efficient in bacterial killing as described above. First, we defined the possible secondary structure by aligning the sequences of the N- and C-terminal VWA domains (N10-N2 and C1, see FIG. 2A) using Swiss-Pdb Viewer program. This analysis revealed that these domains are predicated to assume α-helices (FIG. 4, rectangular boxes) as well as β-strands (FIG. 4, black arrows). Furthermore, 3D-models generated with ModBase proposed that these domains consist of a central six-stranded hydrophobic β sheet flanked on either side by three amphipathic α helices (data not shown). These findings are in general accordance with structural data obtained by x-ray crystallography of the mouse α3N5 domain (42). The VWA domains N1 and C2 (see FIG. 2A) were not included in this study since there were no molecular models available in any database. Next, amino acids that were likely to be exposed on the surface were determined (FIG. 4, bold letters) in order to predict possible interaction site(s) between these domains and the bacterial membrane. By combining these results together with positively charged areas (FIG. 4, highlighted in grey) in the sequence, it was possible to predict putative antimicrobial regions as indicated in blue boxes.

Peptides Derived from the VWA Domains of the Collagen Type VI α3-Chain Exert Bactericidal Activity Peptide sequences from putative antimicrobial regions with a high total net charge and hydrophobicity were identified, as these properties are important prerequisites for AMPs (46, 47). In total, five peptides were chosen from the N3, N2 and C1 domains (FIGS. 5, B and C). Surface representation models were also generated in order to get an overview of the net charge of these domains and indeed, the C1 and N3 domains displayed a large number of cationic regions on their surface (FIG. 5A). Similar patterns, although to a somewhat lesser extent, were found for N2. The N10 domain showed more anionic residues on its surface (FIG. 5A) and a peptide synthesized from that domain was used as a negative control (DVN32). In order to verify the antibacterial activity of the selected VWA-derived peptides, all peptides were screened in radial diffusion assays (RDA) for bactericidal activity against E. coli, S. aureus and P. aeruginosa. All the peptides exhibited significant bactericidal activity against all tested strains to varying extent (FIG. 6, A-C). Interestingly, in most cases, the observed bacterial killing potential was considerably higher than our positive control, the "classical" host defence peptide LL-37. These findings show that VWA domains of the α3(VI) chain contain several antimicrobial motifs.

Example B

Introduction

The purpose of this example was to further investigate the mode of action and immunomodulatory effects of host defence peptides derived from collagen type VI.

Materials and Methods

Bacterial Strains

Streptococcus pyogenes strain AP1 (40/58) of serotype M1 was from the World Health Organization Collaborating Centre for Reference and Research on Streptococci, Prague, Czech Republic. Staphylococcus aureus strain 111 and Escherichia coli strain 1351 were collected at the Department of Clinical Microbiology, Lund University Hospital, Sweden. The Pseudomonas aeruginosa strain used in this study was PAO1 (ATCC, Teddington Oly, UK), originally isolated from a wound.

Growth Media

All bacteria were routinely grown in Todd-Hewitt broth (THB, Difco, Detroit, DI, USA) by incubating at 37° C. in a humid atmosphere with 5% $CO_2$.

Collagen Type VI Extraction and Peptide Synthesis

Collagen type VI microfibrils were extracted from bovine cornea by collagenase digestion as described by Spissinger et al (34), with modifications from Bober et al. (35). In short, bovine corneas were cut into pieces and homogenized in Tris/saline buffer containing 5 mM calcium chloride and protease inhibitors. The homogenate was digested with collagenase type 1 (Worthington biochemical corporation, Lakewood, NJ). Non-dissolved material was pelleted by centrifugation at 48,000×g for 20 min. The supernatant was applied in 500-μl aliquots onto a Superose 6 column of 25 ml (Amersham Biosciences, Uppsala, Sweden) equilibrated and eluted with homogenization buffer at 0.2 ml/minute. Fractions of 0.5 ml were collected, and those containing collagen VI were pooled and stored at 4° C. Collagen type VI-derived peptides (see Table 3) were synthesized by Biopeptides (San Diego, USA). LL-37 (LLGDFFRK-SKEKIGKEFKRIVQRIKDFLRNLVPRTES) (SEQ ID NO: 36) was purchased (Innovagen AB, Lund, Sweden). The purity (>95%) and molecular mass of these peptides was confirmed by MALDI-TOF MS analysis. All peptides used were water-soluble except DVN32, which was dissolved in <0.01% DMSO (Sigma-Aldrich, St Louis).

Transmission Electron Microscopy

The binding of peptides to the surface of the bacteria and LPS was visualized by negative staining and transmission electron microscopy as described previously (35). Briefly, bacteria (2×10$^9$ cfu/ml) were incubated with 2 μM peptide conjugated with 10 nm colloidal gold for 2 h at 37° C. with 5% $CO_2$. For LPS (from *Escherichia coli* 0111:1B4, Sigma-Aldrich) binding, 2 μM peptide conjugated with 10 nm colloidal gold was incubated with LPS (10 μg/ml) for 1 h at RT. Specimens were examined in an Philips/FEICM 100 TWIN transmission electron microscope operated at 60 kV accelerating voltage. Images were recorded with a side-mounted Olympus Veleta camera and the ITEM acquisitions software.

the range of 200-260 nm (scan speed was 20 nm/min). Averages of five scans were baseline-subtracted.

Bactericidal Assay

Bacteria were grown to mid-logarithmic phase ($OD_{620}$≈0.4) in THB medium at 37° C., with 5% $CO_2$. The bacterial solution was subsequently washed and adjusted to 2×10$^7$ cfu/ml in salt buffer (10 mM Tris-HCl, 150 mM NaCl supplemented with 5 mM glucose; pH 7.4) (both from Sigma-Aldrich). Various concentrations of peptides (0.3, 0.6, 3, 6, 30 and 60 μM) were incubated with bacteria in salt buffer with or without 20% human plasma. Bacteria incubated in only salt buffer with or without plasma were used as negative controls. Samples with LL-37 served as positive controls. The samples were incubated for 2 h at 37° C. with 5% $CO_2$. To quantify the bactericidal activity, serial dilutions of the incubation mixtures were plated on THB agar plates, followed by incubation at 37° C. with 5% $CO_2$ overnight, and the number of cfu were determined. Experiments were performed in triplicate. Hundred percent survival was defined as total survival of bacteria in the same buffer and under the same condition in the absence of peptides.

Propidium Iodide Uptake Assay

Bacterial membrane permeabilization was assessed by using propidium iodide (PI) (Sigma-Aldrich) dye as described previously (39). Briefly, bacteria were grown to mid-logarithmic phase ($OD_{620}$≈0.4), washed and adjusted to 2×10$^9$ cfu/ml. Bacteria (diluted 1:100) were mixed with peptides (30 μM final concentration) in the presence of salt buffer with or with plasma and incubated for 2 h at 37° C., with 5% $CO_2$. PI (0.5 mg/ml) was added to each sample and incubated for 30 min on ice in darkness. Samples were analyzed on a Flow cytometer (BD Accuri flow cytometer,

TABLE 3

Amino acid sequence and physiochemical properties of peptides used in this study.

| Peptide[a] | Amino acid sequence[b] | MW (Da) | Charge | Hydrophobicity | SEQ ID NO: |
|---|---|---|---|---|---|
| GVR28 | GVRPDGFAHIRDFVSRIV RRLNIGPSKV | 3163 | +4 | 46% | 1 |
| FYL25 | FYLKTYRSQAPVLDAIRR LRLRGGS | 2937 | +5 | 40% | 2 |
| FFL25 | FFLKDFSTKRQIIDAINKV VYKGGR | 2944 | +4 | 40% | 3 |
| VTT30 | VTTEIRFADSKRKSVLLD KIKNLQVALTSK | 3403 | +4 | 40% | 4 |
| SFV33 | SFVARNTFKRVRNGFLM RKVAVFFSNTPTRASP | 3803 | +7 | 48% | 5 |
| DVN32 | DVNVFAIGVEDADEGALK EIASEPLNMHMFNL | 3490 | −6 | 53% | 6 |

[a] Peptides are identified by their first three $NH_2$-terminal residues using the single letter code, followed by the total number of residues constituting the peptide.
[b] Sequences of peptides are given in single letter code.

Circular Dichroism

Circular dichroism (CD) measurements were performed on a Jasco J-810 spectropolarimeter equipped with a Jasco CDF-426S Peltier set to 25° C. Measurements were performed in at least duplicate in a 10-mm quartz cuvette under stirring with a peptide concentration of 30 mM. LPS (0.2 mg/ml) was added in some samples to study the effect on secondary structure of the peptides. This was monitored in Becton Dickinson, Franklin Lakes). Bacteria incubated in only salt buffer with or without human plasma were used as negative controls. As a positive control, bacteria were treated with 70% ethanol for 20 min at room temperature. The percentage of membrane permeabilization was calculated as the percent of fluorescent intensity of peptide-treated samples with respect to fluorescence intensity of untreated samples.

Scanning Electron Microscopy

Bacteria (2×10$^9$ cfu/ml) were incubated with 30 μM peptide for 2 h at 37° C. under physiological conditions such as salt buffer with or without plasma. Samples were fixed with cacodylate buffer (2.5% glutaraldehyde (Merck, Germany) in 0.1 M sodium cacodylate (Sigma-Aldrich), pH 7.4, washed with cacodylate buffer and dehydrated with an ascending ethanol series as previously described (40). The tissue samples were mounted on aluminium holders, sputtered with 20 nm palladium/gold, and examined in a Philips/FEI XL 30 FEG scanning electron microscope operated at 5 kV accelerating voltage.

Membrane Permeabilization Assay

Dry lipid films of *E. coli* polar lipid extract were formed in round-bottom flask walls by dissolving lipids in chloroform, followed by evaporation under $N_2$-flow and subsequently placed in vacuum overnight. Lipid films were re-suspended either by 30 min stirring (*E. coli*), at 55° C. in an aqueous solution of 100 mM 5(6)-carboxyfluorescein in 10 mM Tris (set to pH 7.4 at 37° C.). Suspensions were then vortexed followed by repeated extrusion through a 100 nm polycarbonate membrane mounted in a LipoFast mini-extruder (Avanti Polar Lipids) in order to reduce multilamellar structures and polydispersity. Un-trapped carboxyfluorescein was removed by gel filtration on Sephadex PD-10 columns (GE Healthcare, Little Chalfont, UK). Membrane permeability was measured by monitoring carboxyfluorescein efflux from the liposomes to the external low concentration environment, resulting in loss of self-quenching and an increased fluorescence signal with excitation and emission wavelengths of 492 and 517 nm, respectively. Fluorescence was measured with a Varioskan Flash Multimode Reader (Thermo Fisher Scientific, Waltham, MA) in black Nunc Delta Surface 96-well plate (Thermo Fisher Scientific, Roskilde, DK). The wells were prepared with a 2-fold serial dilution of the peptides in tris buffer, as well as controls without peptides (background) and 0.16% Triton X-100 (maximum leakage). The plates were pre-heated to incubation temperature (37° C.) and administered liposome solution, to a final lipid concentration of 10 μM in 200 pl, with the Varioskan integrated dispenser. The effects of each peptide concentration on the liposome systems were monitored for 45 min, at which point the initial leakage had largely subsided. Results shown represent the average from triplicate experiments with standard deviations and are expressed as percent of total leakage generated with Triton X-100 and subtraction of the baseline value. The $EC_{50}$-values are calculated from a sigmoidal dose-response curve fitting with variable slope to the leakage percentage as a function of the peptide concentration (log 10), using Graphpad Prism.

Hemolysis Assay

Blood from healthy individuals was drawn into Vacutainer tubes (Becton Dickinson) containing EDTA and centrifuged at 800×g for 10 min. The plasma and buffy coat were removed. Erythrocytes were washed three times and resuspended in phosphate buffered saline (PBS, Medicago, USA). The cells were incubated with peptides (final concentration of 30 and 60 μM) for 1 h at 37° C. in end-over-end rotation. Cells incubated with 2% Triton X-100 (Sigma-Aldrich) served as positive control. The samples were then centrifuged at 800×g for 10 min. The supernatant was collected and the absorbance of hemoglobin release was measured at 540 nm and is expressed as % of Triton X-100 induced hemolysis.

Lactate Dehydrogenase (LDH) Assay

The cytotoxicity experiments were performed as described previously (41). Briefly, human monocytic THP-1 cells (American Type Culture Collection (ATCC), Manassas, VA) were cultured into 96-well plates using Dulbecco's Modified Eagle's medium (DMEM) (PAA Laboratories) supplemented with 10% fetal calf serum. The medium was removed and the cells were subsequently washed with DMEM. Peptides (1, 5, 10, 20, 50 μM) diluted in DMEM were added in triplicates. The LDH based TOX-7 kit (Sigma-Aldrich) was used according to the manufacturer instructions. The amount of LDH release from dead cells was measured at 450 nm. As a positive control 2% Triton X-100 was used.

LPS Stimulation of Macrophages in Vitro

Murine macrophage-like cells (RAW 264.7; ATCC) were seeded in 96-well plates at $3.5 \times 10^5$ cells/well in DMEM (without phenol red, PAA Laboratories) supplemented with 10% fetal calf serum and antibiotic-antimycotic (Invitrogen, Carlsbad, CA). After overnight incubation at 37° C., the cells were washed once with DMEM. LPS (10 ng/ml) was pre-incubated with the peptides for 20 min at room temperature and added to the cells. The cells were subsequently incubated for 24 h at 37° C. Griess reagent (Sigma, St. Louis, MO) was added to culture supernatant in 1:1 ratio followed by 15 min incubation in dark. The absorbance was then measured at 550 nm with a spectrophotometer. The cells with and without LPS stimulation were taken as positive and negative controls for LPS-induction. For the determination of NO production with peptides and LPS treatments, the assay was done in triplicate and the average values were considered for each set. Cells were grown at 37° C. and with 5% $CO_2$ in fully humidified air.

In Vitro Wound Healing Assay

HaCaT cells (ATCC) were cultured into a 24-well plate at $3 \times 10^5$ cells/well with keratinocyte basal medium, (KBM Gold, Lonza Group AG, Switzerland) according to the manufacturer instructions, until confluence. Prior to experiment cells were cultured in serum-free medium for 24 h. The cell monolayer was subjected to a mechanical scratch wound using a sterile pipette tip. Detached cells were removed by washing twice with PBS. Collagen type VI-derived peptides (10 μg/ml), LL-37 (10 μg/ml) and collagen type VI (10 μg/ml) was added to the cells and incubated for 24 h at 37° C. Cells with and without the addition of 10% FCS in the basal medium were used as positive and negative controls, respectively. All experiments were performed in a humidified atmosphere with 5% $CO_2$ at 37° C. Images of the wounded cell monolayer were taken using a microscope (Olympus, SC30 digital camera, Tokyo, Japan) at 0 and 24 h after scratched wounding.

Statistical Analysis

The data was analysed with Graphpad Prism 6. Student's t test was performed to determine statistical significance. Values were expressed as means±standard errors and significance was determined as a p value of <0.05.

Results and Conclusions

Collagen Type VI-Derived Peptides Adherence to Bacterial Surface

To examine whether collagen type VI-derived peptides (see in Table 3) interacts with bacterial surfaces, gold labelled peptides were incubated with *P. aeruginosa* and *S. aureus* and subjected to negative staining transmission electron microscopy. The electron micrographs revealed that SFV33 and LL-37 were able to adhere to the bacterial surface of *S. aureus* and *P. aeruginosa* (FIG. 7A), which was also the case for the other peptides (data not shown). Interestingly, even control peptide DVN32, which is negatively charged, bound to the bacterial surfaces of *S. aureus* and *P. aeruginosa*.

Binding of Collagen Type VI-Derived Peptides to LPS

In the next series of experiments, to determine whether Lipopolysaccharide (LPS) of Gram-negative bacteria could serve as a potential target for collagen type VI-derived peptides, *E. coli* LPS was incubated with gold conjugated peptides for 1 h and subjected to negative staining transmission electron microscopy. Both LL-37 and SFV33 bound to LPS (FIG. 7B), whereas DVN32 bound somewhat. To investigate the interaction between LPS and these peptides their secondary structures were analysed using circular dichroism (CD) analysis. LL-37 clearly adopted a helical structure in the presence of LPS (FIG. 7C), whereas, DVN32 did not change its structure and remained linear. The CD spectra shows that SFV3 conformations change resemble a random coil structure compared to the other peptides (GVR28, FFL25, FYL25 and VTT30), which displayed a mixture of alpha helix and beta sheet (data not shown).

Collagen Type VI-Derived Peptides Show Antibacterial Activity at Physiological Conditions The antibacterial activities of many AMPs are inhibited in a physiological environment such as high salt concentration or the presence of plasma proteins (48, 49). Viable count assays were performed using collagen type VI derived peptides. For this purpose, a panel of Gram-positive bacteria *S. pyogenes* and *S. aureus* as well as the Gram-negative bacteria *E. coli* and *P. aeruginosa* were subjected to collagen type VI-derived peptides in the presence of physiological salt with or without 20% human plasma. For comparison, the classical AMP LL-37 was used at the same concentrations. FIG. 8 shows that SFV33 kills *P. aeruginosa* and *E. coli* very efficiently in plasma, while its antimicrobial activity towards *S. pyogenes* were slightly reduced. Notably, the antimicrobial effect of SFV33 was dose-dependent in both conditions. None of the peptides exerted antibacterial activity against *S. aureus* in the presence of plasma (FIG. 8). In salt conditions, SFV33 showed almost similar effects as for LL-37, whereas GVR28 showed somewhat reduced effects. In contrast, the negative control peptide (DVN32), as expected, did not exert antibacterial activity, even at higher concentrations.

Membrane-Permeabilizing Activity of Collagen Type VI-Derived Peptides

In order to investigate the effects of collagen type VI-derived peptides on bacterial membranes, propidium iodide uptake was measured. As shown in FIG. 9A, a significant degree of membrane permeabilization was induced on *P. aeruginosa* and *S. aureus* in salt condition by SFV33. Similar effects were also detected for SFV33 in plasma on *P. aeruginosa* but not for LL-37. The other peptides were not able to induce membrane permeabilization at physiological conditions as observed on *S. aureus*. However, they displayed membrane damage in the presence of salt on *P. aeruginosa* (FIG. 9A).

The effect of SFV33 on bacterial membranes was further examined with high resolution scanning electron microscopy. At the ultrastructural level, SFV33 caused disruption of bacteria, leading to disintegration and ejection of cytoplasmic components in the presence of salt (*P. aeruginosa* and *S. aureus*) and plasma (*P. aeruginosa*) (FIG. 9B). Bacteria treated with DVN32 did not show any membrane damage and were similar to controls. These results further support the idea that collagen type VI-derived peptide SFV33 disrupts the cell membranes of *P. aeruginosa* and *S. aureus* at physiological ionic strength similar to those seen for LL-37.

To investigate the effect of collagen type VI-derived peptides on membranes a liposome model was used to study membrane permeabilization. Peptides were tested for membrane leakage in a liposome model membrane system (*E. coli* polar lipid extract). The results showed that all peptides have the ability to cause membrane permeabilization at physiological pH, except DVN32 (FIG. 10A). The peptides induced a concentration dependent release of carboxyfluorescein. FYL25 and SFV33 induced highest membrane leakage compared to VTT30 (FIG. 10B). Taken together, these results strongly support the implications of the leakage assay, propidium iodide uptake and scanning electron microscopy experiments that the antimicrobial activity of collagen type VI-peptides, such as SFV33, likely results from damage to the bacterial cell membrane.

Peptides Effect on Eukaryotic Cells

One major side effect for some AMPs is that they do not only act on bacterial membranes but they can also destroy and eliminate eukaryotic cells. The cytotoxic effect of different concentrations of peptides on erythrocytes and monocytes was assessed. 2% Triton X-100 was used as cytotoxic agent, a positive control. The results show that peptides did not show any toxicity towards erythrocytes and monocytes at concentrations up to 30 µM, in contrast to LL-37 (FIGS. 11A and B). Although, SFV33 exhibited toxicity at 50 µM for monocytes (FIG. 11B). Nevertheless, these results demonstrate that collagen type VI-derived peptides did not affect viability of the human cells at any of the concentrations used to kill bacteria.

Immunomodulatory Properties of Collagen Type VI-Derived Peptides

LPS is a well-studied endotoxin released by the outer membrane of Gram-negative bacteria and play an important role in pathogenesis of certain bacterial diseases. A massive release of LPS can cause endotoxic shock, and lead to death (50). The immunomodulatory effects of collagen type VI derived peptides were investigated. Murine macrophage-like cells were stimulated simultaneously with *E. coli* LPS and collagen type VI-derived peptides and the amount of nitrite in the supernatant was measured with Greiss reagent. As shown in FIG. 12, the addition of GVR28 significantly suppressed the LPS-induction of nitrite, which is similar to those seen after LL-37 treatment. In contrast, the other peptides were unable to block LPS-induced nitrite production.

To examine the biological effect of synthetic collagen type VI-derived peptides on wound healing, HaCaT cells were cultured in wells of 24-well plate; cells were scratched and incubated with intact collagen type VI, collagen type VI-derived peptides or LL-37 (10 µg/ml). Cell migration was recorded by photomicrograph at post-scratched 0 hour and 24 h. As illustrated in FIG. 13, collagen type VI-derived peptides showed a remarkable wound closure capacity after 24 h compared to controls cells without supplement. SFV33 peptide did not promote wound healing.

Example C

Introduction

The purpose of this study was to assess the antimicrobial effects of collagen type VI derived peptides on bacteria which are resistant to many conventional antibiotic agents (52, 53). Additionally, this study assessed the effect of collagen type VI on the membranes of resistant bacteria.

Materials and Methods

Microorganisms and Culture Conditions

The following multidrug-resistant bacterial strains were kindly provided by Lisa Påhlman. (Dept. of Infection Medicine, Lund University): *Pseudomonas aeruginosa* (MRPA), *Staphylococcus aureus* (MRSA) *Escherichia coli* (MREC),

*Staphylococcus epidermidis* (MRSE) and *Klebsiella pneumoniae* (MRKP) All tested multidrug-resistant microorganisms were clinical isolates from patients with either bacteremia or pneumonia. All strains were grown overnight in Todd-Hewitt broth (THB, Gibco, Grand Island, NY USA) at 37° C. in a humid atmosphere containing 5%.

Antibacterial Activity Assay

Bacteria were grown to mid logarithmic phase in Todd-Hewitt broth ($OD_{20}$≈0.4), harvested by centrifugation at 3,500 rpm for 10 min and washed twice in TBS buffer. Bacterial suspensions were adjusted to $2 \times 10^9$ colony forming units (cfu) per ml. The bacteria were further diluted in TBS and incubated with different collagen type VI or collagen type VI peptide concentrations. Bacteria incubated with TBS or 3 µM LL-37 antimicrobial peptide (Innovagen, Lund, Sweden) were used as negative or positive controls, respectively. Samples were incubated for 2 h at 37° C. in a humid atmosphere containing 5% $CO_2$. Serial dilutions were plated on agar plates, incubated overnight at 37° C., and the number of cfu were thereafter determined by counting visible colonies. Experiments were performed in triplicate.

Scanning Electron Microscopy

For high resolution field emission transmission electron microscopy (FESEM), specimens were fixed over night at RT with 2.5% glutaraldehyde in cacodylate buffer. They were then washed with cacodylate buffer and dehydrated with an ascending ethanol series from 50% (v/v) to absolute ethanol. The specimens were then subjected to critical point drying with carbon dioxide and absolute ethanol was used as an intermediate solvent. The tissue samples were mounted on aluminum holders, sputtered with 20 nm palladium/gold, and examined in a Philips/FEI XL 30 FESEM scanning electron microscope using an Everhart-Tornley secondary electron detector.

Results and Conclusions

Collagen Type VI and Collagen Type VI-Derived Peptides are Antimicrobial Against Multidrug-Resistant Mammalian Pathogens In order to assess possible antibacterial effects of collagen type VI and peptides thereof, bacteria were treated with purified preparations of this protein and its peptides. Bacteria treated with TBS buffer or the cathelicidin peptide LL-37 served as negative and positive controls, respectively. The results from viable-count assays show killing of multidrug-resistant human pathogens (FIG. 14A-C). Treatment for 2 h at 37° C. significantly inhibited bacterial growth as compared to control bacteria treated with TBS. Notably, the efficiency of bacterial clearance was comparable to the "classical" human antimicrobial peptide LL-37, or better.

Collagen Type VI Killing Properties are Associated with *Streptococcus* and *Pseudomonas* Membrane Disruption as Determined by Electron Microscopy—

For a more detailed understanding of the underlying killing mechanism human skin biopsies were inoculated with MRSA and MRPA (as model systems) in the presence or absence of collagen type VI and visualized by scanning electron microscopy. FIG. 15 depicts the bactericidal effect of this molecule as indicated. In the presence of collagen type VI membrane perturbations, blebbing and exudation of cytoplasmic content were observed. Large scale membrane destabilization events finally lead to disintegration of the bacterial cells into a mixture of membrane vesicles and cytoplasmic ejecta. Taken together, the data presented in FIGS. 14 and 15 show that collagen type VI and/or parts of this molecule exert antimicrobial activity against multidrug-resistant human pathogens by mechanisms including membrane rupture. The antimicrobial effect is dose-dependent at physiological pH and salt concentrations.

Example D

Introduction

The purpose of this study was to assess the antimicrobial effects of amphipathic peptides derived from the collagen VI amino acid sequence, in an in vivo infection model in mice, of bacterial infection with an invasive *Pseudomonas aeruginosa* (abbreviated as *P. aeruginosa*).

Materials and Methods

Microorganisms and Culture Conditions

*P. aeruginosa* 15159 strain was grown overnight in Todd-Hewitt broth (THB, Gibco, Grand Island, NY USA) at 37° C. in a humid atmosphere containing 5% $CO_2$.

Animal Experiments

Animal experiments were performed according to a protocol approved by the Local Ethics Committee at Lund University. Animals were housed under standard conditions of light and temperature and had free access to standard laboratory chow and water. *P. aeruginosa* 15159 bacteria were grown to mid-exponential phase ($A_{620}$~0.5), washed and diluted in PBS to $2 \times 10^8$ cfu/ml, and kept on ice until injection. Female BALB/c mice, 8 weeks old, were anesthetized with isoflurane and injected intraperitoneally with 100 µL of the bacterial solution, followed by injection of 100 µL SFV33 or GVR28 peptide (1 mg/mL) after 15 minutes, or with 100 µL PBS alone (control group).

Results

The Effect of Treatment with Collagen VI-Derived Peptides on Survival of Infected Mice A beneficial effect of SFV33 and GVR28 was demonstrated in murine survival studies. Intraperitoneally infected mice were treated with a single dose of SFV33 or GVR28 15 minutes after infection, and the survival was recorded. FIG. 17 shows that 50% of infected mice treated with PBS died during the first 12 hours. In contrast, in the SFV33 and GVR28-treated groups, 50% mortalities were observed for animals after 24 hours. Comparing the overall mortality rate of the SFV33/GVR28 and PBS groups, the peptide-treated animal groups both showed prolonged survival when the experiment was terminated after 29 hours.

REFERENCES

1. Hawkey, P. M. (2008) The growing burden of antimicrobial resistance. *The Journal of antimicrobial chemotherapy* 62 Suppl 1, i1-9
2. Livermore, D. M. (2009) Has the era of untreatable infections arrived? *The Journal of antimicrobial chemotherapy* 64 Suppl 1, i29-36
3. Diamond, G., Beckloff, N., Weinberg, A., and Kisich, K. O. (2009) The roles of antimicrobial peptides in innate host defence. *Current pharmaceutical design* 15, 2377-2392
4. Hancock, R. E., and Sahl, H. G. (2006) Antimicrobial and host-defence peptides as new anti-infective therapeutic strategies. *Nature biotechnology* 24, 1551-1557
5. Fearon, D. T., and Locksley, R. M. (1996) The instructive role of innate immunity in the acquired immune response. *Science* 272, 50-53
6. Schroder, J. M., and Harder, J. (1999) Human beta-defensin-2. *The international journal of biochemistry & cell biology* 31, 645-651

7. Boman, H. G. (2000) Innate immunity and the normal microflora. *Immunological reviews* 173, 5-16
8. Zasloff, M. (2002) Antimicrobial peptides of multicellular organisms. *Nature* 415, 389-395
9. Yount, N. Y., Bayer, A. S., Xiong, Y. Q., and Yeaman, M. R. (2006) Advances in antimicrobial peptide immunobiology. *Biopolymers* 84, 435-458
10. Teixeira, V., Feio, M. J., and Bastos, M. (2012) Role of lipids in the interaction of antimicrobial peptides with membranes. *Progress in lipid research* 51, 149-177
11. Fjell, C. D., Hiss, J. A., Hancock, R. E., and Schneider, G. (2012) Designing antimicrobial peptides: form follows function. *Nature reviews. Drug discovery* 11, 37-51
12. Brogden, K. A. (2005) Antimicrobial peptides: pore formers or metabolic inhibitors in bacteria? *Nature reviews. Microbiology* 3, 238-250
13. Shai, Y. (1999) Mechanism of the binding, insertion and destabilization of phospholipid bilayer membranes by alpha-helical antimicrobial and cell non-selective membrane-lytic peptides. *Biochimica et biophysica acta* 1462, 55-70
14. Shai, Y. (2002) Mode of action of membrane active antimicrobial peptides. *Biopolymers* 66, 236-248
15. Melo, M. N., Ferre, R., and Castanho, M. A. (2009) Antimicrobial peptides: linking partition, activity and high membrane-bound concentrations. *Nature reviews. Microbiology* 7, 245-250
16. Peters, B. M., Shirtliff, M. E., and Jabra-Rizk, M. A. (2010) Antimicrobial peptides: primeval molecules or future drugs? PLoS pathogens 6, e1001067
17. Brown, K. L., and Hancock, R. E. (2006) Cationic host defence (antimicrobial) peptides. *Current opinion in immunology* 18, 24-30
18. Bowdish, D. M., Davidson, D. J., and Hancock, R. E. (2005) A re-evaluation of the role of host defence peptides in mammalian immunity. *Current protein & peptide science* 6, 35-51
19. Bradshaw, J. (2003) Cationic antimicrobial peptides: issues for potential clinical use. *BioDrugs: clinical immunotherapeutics, biopharmaceuticals and gene therapy* 17, 233-240
20. Singh, B., Fleury, C., Jalalvand, F., and Riesbeck, K. (2012) Human pathogens utilize host extracellular matrix proteins laminin and collagen for adhesion and invasion of the host. *FEMS microbiology reviews* 36, 1122-1180
21. Senyurek, I., Kempf, W. E., Klein, G., Maurer, A., Kalbacher, H., Schafer, L., Wanke, I., Christ, C., Stevanovic, S., Schaller, M., Rousselle, P., Garbe, C., Biedermann, T., and Schittek, B. (2014) Processing of Laminin alpha Chains Generates Peptides Involved in Wound Healing and Host Defence. *Journal of innate immunity*
22. Senyurek, I., Klein, G., Kalbacher, H., Deeg, M., and Schittek, B. (2010) Peptides derived from the human laminin alpha4 and alpha5 chains exhibit antimicrobial activity. *Peptides* 31, 1468-1472
23. Brennan, E. P., Reing, J., Chew, D., Myers-Irvin, J. M., Young, E. J., and Badylak, S. F. (2006) Antibacterial activity within degradation products of biological scaffolds composed of extracellular matrix. *Tissue engineering* 12, 2949-2955
24. Sarikaya, A., Record, R., Wu, C. C., Tullius, B., Badylak, S., and Ladisch, M. (2002) Antimicrobial activity associated with extracellular matrices. *Tissue engineering* 8, 63-71
25. Specks, U., Mayer, U., Nischt, R., Spissinger, T., Mann, K., Timpl, R., Engel, J., and Chu, M. L. (1992) Structure of recombinant N-terminal globule of type VI collagen alpha 3 chain and its binding to heparin and hyaluronan. *The EMBO journal* 11, 4281-4290
26. Chu, M. L., Pan, T. C., Conway, D., Kuo, H. J., Glanville, R. W., Timpl, R., Mann, K., and Deutzmann, R. (1989) Sequence analysis of alpha 1(VI) and alpha 2(VI) chains of human type VI collagen reveals internal triplication of globular domains similar to the A domains of von Willebrand factor and two alpha 2(VI) chain variants that differ in the carboxy terminus. *The EMBO journal* 8, 1939-1946
27. Chu, M. L., Zhang, R. Z., Pan, T. C., Stokes, D., Conway, D., Kuo, H. J., Glanville, R., Mayer, U., Mann, K., Deutzmann, R., and et al. (1990) Mosaic structure of globular domains in the human type VI collagen alpha 3 chain: similarity to von Willebrand factor, fibronectin, actin, salivary proteins and aprotinin type protease inhibitors. *The EMBO journal* 9, 385-393
28. Chu, M. L., Pan, T. C., Conway, D., Saitta, B., Stokes, D., Kuo, H. J., Glanville, R. W., Timpl, R., Mann, K., and Deutzmann, R. (1990) The structure of type VI collagen. *Annals of the New York Academy of Sciences* 580, 55-63
29. Lamande, S. R., Mörgelin, M., Adams, N. E., Selan, C., and Allen, J. M. (2006) The C5 domain of the collagen type VI alpha3(VI) chain is critical for extracellular microfibril formation and is present in the extracellular matrix of cultured cells. *The Journal of biological chemistry* 281, 16607-16614
30. Cescon, M., Gattazzo, F., Chen, P., and Bonaldo, P. (2015) Collagen VI at a glance. *Journal of cell science* 128, 3525-3531
31. Hileman, R. E., Fromm, J. R., Weiler, J. M., and Linhardt, R. J. (1998) Glycosaminoglycan-protein interactions: definition of consensus sites in glycosaminoglycan binding proteins. *BioEssays: news and reviews in molecular, cellular and developmental biology* 20, 156-167
32. Andersson, E., Rydengard, V., Sonesson, A., Mörgelin, M., Björck, L., and Schmidtchen, A. (2004) Antimicrobial activities of heparin-binding peptides. *European journal of biochemistry/FEBS* 271, 1219-1226
33. Ringstad, L., Schmidtchen, A., and Malmsten, M. (2006) Effect of peptide length on the interaction between consensus peptides and DOPC/DOPA bilayers. *Langmuir: the ACS journal of surfaces and colloids* 22, 5042-5050
34. Spissinger, T. & Engel, J. (1995) Type VI collagen beaded microfibrils from bovine cornea depolymerize at acidic pH, and depolymerization and polymerization are not influenced by hyaluronan. *Matrix Biol.* 14(6):499-505.
35. Bober, M., Enochsson, C., Collin, M., and Mórgelin, M. (2010) Collagen VI is a subepithelial adhesive target for human respiratory tract pathogens. *Journal of innate immunity* 2, 160-166
36. Abdillahi, S. M., Balvanovic, S., Baumgarten, M., and Mörgelin, M. (2012) Collagen VI encodes antimicrobial activity: novel innate host defence properties of the extracellular matrix. *Journal of innate immunity* 4, 371-376
37. Abdillahi, S. M., Bober, M., Nordin, S., Hallgren, O., Baumgarten, M., Erjefält, J., Westergren-Thorsson, G., Bjermer, L., Riesbeck, K., Egesten, A., and Mórgelin, M. (2015) Collagen VI Is Upregulated in COPD and Serves Both as an Adhesive Target and a Bactericidal Barrier for *Moraxella catarrhalis*. *Journal of innate immunity*
38. Gara, S. K., Grumati, P., Squarzoni, S., Sabatelli, P., Urciuolo, A., Bonaldo, P., Paulsson, M., and Wagener, R. (2011) Differential and restricted expression of novel collagen VI chains in mouse. *Matrix biology: journal of the International Society for Matrix Biology* 30, 248-257

39. Maertens, B., Hopkins, D., Franzke, C. W., Keene, D. R., Bruckner-Tuderman, L., Greenspan, D. S., and Koch, M. (2007) Cleavage and oligomerization of gliomedin, a transmembrane collagen required for node of ranvier formation. *The Journal of biological chemistry* 282, 10647-10659

40. Oehmcke, S., Mórgelin, M., and Herwald, H. (2009) Activation of the human contact system on neutrophil extracellular traps. *Journal of innate immunity* 1, 225-230

41. Baschong, W., and Wrigley, N. G. (1990) Small colloidal gold conjugated to Fab fragments or to immunoglobulin G as high-resolution labels for electron microscopy: a technical overview. *Journal of electron microscopy technique* 14, 313-323

42. Becker, A. K., Mikolajek, H., Paulsson, M., Wagener, R., and Werner, J. M. (2014) A structure of a collagen VI VWA domain displays N and C termini at opposite sides of the protein. *Structure* 22, 199-208

43. Lehrer, R. I., Rosenman, M., Harwig, S. S., Jackson, R., and Eisenhauer, P. (1991) Ultrasensitive assays for endogenous antimicrobial polypeptides. *Journal of immunological methods* 137, 167-173

44. Malmsten, M., Davoudi, M., and Schmidtchen, A. (2006) Bacterial killing by heparin-binding peptides from PRELP and thrombospondin. *Matrix biology: journal of the International Society for Matrix Biology* 25, 294-300

45. Wimley, W. C. (2010) Describing the mechanism of antimicrobial peptide action with the interfacial activity model. *ACS chemical biology* 5, 905-917

46. Kasetty, G., Papareddy, P., Kalle, M., Rydengard, V., Walse, B., Svensson, B., Mórgelin, M., Malmsten, M., and Schmidtchen, A. (2011) The C-terminal sequence of several human serine proteases encodes host defence functions. *Journal of innate immunity* 3, 471-482

47. Pasupuleti, M., Walse, B., Svensson, B., Malmsten, M., and Schmidtchen, A. (2008) Rational design of antimicrobial C3a analogues with enhanced effects against Staphylococci using an integrated structure and function-based approach. *Biochemistry* 47, 9057-9070

48. Wang, Y., Agerberth, B., Lothgren, A., Almstedt, A., and Johansson, J. (1998) Apolipoprotein A-I binds and inhibits the human antibacterial/cytotoxic peptide LL-37. *The Journal of biological chemistry* 273, 33115-33118

49. Ganz, T. (2001) Antimicrobial proteins and peptides in host defence. *Seminars in respiratory infections* 16, 4-10

50. Ramachandran, G. (2014) Gram-positive and gram-negative bacterial toxins in sepsis: a brief review. *Virulence* 5, 213-218

51. Chu, M. L., Conway, D., Pan, T. C., Baldwin, C., Mann, K., Deutzmann, R., and Timpl, R. (1988) Amino acid sequence of the triple-helical domain of human collagen type VI. *The Journal of biological chemistry* 263, 18601-18606

52. MacVane, S. H. (2016) Antimicrobial Resistance in the Intensive Care Unit: A Focus on Gram-Negative Bacterial Infections. *The Journal of intensive care medicine,* [*Epub ahead of print*]

53. Bhattacharya, P. K. (2014) Emergence of antibiotic-resistant bacterial strains, methicillin-resistant *Staphylococcus aureus*, extended spectrum beta lactamases, and multi-drug resistance is a problem similar to global warming. *Revista da Sociedade Brasileira de Medicina Tropical* 47, 815-816

The invention claimed is:

1. A polypeptide comprising an amino acid sequence selected from the group consisting of:
   (a) SEQ ID NO: 2 derived from the α3 chain of collagen type VI,
   (b) a fragment of SEQ ID NO: 2, wherein the fragment of SEQ ID NO: 2 comprises at least 20 contiguous amino acids of SEQ ID NO: 2, and
   (c) a variant of SEQ ID NO: 2, wherein the variant comprises an amino acid sequence with at least 80% sequence identity to SEQ ID NO: 2, wherein the polypeptide is between 20 and 200 amino acids in length, and wherein the polypeptide, fragment, or variant is capable of killing or attenuating the growth of microorganisms.

2. A polypeptide according to claim 1, wherein the microorganisms are selected from the group consisting of bacteria, mycoplasmas, yeasts, fungi and viruses.

3. A polypeptide according to claim 1, wherein the polypeptide is capable of:
   (a) binding to the membrane of the microorganism,
   (b) causing membrane disruption of the microorganisms,
   (c) promoting wound closure,
   (d) exhibiting an antimicrobial effect greater than or equal to that of LL-37, and/or
   (e) exerting an anti-endotoxic effect.

4. A polypeptide according to claim 1, wherein the microorganisms are Gram-positive or Gram-negative bacteria.

5. A polypeptide according to claim 4, wherein the microorganisms are selected from the group consisting of: *Pseudomonas aeruginosa, Staphylococcus aureus, Escherichia coli*, group A *streptococcus, Streptococcus pyogenes*, group B *streptococcus, Streptococcus agalactiae*, group C *streptococcus, Streptococcus dysgalactiae*, group D *streptococcus, Enterococcus faecalis*, group F *streptococcus, Streptococcus anginosus*, group G *streptococcus, Streptococcus dysgalactiae equisimilis*, alpha-hemolytic *streptococcus, Streptococcus viridans, Streptococcus pneumoniae, Streptococcus bovis, Streptococcus mitis, Streptococcus anginosus, Streptococcus sanguinis, Streptococcus suis, Streptococcus mutans, Moraxella catarrhalis*, Non-typeable *Haemophilus influenzae* (NTHi), *Haemophilus influenzae* b (Hib), *Actinomyces naeslundii, Fusobacterium nucleatum, Prevotella intermedia, Klebsiella pneumoniae, Enterococcus cloacae, Enterococcus faecalis, Staphylococcus epidermidis*, multi-resistant *Pseudomonas aeruginosa* (MRPA), multi-resistant *Staphylococcus aureus* (MRSA), multi-resistant *Escherichia coli* (MREC), multi-resistant *Staphylococcus epidermidis* (MRSE) and multi-resistant *Klebsiella pneumoniae* (MRKP).

6. A polypeptide according to claim 1, wherein the microorganisms are bacteria which are resistant to one or more conventional antibiotic agents, optionally wherein the microorganism is selected from the group consisting of: multidrug-resistant *Staphylococcus aureus* (MRSA), multidrug-resistant *Pseudomonas aeruginosa* (MRPA), multi-resistant *Escherichia coli* (MREC), multi-resistant *Staphylococcus epidermidis* (MRSE) and multi-resistant *Klebsiella pneumoniae* (MRKP).

7. A polypeptide according to claim 1, wherein the polypeptide is substantially non-toxic to mammalian cells.

8. A polypeptide according to claim 1, wherein the polypeptide has a net positive charge.

9. A polypeptide according to claim 8, wherein the charge on the polypeptide ranges from between +2 to +9.

10. A polypeptide according to claim 1, wherein the polypeptide has at least 30% hydrophobic residues.

11. A polypeptide according to claim 1, wherein the variant has at least 90% identity with the amino acid sequence amino acid sequence of SEQ ID NO: 2.

12. A polypeptide according to claim 1, wherein the polypeptide is between 20 and 40 amino acids in length.

13. A polypeptide according to claim 12, wherein the polypeptide is between 25 and 35 amino acids in length.

14. A polypeptide according to claim 1, wherein the polypeptide, fragment, or variant thereof comprises one or more amino acids that are modified or derivatised, wherein the modification or derivatization is PEGylation, amidation, esterification, acylation, acetylation and/or alkylation.

15. A pharmaceutical composition comprising a polypeptide according to claim 1 and a pharmaceutically acceptable excipient, diluent, carrier, buffer or adjuvant, optionally wherein the pharmaceutical composition is suitable for administration via a route selected from the group consisting of oral administration, parenteral administration and topical administration.

16. A medical device, implant, wound care product, or material which is coated, impregnated, admixed or otherwise associated with a pharmaceutical composition according to claim 15.

17. A medical device, implant, wound care product, or material according to claim 16, wherein the medical device, implant, wound care product, or material is utilized in by-pass surgery, extracorporeal circulation, wound care and/or dialysis.

18. A medical device, implant, wound care product, or material according to claim 16, wherein the pharmaceutical composition is coated, painted, sprayed or otherwise applied to a suture, prosthesis, implant, wound dressing, catheter, lens, skin graft, skin substitute, fibrin glue or bandage.

19. A polypeptide according to claim 1, wherein the polypeptide consists of an amino acid sequence selected from the group consisting of:
   (a) SEQ ID NO: 2 from the α3 chain of collagen type VI;
   (b) a fragment of SEQ ID NO: 2, wherein the fragment of SEQ ID NO: 2 comprises at least 20 contiguous amino acids of SEQ ID NO: 2; and
   (c) a variant of SEQ ID NO: 2, wherein the variant consists of an amino acid sequence with at least 80% sequence identity to SEQ ID NO: 2.

* * * * *

SEQUENCE LISTING

```
Sequence total quantity: 46
SEQ ID NO: 1              moltype = AA  length = 28
FEATURE                   Location/Qualifiers
REGION                    1..28
                          note = GVR28 peptide
source                    1..28
                          mol_type = protein
                          organism = synthetic construct
SEQUENCE: 1
GVRPDGFAHI RDFVSRIVRR LNIGPSKV                                       28

SEQ ID NO: 2              moltype = AA  length = 25
FEATURE                   Location/Qualifiers
REGION                    1..25
                          note = FYL25 peptide
source                    1..25
                          mol_type = protein
                          organism = synthetic construct
SEQUENCE: 2
FYLKTYRSQA PVLDAIRRLR LRGGS                                          25

SEQ ID NO: 3              moltype = AA  length = 25
FEATURE                   Location/Qualifiers
REGION                    1..25
                          note = FFL25 peptide
source                    1..25
                          mol_type = protein
                          organism = synthetic construct
SEQUENCE: 3
FFLKDFSTKR QIIDAINKVV YKGGR                                          25

SEQ ID NO: 4              moltype = AA  length = 30
FEATURE                   Location/Qualifiers
REGION                    1..30
                          note = VTT30 peptide
source                    1..30
```

```
                                 mol_type = protein
                                 organism = synthetic construct
SEQUENCE: 4
VTTEIRFADS KRKSVLLDKI KNLQVALTSK                                        30

SEQ ID NO: 5            moltype = AA   length = 33
FEATURE                 Location/Qualifiers
REGION                  1..33
                        note = SFV33 peptide
source                  1..33
                        mol_type = protein
                        organism = synthetic construct
SEQUENCE: 5
SFVARNTFKR VRNGFLMRKV AVFFSNTPTR ASP                                    33

SEQ ID NO: 6            moltype = AA   length = 32
FEATURE                 Location/Qualifiers
REGION                  1..32
                        note = DVN32 peptide
source                  1..32
                        mol_type = protein
                        organism = synthetic construct
SEQUENCE: 6
DVNVFAIGVE DADEGALKEI ASEPLNMHMF NL                                     32

SEQ ID NO: 7            moltype = AA   length = 20
FEATURE                 Location/Qualifiers
REGION                  1..20
                        note = KPE20 peptide
source                  1..20
                        mol_type = protein
                        organism = synthetic construct
SEQUENCE: 7
KPEILNLVKR MKIKTGKALN                                                   20

SEQ ID NO: 8            moltype = AA   length = 20
FEATURE                 Location/Qualifiers
REGION                  1..20
                        note = GFA20 peptide
source                  1..20
                        mol_type = protein
                        organism = synthetic construct
SEQUENCE: 8
GFAHIRDFVS RIVRRLNIGP                                                   20

SEQ ID NO: 9            moltype = AA   length = 20
FEATURE                 Location/Qualifiers
REGION                  1..20
                        note = QAP20 peptide
source                  1..20
                        mol_type = protein
                        organism = synthetic construct
SEQUENCE: 9
QAPVLDAIRR LRLRGGSPLN                                                   20

SEQ ID NO: 10           moltype = AA   length = 20
FEATURE                 Location/Qualifiers
REGION                  1..20
                        note = KGF20 peptide
source                  1..20
                        mol_type = protein
                        organism = synthetic construct
SEQUENCE: 10
KGFESKVDAI LNRISQMHRV                                                   20

SEQ ID NO: 11           moltype = AA   length = 20
FEATURE                 Location/Qualifiers
REGION                  1..20
                        note = RKV20 peptide
source                  1..20
                        mol_type = protein
                        organism = synthetic construct
SEQUENCE: 11
RKVAVFFSNT PTRASPQLRE                                                   20

SEQ ID NO: 12           moltype = AA   length = 20
FEATURE                 Location/Qualifiers
REGION                  1..20
                        note = VAA20
```

```
source                      1..20
                            mol_type = protein
                            organism = synthetic construct
SEQUENCE: 12
VAAKPVATKM AVRPPVAVKP                                                   20

SEQ ID NO: 13               moltype = AA   length = 20
FEATURE                     Location/Qualifiers
REGION                      1..20
                            note = AAK20 peptide
source                      1..20
                            mol_type = protein
                            organism = synthetic construct
SEQUENCE: 13
AAKPVATKPE VPRPQAAKPA                                                   20

SEQ ID NO: 14               moltype = AA   length = 20
FEATURE                     Location/Qualifiers
REGION                      1..20
                            note = TTK20 peptide
source                      1..20
                            mol_type = protein
                            organism = synthetic construct
SEQUENCE: 14
TTKPVTTTKP VTTTTKPVTT                                                   20

SEQ ID NO: 15               moltype = AA   length = 76
FEATURE                     Location/Qualifiers
REGION                      1..76
                            note = AAA76 peptide
source                      1..76
                            mol_type = protein
                            organism = synthetic construct
SEQUENCE: 15
AAAKPAPAKP VAAKPVATKM ATVRPPVAVK PATAAKPVAA KPAAVRPPAA AAAKPVATKP        60
EVPRPQAAKP AATKPA                                                       76

SEQ ID NO: 16               moltype = AA   length = 36
FEATURE                     Location/Qualifiers
REGION                      1..36
                            note = TSS36 peptide
source                      1..36
                            mol_type = protein
                            organism = synthetic construct
SEQUENCE: 16
TSSPTSNPVT TTKPVTTTKP VTTTTKPVTT TTKPVT                                 36

SEQ ID NO: 17               moltype = AA   length = 20
FEATURE                     Location/Qualifiers
REGION                      1..20
                            note = YDR20 peptide
source                      1..20
                            mol_type = protein
                            organism = synthetic construct
SEQUENCE: 17
YDRLIKESRR QKTRVFAVVI                                                   20

SEQ ID NO: 18               moltype = AA   length = 20
FEATURE                     Location/Qualifiers
REGION                      1..20
                            note = EQN20 peptide
source                      1..20
                            mol_type = protein
                            organism = synthetic construct
SEQUENCE: 18
EQNFHKARRF VEQVARRLTL                                                   20

SEQ ID NO: 19               moltype = AA   length = 20
FEATURE                     Location/Qualifiers
REGION                      1..20
                            note = VVH20 peptide
source                      1..20
                            mol_type = protein
                            organism = synthetic construct
SEQUENCE: 19
VVHAINAIVR SPRGGARRHA                                                   20

SEQ ID NO: 20               moltype = AA   length = 20
FEATURE                     Location/Qualifiers
```

```
REGION                    1..20
                          note = LRL20 peptide
source                    1..20
                          mol_type = protein
                          organism = synthetic construct
SEQUENCE: 20
LRLKPYGALV DKVKSFTKRF                                               20

SEQ ID NO: 21             moltype = AA  length = 20
FEATURE                   Location/Qualifiers
REGION                    1..20
                          note = FTK20 peptide
source                    1..20
                          mol_type = protein
                          organism = synthetic construct
SEQUENCE: 21
FTKRFIDNLR DRYYRCDRNL                                               20

SEQ ID NO: 22             moltype = AA  length = 20
FEATURE                   Location/Qualifiers
REGION                    1..20
                          note = RDA20 peptide
source                    1..20
                          mol_type = protein
                          organism = synthetic construct
SEQUENCE: 22
RDALKSSVDA VKYFGKGTYT                                               20

SEQ ID NO: 23             moltype = AA  length = 20
FEATURE                   Location/Qualifiers
REGION                    1..20
                          note = TKR20 peptide
source                    1..20
                          mol_type = protein
                          organism = synthetic construct
SEQUENCE: 23
TKRFAKRLAE RFLTAGRTDP                                               20

SEQ ID NO: 24             moltype = DNA  length = 28
FEATURE                   Location/Qualifiers
misc_feature              1..28
                          note = alpha1N(fw) primer
source                    1..28
                          mol_type = other DNA
                          organism = synthetic construct
SEQUENCE: 24
agagctagca tgccctgtgg atctattc                                      28

SEQ ID NO: 25             moltype = DNA  length = 29
FEATURE                   Location/Qualifiers
misc_feature              1..29
                          note = alpha1N(rev) primer
source                    1..29
                          mol_type = other DNA
                          organism = synthetic construct
SEQUENCE: 25
gcactcgaga atcatgtcca caatggtgt                                     29

SEQ ID NO: 26             moltype = DNA  length = 29
FEATURE                   Location/Qualifiers
misc_feature              1..29
                          note = alpha1C(fw) primer
source                    1..29
                          mol_type = other DNA
                          organism = synthetic construct
SEQUENCE: 26
gcagctagct gcacatgtgg acccattga                                     29

SEQ ID NO: 27             moltype = DNA  length = 27
FEATURE                   Location/Qualifiers
misc_feature              1..27
                          note = alpha1C(rev) primer
source                    1..27
                          mol_type = other DNA
                          organism = synthetic construct
SEQUENCE: 27
aacctcgagg cccagtgcca ccttcct                                       27

SEQ ID NO: 28             moltype = DNA  length = 27
```

```
FEATURE               Location/Qualifiers
misc_feature          1..27
                      note = alpha2N(fw) primer
source                1..27
                      mol_type = other DNA
                      organism = synthetic construct
SEQUENCE: 28
agagctagca aggccgactg cccagtc                                              27

SEQ ID NO: 29         moltype = DNA  length = 27
FEATURE               Location/Qualifiers
misc_feature          1..27
                      note = alpha2N(rev) primer
source                1..27
                      mol_type = other DNA
                      organism = synthetic construct
SEQUENCE: 29
gcactcgagg accttgatga tgcggtt                                              27

SEQ ID NO: 30         moltype = DNA  length = 27
FEATURE               Location/Qualifiers
misc_feature          1..27
                      note = alpha2C(fw) primer
source                1..27
                      mol_type = other DNA
                      organism = synthetic construct
SEQUENCE: 30
gaagctagct gtgagaagcg ctgtggt                                              27

SEQ ID NO: 31         moltype = DNA  length = 25
FEATURE               Location/Qualifiers
misc_feature          1..25
                      note = alpha2C(rev) primer
source                1..25
                      mol_type = other DNA
                      organism = synthetic construct
SEQUENCE: 31
gcaggatcca cagatccagc ggatg                                                25

SEQ ID NO: 32         moltype = DNA  length = 32
FEATURE               Location/Qualifiers
misc_feature          1..32
                      note = alpha3N(fw) primer
source                1..32
                      mol_type = other DNA
                      organism = synthetic construct
SEQUENCE: 32
tatctcgagc tgatggatct gctgtgaggt ta                                        32

SEQ ID NO: 33         moltype = DNA  length = 39
FEATURE               Location/Qualifiers
misc_feature          1..39
                      note = alpha3N(rev) primer
source                1..39
                      mol_type = other DNA
                      organism = synthetic construct
SEQUENCE: 33
aggaaccagg gatcccaggg gcctgtcata catgaagcc                                 39

SEQ ID NO: 34         moltype = DNA  length = 32
FEATURE               Location/Qualifiers
misc_feature          1..32
                      note = alpha3C(fw) primer
source                1..32
                      mol_type = other DNA
                      organism = synthetic construct
SEQUENCE: 34
aaagctagcc tggagtgccc tgtattccca ac                                        32

SEQ ID NO: 35         moltype = DNA  length = 32
FEATURE               Location/Qualifiers
misc_feature          1..32
                      note = alpha3C(rev) primer
source                1..32
                      mol_type = other DNA
                      organism = synthetic construct
SEQUENCE: 35
tttggatcct caaactgtta actcaggact ac                                        32
```

```
SEQ ID NO: 36              moltype = AA   length = 37
FEATURE                    Location/Qualifiers
REGION                     1..37
                           note = LL-37 peptide
source                     1..37
                           mol_type = protein
                           organism = synthetic construct
SEQUENCE: 36
LLGDFFRKSK EKIGKEFKRI VQRIKDFLRN LVPRTES                              37

SEQ ID NO: 37              moltype = AA   length = 185
FEATURE                    Location/Qualifiers
REGION                     1..185
                           note = human collagen type VI alpha3-chain VWA domain
                             alpha3_N10
source                     1..185
                           mol_type = protein
                           organism = Homo sapiens
SEQUENCE: 37
ADIIFLVDSS WTIGEEHFQL VREFLYDVVK SLAVGENDFH FALVQFNGNP HTEFLLNTYR  60
TKQEVLSHIS NMSYIGGTNQ TGKGLEYIMQ SHLTKAAGSR AGDGVPQVIV VLTDGHSKDG 120
LALPSAELKS ADVNVFAIGV EDADEGALKE IASEPLNMHM FNLENFTSLH DIVGNLVSCV 180
HSSVS                                                            185

SEQ ID NO: 38              moltype = AA   length = 188
FEATURE                    Location/Qualifiers
REGION                     1..188
                           note = human collagen type VI alpha3-chain VWA domain
                             alpha3_N9
source                     1..188
                           mol_type = protein
                           organism = Homo sapiens
SEQUENCE: 38
TAQDSADIIF LIDGSNNTGS VNFAVILDFL VNLLEKLPIG TQQIRVGVVQ FSDEPRTMFS  60
LDTYSTKQV  LGAVKALGFA GGELANIGLA LDFVVENHFT RAGGSRVEEG VPQVLVLISA 120
GPSSDEIRYG VVALKQASVF SFGLGAQAAS RAELQHIATD DNLVFTVPEF RSFGDLQEKL 180
LPYIVGVA                                                         188

SEQ ID NO: 39              moltype = AA   length = 180
FEATURE                    Location/Qualifiers
REGION                     1..180
                           note = human collagen type VI alpha3-chain VWA domain
                             alpha3_N8
source                     1..180
                           mol_type = protein
                           organism = Homo sapiens
SEQUENCE: 39
DIVFLVDGSS ALGLANFNAI RDFIAKVIQR LEIGQDLIQV AVAQYADTVR PEFYFNTHPT  60
KREVITAVRK MKPLDGSALY TGSALDFVRN NLFTSSAGYR AAEGIPKLLV LITGGKSLDE 120
ISQPAQELKR SSIMAFAIGN KGADQAELEE IAFDSSLVFI PAEFRAAPLQ GMLPGLLAPL 180

SEQ ID NO: 40              moltype = AA   length = 182
FEATURE                    Location/Qualifiers
REGION                     1..182
                           note = human collagen type VI alpha3-chain VWA domain
                             alpha3_N7
source                     1..182
                           mol_type = protein
                           organism = Homo sapiens
SEQUENCE: 40
DIIFLLDGSA NVGKTNFPYV RDFVMNLVNS LDIGNDNIRV GLVQFSDTPV TEFSLNTYQT  60
KSDILGHLRQ LQLQGGSGLN TGSALSYVYA NHFTEAGGSR IREHVPQLLL LLTAGQSEDS 120
YLQAANALTR AGILTFCVGA SQANKAELEQ IAFNPSLVYL MDDFSSLPAL PQQLIQPLTT 180
YV                                                               182

SEQ ID NO: 41              moltype = AA   length = 179
FEATURE                    Location/Qualifiers
REGION                     1..179
                           note = human collagen type VI alpha3-chain VWA domain
                             alpha3_N6
source                     1..179
                           mol_type = protein
                           organism = Homo sapiens
SEQUENCE: 41
SKRDILFLFD GSANLVGQFP VVRDFLYKII DELNVKPEGT RIAVAQYSDD VKVESRFDEH  60
QSKPEILNLV KRMKIKTGKA LNLGYALDYA QRYIFVKSAG SRIEDGVLQF LVLLVAGRSS 120
DRVDGPASNL KQSGVVPFIF QAKNADPAEL EQIVLSPAFI LAAESLPKIG DLHPQIVNL  179

SEQ ID NO: 42              moltype = AA   length = 182
```

```
FEATURE                 Location/Qualifiers
REGION                  1..182
                        note = human collagen type VI alpha3-chain VWA domain
                        alpha3_N5
source                  1..182
                        mol_type = protein
                        organism = Homo sapiens
SEQUENCE: 42
EKDVVFLLDG SEGVRSGFPL LKEFVQRVVE SLDVGQDRVR VAVVQYSDRT RPEFYLNSYM    60
NKQDVVNAVR QLTLLGGPTP NTGAALEFVL RNILVSSAGS RITEGVPQLL IVLTADRSGD   120
DVRNPSVVVK RGGAVPIGIG IGNADITEMQ TISFIPDFAV AIPTFRQLGT VQQVISERVT   180
QL                                                                 182

SEQ ID NO: 43           moltype = AA  length = 178
FEATURE                 Location/Qualifiers
REGION                  1..178
                        note = human collagen type VI alpha3-chain VWA domain
                        alpha3_N4
source                  1..178
                        mol_type = protein
                        organism = Homo sapiens
SEQUENCE: 43
KRDVVFLIDG SQSAGPEFQY VRTLIERLVD YLDVGFDTTR VAVIQFSDDP KAEFLLNAHS    60
SKDEVQNAVQ RLRPKGGRQI NVGNALEYVS RNIFKRPLGS RIEEGVPQFL VLISSGKSDD   120
EVVVPAVELK QFGVAPFTIA RNADQEELVK ISLSPEYVFS VSTFRELPSL EQKLLTPI     178

SEQ ID NO: 44           moltype = AA  length = 186
FEATURE                 Location/Qualifiers
REGION                  1..186
                        note = human collagen type VI alpha3-chain VWA domain
                        alpha3_N3
source                  1..186
                        mol_type = protein
                        organism = Homo sapiens
SEQUENCE: 44
PPPAVESDAA DIVFLIDSSE GVRPDGFAHI RDFVSRIVRR LNIGPSKVRV GVVQFSNDVF    60
PEFYLKTYRS QAPVLDAIRR LRLRGGSPLN TGKALEFVAR NLFVKSAGSR IEDGVPQHLV   120
LVLGGKSQDD VSRFAQVIRS SGIVSLGVGD RNIDRTELQT ITNDPRLVFT VREFRELPNI   180
EERIMN                                                             186

SEQ ID NO: 45           moltype = AA  length = 181
FEATURE                 Location/Qualifiers
REGION                  1..181
                        note = human collagen type VI alpha3-chain VWA domain
                        alpha3_N2
source                  1..181
                        mol_type = protein
                        organism = Homo sapiens
SEQUENCE: 45
KKADIVFLLD GSINFRRDSF QEVLRFVSEI VDTVYEDGDS IQVGLVQYNS DPTDEFFLKD    60
FSTKRQIIDA INKVVYKGGR HANTKVGLEH LRVNHFVPEA GSRLDQRVPQ IAFVITGGKS   120
VEDAQDVSLA LTQRGVKVFA VGVRNIDSEE VGKIASNSAT AFRVGNVQEL SELSEQVLET   180
L                                                                  181

SEQ ID NO: 46           moltype = AA  length = 193
FEATURE                 Location/Qualifiers
REGION                  1..193
                        note = human collagen type VI alpha3-chain VWA domain
                        alpha3_C1
source                  1..193
                        mol_type = protein
                        organism = Homo sapiens
SEQUENCE: 46
CPVFPTELAF ALDTSEGVNQ DTFGRMRDVV LSIVNDLTIA ESNCPRGARV AVVTYNNEVT    60
TEIRFADSKR KSVLLDKIKN LQVALTSKQQ SLETAMSFVA RNTFKRVRNG FLMRKVAVFF   120
SNTPTRASPQ LREAVLKLSD AGITPLFLTR QEDRQLINAL QINNTAVGHA LVLPAGRDLT   180
DFLENVLTCH VCL                                                     193
```